(12) United States Patent
Mikoshiba et al.

(10) Patent No.: US 6,258,521 B1
(45) Date of Patent: Jul. 10, 2001

(54) SILVER HALIDE COLOR PHOTOGRAPHIC LIGHT-SENSITIVE MATERIAL, PHENIDONE COMPOUND FOR USE THEREIN, AND METHOD OF PRODUCING THE SAME

(75) Inventors: Hisashi Mikoshiba; Yasuhiro Yoshioka; Shin Soejima; Osamu Takahashi; Naoki Saito; Masakazu Morigaki, all of Minami-ashigara (JP)

(73) Assignee: Fuji Photo Film, Co., Ltd., Minami-Ashigara (JP)

( * ) Notice: Subject to any disclaimer, the term of this patent is extended or adjusted under 35 U.S.C. 154(b) by 0 days.

(21) Appl. No.: 09/163,064

(22) Filed: Sep. 24, 1998

Related U.S. Application Data

(63) Continuation-in-part of application No. PCT/JP98/00432, filed on Feb. 2, 1998.

(30) Foreign Application Priority Data

| Feb. 3, 1997 | (JP) | 20816 |
| May 29, 1997 | (JP) | 140719 |
| Jul. 22, 1997 | (JP) | 195881 |

(51) Int. Cl.$^7$ ............... G03C 1/08; G03C 7/26; G03C 7/32
(52) U.S. Cl. ............ 430/551; 430/607; 430/546; 430/543
(58) Field of Search ............... 430/483, 566, 430/546, 607, 551, 543

(56) References Cited

U.S. PATENT DOCUMENTS

| 2,523,692 | 9/1950 | Floyd et al. |  |
| 4,216,218 | 8/1980 | Klioze et al. | 514/327 |
| 4,652,654 | 3/1987 | Verga et al. | 548/217 |
| 5,098,819 | * 3/1992 | Knapp | 430/436 |
| 5,330,888 | 7/1994 | Morigaki et al. | 430/551 |
| 6,068,969 | * 5/2000 | Mikoshiba et al. | 430/607 |

FOREIGN PATENT DOCUMENTS

| 617322A1 | 9/1994 | (EP) | G03C/1/005 |

OTHER PUBLICATIONS

J. M. Bessiere et al., Journal of Fluorine Chemistry, 56 (3) pp. 295–303 (Mar. 1992).
J. Chem. Soc., p. 3160–3161 (1961).
J. Org. Chem., vol. 42, p. 1180–1185 (1977).
Helv. Chim. Acta., 30, pp. 1349–1373 (1947).

* cited by examiner

Primary Examiner—Geraldine Letscher

(57) ABSTRACT

There is disclosed a silver halide color photographic light-sensitive material that is improved in such aspects as fastness of dye images, color reproduction, cyan stain, processing cyan color contamination, and the like, by the combination use of a phenidone compound having a specific structure as in the following general formula (VIII) and a pyrrolotriazole cyan coupler. The phenidone compound (VIII) can be produced industrially in low cost, by reacting an α-alkyl or alkenyl acrylate with a compound represented by the following general formula (VII):

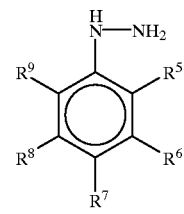

(VII)

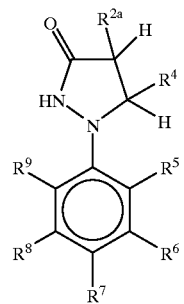

(VIII)

wherein, $R^4$, $R^5$, $R^6$, $R^7$, $R^8$, and $R^9$, each represent a hydrogen atom, an alkyl group, or the like; $R^{2a}$ represents an alkyl group having 6 to 30 carbon atoms, or the like.

10 Claims, No Drawings

US 6,258,521 B1

SILVER HALIDE COLOR PHOTOGRAPHIC LIGHT-SENSITIVE MATERIAL, PHENIDONE COMPOUND FOR USE THEREIN, AND METHOD OF PRODUCING THE SAME

This is a continuation-in-part application of PCT application PCT/JP98/00432 filed on Feb. 2, 1998, the contents of which are herein incorporated by reference.

TECHNICAL FIELD

The present invention relates to a silver halide color photographic light-sensitive material that is improved in such aspects as fastness of dye images, color reproduction, cyan stain, processing cyan color contamination, and the like, by the combination use of a phenidone compound having a specific structure and a pyrrolotriazole cyan coupler.

The present invention relates to a method of synthesizing, inexpensively and easily, α-alkyl or alkenyl acrylates that are useful as a synthetic intermediate of phenidone compounds and the like that is useful as a photographic additive that includes silver halide color photographic light-sensitive materials as described above and the like. The invention also relates to an inexpensive, easy method of synthesizing phenidones using α-alkyl or alkenyl acrylates, and particularly to a method of synthesizing α-alkyl acrylates whose alkyl chain is a long-chain alkyl group. Parenthetically, in the specification of the present application, as a matter of convenience, "α-alkyl or alkenyl" is referred to as "α-alkyl" hereinafter.

BACKGROUND ART

In silver halide color photographic light-sensitive materials, it is well known that, with an exposed silver halide serving as an oxidizer, an oxidized aromatic primary amine-series color-developing agent and a coupler are reacted to produce a dye, such as indophenol, indoaniline, indamine, azomethine, phenoxazine, and phenazine, to form an image. In this photographic system, the subtractive color process is used, wherein a color image is formed by yellow, magenta, and cyan dyes.

In order to form a cyan dye image out of these, conventionally, use is made of phenol- or naphthol-series couplers. Since the dyes formed from these couplers have, however, unpreferable absorption in the region from yellow to magenta, they have a problem of making the color reproduction deteriorated, which is earnestly desired to be solved.

As means for solving this problem, heterocyclic compounds described, for example, in U.S. Pat. Nos. 4,728,598, 4,873,183, and EP-A-0249453 (A2) are proposed. However, these couplers have fatal defects in that, for example, they are low in coupling activity and poor in fastness of dyes.

As couplers that overcome these problems, pyrrolotriazole couplers described in U.S. Pat. No. 5,256,526 and EP-0 545 300 are proposed. These couplers are excellent in hue and coupling activity. However, the fastness of the produced dye images is not necessarily satisfactory, and particularly the fastness to light at the area having a low color density is poorer than that of the conventional couplers, and therefore improvement was desired. Further, desirably the whiteness in the white background after the passage of time should be much higher.

Further, since pyrrolotriazole couplers are high in the molecular extinction coefficient of the dyes produced by the reaction with p-phenylenediamine-series color-developing agents, they have the defect that the so-called processing color contamination is high; that is, the oxidized product of the developing agent produced as a result of the silver development in another layer diffused into the red-sensitive layer and reacted with the cyan coupler in the red-sensitive layer, to increase the cyan density.

Further, since pyrrolotriazole couplers are high in the extinction coefficient of the produced dyes, they have the defect that various cyan stains became high due to the reaction of the color-developing agent remaining in the film with the coupler in or after the step of the color-development step at the time of the processing or during the passage of time after the processing.

JP-A-5-150423 ("JP-A" means unexamined published Japanese patent application) describes that the use of a combination of a nitrogen-containing compound, such as a phenidone compound, with a pyrrolotriazole coupler improves color reproduction and fastness. The effect, however, was not satisfactory.

JP-A-6-324446 describes a method of processing a specific silver halide photographic material comprising a silver chloride emulsion in the presence of a specific 1-phenylpyrazolidine-3-one-series compound to attain photographic properties such as sensitivity and γ by high speed development.

As a method of synthesizing α-alkyl acrylates, a method is known wherein an α-alkyl acrylate is synthesized from an α-halofatty acid ester, zinc, and formaldehyde (J. Chem. Soc., 5562 (1965)). However, since the reaction intermediate is an organometal compound, there are such defects as that the moisture in the solvent lowers the yield and the reaction is difficult to control.

Further, there is known a synthesizing method from a fatty acid ester, a strong base, such as lithium diisopropylamide, and formaldehyde (J. Org. Chem., 37, 1256 (1972)). However, in this method, the reaction has to be carried out at an extremely low temperature of as low as −78° C., and as a result the method has many problems as an industrial synthetic method.

Further, Synthesis, 924 (1982) describes a synthesizing method from a phosphorus ylide and formaldehyde. This method, however, has the problems, for example the yield is low.

On the other hand, J. Chem. Soc., 3160 (1961) describes a method of synthesizing α,β-disubstituted acrylates from an oxalate, a fatty acid ester, benzaldehyde or heptaldehyde. However, the above document does not describe any examples using formaldehyde as the aldehyde.

Further, Helv. Chim. Acta., 1349 (1947) describes a reaction of formaldehyde with an α-alkyl-α-alkoxyoxalyl fatty acid ester, similar to the reaction of the present invention. However, according to the method described in the above document, the reaction product is an α-keto-β-alkoxycarbonyl-γ-lactone, which differs from the present invention. The method described in the document is characterized in that the alkyl group at the α-position of the fatty acid ester compound, the starting material, is a lower alkyl group.

Further, J. Org. Chem., 42, 1180 (1977) describes a reaction similar to the present invention. However, the above document describes, as examples of esters, cyclic esters (lactones) or phenyl acetate only. These tend to form an anion at the α-position of the ester.

It does not suggest the present invention directly because, for example, the stability of the intermediate is different.

Further, J. Organomet. Chem., 177, 67 (1979), Fluorine Chem., 56, 295 (1992), and Helv. Chim. Acta., 30, 1495 (1947) describe methods of producing acrylates, but they do not describe the production method of the present invention.

An object of the present invention is to provide a method of synthesizing α-alkyl acrylates useful as synthetic intermediates for phenidone compounds used in silver halide light-sensitive materials, from inexpensive raw materials, in a high yield, in a short step.

Another object of the present invention is to provide a method of synthesizing α-alkyl acrylates useful as synthetic intermediates for phenidone compounds that are used in silver halide light-sensitive materials, by a series of continuous reactions without taking out intermediates.

Another object of the present invention is to provide novel phenidone compounds that are used in silver halide light-sensitive materials, from inexpensive raw materials, in a short step, in a high yield, and a method of producing them.

Another object of the present invention is to provide a method of synthesizing phenidones that are used in silver halide light-sensitive materials, by a series of continuous reactions without isolating intermediates.

Another object of the present invention is to provide a silver halide color light-sensitive material excellent in color reproduction and improved in storage stability of the light-sensitive material. Another object of the present invention is to provide a silver halide color light-sensitive material reduced in cyan color contamination at the time of processing. Another object of the present invention is to provide a silver halide color light-sensitive material reduced in cyan stain. Another object of the present invention is to provide a silver halide color light-sensitive material excellent in color-forming property and fastness.

DISCLOSURE OF INVENTION

Among the objects of the present invention, the phenidone compounds, and the methods of producing phenidone compounds and their intermediates, have been resolved by the following (1), (2), (3), (4), and (5):

(1) A method of producing a compound represented by general formula (II), comprising reacting a compound represented by general formula (I) with formaldehyde:

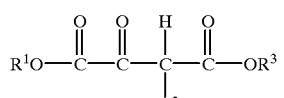

(I)

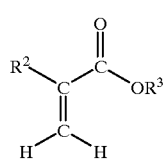

(II)

wherein $R^1$ and $R^3$ each represent an alkyl group having 1 to 30 carbon atoms, and $R^2$ represents an alkyl group having 6 to 30 carbon atoms, or an alkenyl group having 5 to 30 carbon atoms.

(2) A method of producing a compound represented by general formula (II), comprising condensing a compound represented by general formula (III) and a compound represented by general formula (IV) under basic conditions, to synthesize a compound represented by general formula (I), and then reacting the resulting compound with formaldehyde:

(III)

(IV)

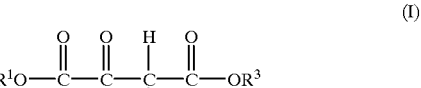

(I)

(II)

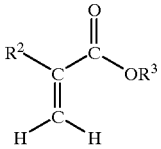

wherein $R^1$, $R^2$, and $R^3$ have the same meanings as $R^1$, $R^2$, and $R^3$ in the above (1).

(3) A method of producing a compound represented by general formula (II) as stated in (2), wherein the compound represented by general formula (III) and the compound represented by general formula (IV) are added, dropwise, simultaneously into the reaction system having basic conditions.

(4) A method of producing a compound represented by general formula (VIII), comprising condensing a compound represented by general formula (III) and a compound represented by general formula (IVa) under basic conditions, to synthesize a compound represented by general formula (Ia), reacting the resulting compound, without isolating the said resulting compound, with a compound represented by general formula (V), to synthesize a compound represented by general formula (VI), and reacting the compound (VI), without isolating the compound (VI), with a compound represented by general formula (VII), to produce a compound represented by general formula (VIII):

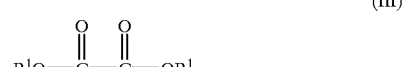

(III)

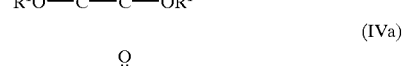

(IVa)

(V)

(VI)

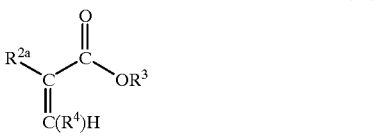

-continued (VII)

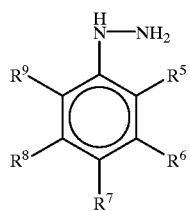

(VIII)

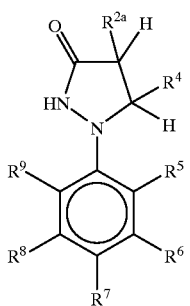

(Ia)

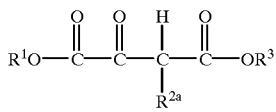

wherein $R^1$ and $R^3$ have the same meanings as $R^1$ and $R^3$ in the above (1); $R^4$ represents a hydorgen atom, an alkyl group having 1 to 30 carbon atoms, or an aryl group having 6 to 20 carbon atoms, and $R^{2a}$ represents an alkyl group having 1 to 30 carbon atoms, or an alkenyl group having 2 to 30 carbon atoms;

$R^5$, $R^6$, $R^7$, $R^8$, and $R^9$, which are the same or different independently, each represent a hydrogen atom, an alkyl group, an aryl group, an alkoxy group, an aryloxy group, an unsubstituted amino group, an alkylamino group, an arylamino group, an acylamino group, an aminocarbonylamino group, an alkoxycarbonylamino group, an arylcarbonylamino group, an alkoxycarbonyl group, an aryloxycarbonyl group, a sulfonyl group, a sulfonylamino group, a nitro group, a halogen atom, a hydroxy group, a carboxyl group, a heterocyclic group, a sulfamoyl group, a carbamoyl group, an azo group, an alkylthio group, an arylthio group, an imido group, a sulfinyl group, a phosphonyl group, or an acyl group; $R^{2a}$ and $R^4$ in general formula (VIII) have the same meanings as $R^{2a}$ of general formula (IVa) and $R^4$ of general formula (V).

(5) A compound represented by the following general formula (IXa):

(IXa)

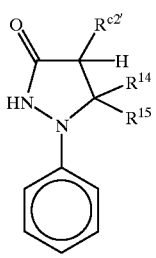

$R^{c2'}$ represents an alkyl group having 12 to 30 carbon atoms (preferably 14 to 28 carbon atoms, and more preferably 16 to 26 carbon atoms); $R^{14}$ and $R^{15}$ each independently represent a hydrogen atom, an alkyl group having 1 to 20 carbon atoms, or an aryl group having 6 to 20 carbon atoms.

As for the light-sensitive material among the above objects of the invention, combinations of pyrrolotriazole couplers with various compounds have been studied, and it has been found that the above object can be attained by using, out of phenidone compounds, particularly a compound represented by general formula (B) or (C).

That is, the present invention is a silver halide color photographic light-sensitive material having at least one silver halide emulsion layer on a base, wherein at least one of cyan couplers represented by general formula (A), and at least one compound selected from among compounds represented by the following general formula (B) or (C), are contained in at least one layer of a silver halide emulsion;

(A)

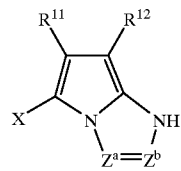

(B)

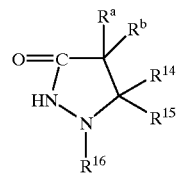

(C)

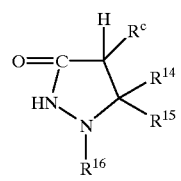

wherein, in formula (A), $Z^a$ and $Z^b$ each represent —C($R^{13}$)= or —N=, provided that one of $Z^a$ and $Z^b$ is —N= and the other is —C($R^{13}$)=; $R^{11}$ and $R^{12}$ each represent an electron-attracting group whose Hamnett substituent constant $\sigma_p$ value is 0.20 or more; and the "wa" of the $\sigma_p$ values of $R^{11}$ and $R^{12}$ is 0.65 or more; $R^{13}$ represents a hydrogen atom or a substituent; X represents a hydrogen atom, or α-group capable of being released upon the coupling reaction with the oxidized product of an aromatic primary amine color-developing agent; or the group of $R^{11}$, $R^{12}$, $R^{13}$, or X may be a divalent group, to form a dimer or higher polymer, or to bond to a polymer chain, to form a homopolymer or a copolymer;

in formula (B), $R^a$ and $R^b$ each independently represent an aryl group, or an alkyl group having 2 to 30 carbon atoms in all, including the number of carbon atoms in the substituents; $R^{14}$ and $R^{15}$ represent a hydrogen atom, an alkyl group, or an aryl group; $R^{16}$ represents an aryl group;

in formula (C), $R^{14}$, $R^{15}$, and $R^{16}$ each independently have the same meaning as in (B); and $R^c$ represents an alkyl group or an aryl group.

Further, the object of the present invention is attained by the following light-sensitive material:

A silver halide color photographic light-sensitive material, containing at least one compound represented by the following general formula (IX) in any one of photographic constitutional layers on a base:

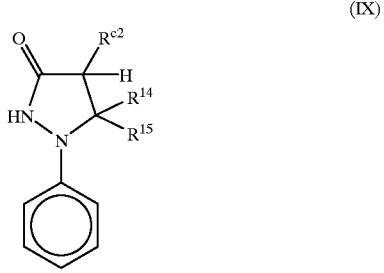

(IX)

wherein, in formula (IX), $R^{c2}$ represents an alkyl group having 12 to 30 carbon atoms (preferably 14 to 28 carbon atoms, and more preferably 16 to 26 carbon atoms), or an alkenyl group having 12 to 30 carbon atoms (preferably 14 to 28 carbon atoms, and more preferably 16 to 26 carbon atoms), and $R^{14}$ and $R^{15}$, which are the same or different, each independently represent a hydrogen atom, an alkyl group having 1 to 20 carbon atoms, or an aryl group having 6 to 20 carbon atoms.

In this specification and in the claims, the groups defined in general formulas (I) to (IX), (IXa), (IVa), (A), (B), and (C) mean to include cases in which they have a substituent(s). Further, the number of carbon atoms in a group means the total number of carbon atoms including those of the substituent(s) on the group.

BEST MODE FOR CARRYING OUT THE INVENTION

First, the method of producing compounds is described.

The α-alkyl acrylates represented by general formula (II) that is produced by the production method of the present invention is described in detail.

In general formula (II), the alkyl group represented by $R^2$ is preferably a substituted or unsubstituted alkyl group having 1 to 30 carbon atoms, more preferably a substituted or unsubstituted alkyl group having 14 to 26 carbon atoms, and most preferably a substituted or unsubstituted alkyl group having 16 to 22 carbon atoms.

Examples of the unsubstituted alkyl group include n-hexyl, n-heptyl, n-octyl, n-nonyl, n-decyl, n-dodecyl, n-tetradecyl, n-hexadecyl, n-octadecyl, n-eicosyl, n-tetraeicosyl, isopentyl, isohexyl, isoheptyl, isooctyl, isononyl, isodecyl, isododecyl, isotetradecyl, isohexadecyl, isooctadecyl, isoeicosyl, isotetraeicosyl, and isooctaeicosyl.

As the substituent that may substitute on the alkyl group, can be mentioned an aryl group, a heterocyclic group, a halogen atom, an alkoxy group, an aryloxy group, an alkylthio group, an arylthio group, a cyano group, a nitro group, an alkoxycarbonyl group, an aryloxycarbonyl group, a carboxyl group, a sulfo group, a sulfamoyl group, a carbamoyl group, an azo group, an alkylsulfinyl group, an arylsulfinyl group, an imido group, a phosphonyl group, an unsubstituted amino group, an alkylamino group, an arylamino group, an aminocarbonylamino group, an alkoxycarbonylamino group, a hydroxyl group, an acyl group, an acyloxy group, an alkylsulfonyl group, an arylsulfonyl group, an acylamino group, an arylsulfonamido group, and an alkylsulfonamido group.

As examples thereof, can be mentioned a phenyl group, a naphthyl group, a tetrahydrofuryl group, an α-pyridyl group, a fluorine atom, a methoxy group, an ethoxy group, a phenoxy group, a methylthio group, a phenylthio group, a cyano group, a nitro group, a methoxycarbonyl group, an octyloxycarbonyl group, a phenoxycarbonyl group, a carboxyl group, a sulfo group, a dimethylsulfamoyl group, a diethylsulfamoyl group, a diethylcarbamoyl group, an azo group, a methanesulfinyl group, a benzenesulfinyl group, a phthalimido group, an ethylphosphonyl group, a dimethylamino group, an anilino group, a dimethylaminocarbonylamino group, a methoxycarbonylamino group, a hydroxy group, a benzoyl group, a pivaloyl group, an acetyloxy group, a methanesulfonyl group, a toluenesulfonyl group, an acetylamino group, a toluenesulfonylamino group, and a methanesulfonylamino group.

When $R^2$ is an alkyl group, preference is given to an unsubstituted alkyl group over those substituted.

When $R^2$ represents an alkenyl group, preference is given to a substituted or unsubstituted alkenyl group having 10 to 30 carbon atoms, more preferably a substituted or unsubstituted alkenyl group having 14 to 26 carbon atoms, and most preferably a substituted or unsubstituted alkenyl group having 16 to 22 carbon atoms.

As examples of the alkenyl group, can be mentioned 3-pentenyl, 3-hexenyl, 4-heptenyl, 5-octenyl, 4-nonenyl, 5-decenyl, 6-dodecenyl, 3-tetradecenyl, 7-hexadecenyl, 8-octadecenyl, 6-eicocenyl, and 10-tetraeicocenyl.

As examples of the substituent that may substitute on the alkenyl group, can be mentioned those substituents of the substituted alkyl group represented by $R^2$.

In general formula (II), $R^3$ represents preferably a substituted or unsubstituted alkyl group having 1 to 10 carbon atoms, and more preferably a substituted or unsubstituted alkyl group having 1 or 2 carbon atoms. As for $R^3$, preference is given to those unsubstituted over those substituted.

As examples of $R^3$, can be mentioned methyl, ethyl, n-propyl, isopropyl, n-octyl, and n-octadecyl. $R^3$ is preferably methyl or ethyl. $R^3$ is most preferably a methyl group.

The above description is similarly applied to the compound represented by general formula (VI), the description of $R^2$ is applied all to $R^{2a}$, and the description of the substituents of $R^2$ is applied to the case in which $R^4$ group has a substituent(s). Specific examples of $R^4$ are preferably those described for $R^{14}$ in the below-described formula (B).

The compound represented by general formula (I) that is a raw material for the synthesis reaction is described. In the formula, $R^1$ is a substituted or unsubstituted alkyl group having 1 to 30 carbon atoms. Preferably $R^1$ is a substituted or unsubstituted alkyl group having 1 to 10 carbon atoms, and more preferably a substituted or unsubstituted alkyl group having 1 or 2 carbon atoms. As for $R^1$, preference is given to those unsubstituted over those substituted.

As examples of $R^1$, can be mentioned methyl, ethyl, n-propyl, isopropyl, n-octyl, and n-octadecyl. $R^1$ is preferably methyl or ethyl. $R^1$ is most preferably a methyl group.

Preferably $R^1$ and $R^3$ in formula (I) are the same.

Examples of the compound represented by general formula (II) that can be synthesized by the synthetic method of the present invention are shown below:

1. 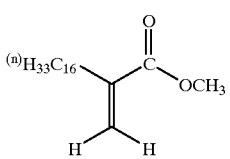
2. 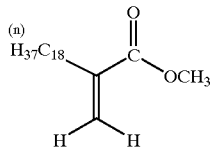
3. 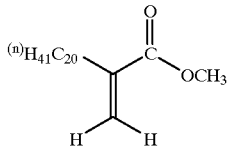
4. 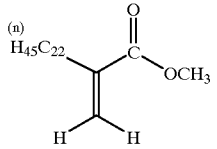
5. 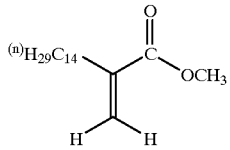
6. 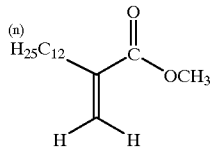
7. 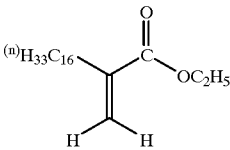
8. 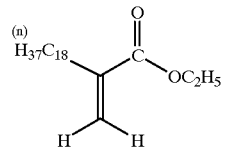
9. 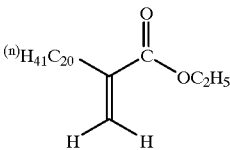
-continued
10. 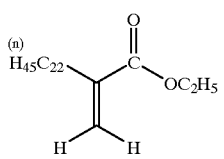
11. 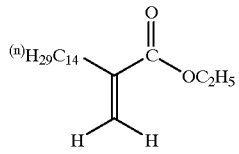
12. 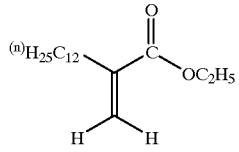
13. 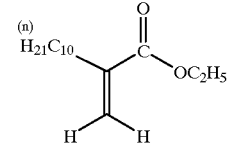
14. 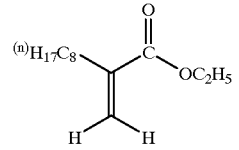
15. 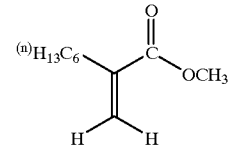
16. 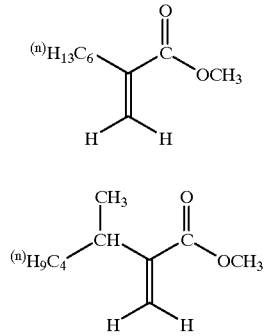
17. 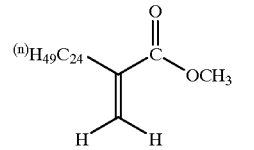
18. 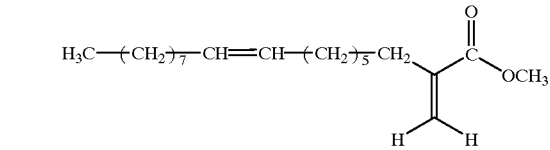

19.
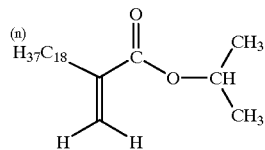

20.
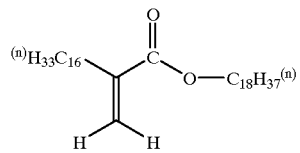

21.
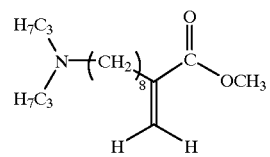

22.
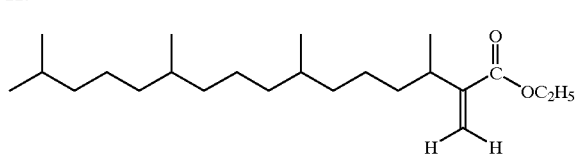

23.
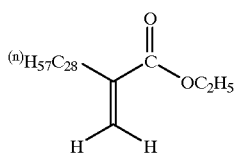

24.
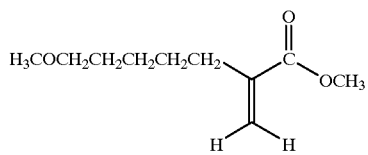

25.
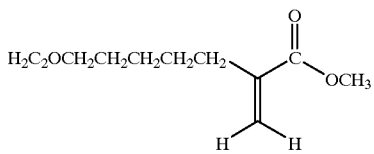

26.
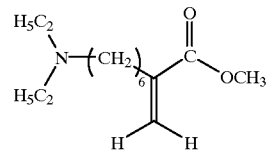

27.
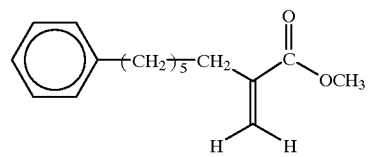

This reaction is described in detail. This reaction is a reaction wherein a compound represented by general formula (I) is reacted with formaldehyde, to synthesize a compound (II). The number of moles of formaldehyde to be used per mol of the compound of general formula (I) is generally from 0.5 to 10, preferably from 0.5 to 3, and more preferably from 1 to 1.3.

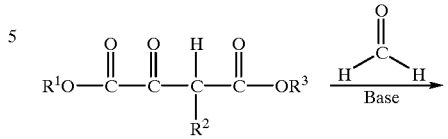

(I)

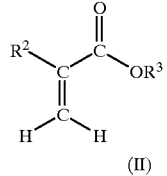

(II)

The reaction of this synthesis may or may not use any solvent, but preferably it uses a solvent in view of stirrability of the reaction solution. As the solvent, any solvent that does not react with the compound represented by general formula (I) can be used. For example, an alcohol-series solvent (methanol, ethanol, n-butanol, t-butanol, isopropanol, glycol, glycerin, MFG, and methyl cellosolve), an ester-series solvent (ethyl acetate, butyl acetate, and methyl propionate), a halogen-series solvent (carbon tetrachloride, chloroform, methylene chloride, trichloroethane, and chlorobenzene), an amide-sries solvent (dimethylformamide and dimethylacetamide), an aromatic-series solvent (benzene, toluene, and xylene), an alkane-series solvent (hexane, pentane, and petroleum ether), an ether-series solvent (diethyl ether, dibutyl ether, and tetrahydrofuran), acetonitrile, water, etc. can be mentioned as examples.

Methanol and ethanol are preferable.

Formaldehyde for use in the reaction is described. As the formaldehyde, gaseous formaldehyde may be used, and paraformaldehyde, formalin (an aqueous solution of formaldehyde), trioxane or the like may be used as a source of formaldehyde. Formalin is preferable.

As the base for use in the reaction, any base can be used that can pull a hydrogen atom of the compound of general formula (I), to produce an enolate. For example, a metal hydroxide, such as sodium hydroxide and potassium hydroxide; a metal hydride, such as sodium hydride and potassium hydride; a metal alcoholate, such as sodium methylate and sodium ethylate; a metal amide, such as sodium amide and lithium diisobutylamide, other organic bases, and the like can be used.

Further, the enolate of the compound of general formula (I) from which a hydrogen atom has been previously pulled may be used. Particularly, in the case in which the compound of general formula (I) is obtained in an enolate form when the compound of general formula (I) is synthesized, preferably the compound is used as it is.

The equivalent of the base is preferably 0.1 to 10 equivalents, more preferably 1 to 3 equivalents, and most preferably 1 to 1.3 equivalents, to the compound of general formula (I).

The reaction temperature can be selected in the range of $-20°$ C. to $180°$ C., and preferably it is from $0°$ C. to $100°$ C. and more preferably from $20°$ C. to $60°$ C.

The reaction time is from 5 min to 50 hours, preferably 20 min to 3 hours, and more preferably 30 min to 2 hours.

The reaction concentration of the compound of general formula (I) can be selected in the range from the neat compound (containing no solvent) to 0.001 mol/liter, and preferably the reaction concentration is from the neat compound to 0.01 mol/liter, and more preferably from 5 mol/liter to 0.1 mol/liter.

Next, the method of synthesizing the compound of general formula (I) is described.

The compound of general formula (I) is preferably synthesized by condensing a compound represented by general formula (III) with a compound represented by general formula (IV) under basic conditions, in view of the cost of raw materials. The molar ratio between the compound of general formula (III) and the compound of general formula (IV) to be used is preferably from 2:1 to 1:2, and more preferably from 1.2:1 to 1:1.

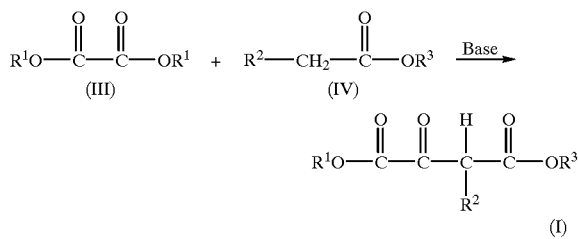

The base to be used in this reaction may be any one that can pull a hydrogen atom of the compound represented by general formula (IV). For example, a metal hydride, such as sodium hydride and potassium hydride; a metal alcoholate, such as sodium methylate and sodium ethylate; a metal amide, such as sodium amide and lithium diisobutylamide, and the like can be used. In view of cost, a metal alcoholate is preferably used.

Further, the enolate of the compound of general formula (IV) from which a hydrogen atom has previously been pulled may be used.

The equivalent of the base is preferably 0.1 to 10 equivalents, more preferably 1 to 3 equivalents, and most preferably 1 to 1.3 equivalents, to the compound of general formula (IV).

In this reaction, a solvent may or may not be used. The solvent to used is preferably one that does not react with the base, and, for example, an aromatic-series solvent (benzene, toluene, and xylene), an alkane-series solvent (octane and the like), an ether-series solvent (dibutyl ether), and the like are preferable.

This reaction produces, as a by-product, an alcohol along with the progress of the reaction, thereby lowering the reaction rate. Therefore, to complete the reaction, it is required to remove the alcohol. As the method for removing the alcohol, a method in which the alcohol is distilled off under normal pressures or reduced pressure is preferable.

The reaction temperature is preferably 50° C. to 200° C., and more preferably 80° C to 150° C., when a metal alcoholate is used as the base. When a metal amide is used as the base, the reaction temperature is preferably −100° C. to 0° C.

The concentration of the compound of general formula (IV) in the reaction liquid is preferably from the neat compound (containing no solvent) to 0.001 mol/liter, and more preferably from the neat compound to 0.1 mol/liter.

Preferably the reaction time is 10 min to 24 hours, and more preferably 1 hour to 6 hours.

When the compound of general formula (III) and the compound of general formula (IV) are reacted by charging them all at once (their entire quantities), the reaction proceeds rapidly and control of the reaction is difficult. To carry out the synthesis in quantity, it is important to control the reaction as described below.

To control the reaction, there is a method in which the compound of general formula (III) is charged previously into the reaction system (reaction vessel) and then the compound of general formula (IV) is added dropwise, but the yield is considerably lower compared with when they are charged all at once.

To control the reaction, a method in which the compound of general formula (III) and the compound of general formula (IV) are added, dropwise, simultaneously into a reaction vessel, which is made basic, is more preferable. In this case, the yield is not considerably lower compared with when they are charged all at once. herein, "to charge them simultaneously" means the case wherein both are mixed and charged, as well as the case wherein they are charged, simultaneously but separately.

The method of synthesizing phenidones of the present invention is described. The phenidones are synthesized by the following synthetic method.

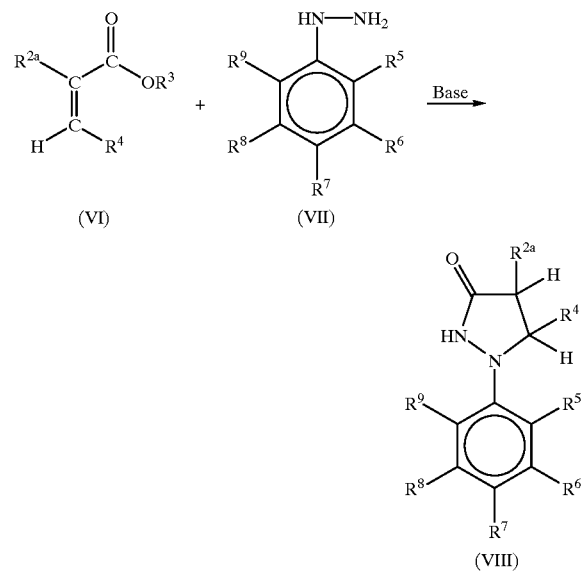

As $R^{2a}$ in general formula (VI), one described for $R^2$ of general formula (II) is applied.

The method of synthesizing phenidones represented by general formula (VIII) of the present invention is a method wherein a compound represented by general formula (VI), synthesized by the method of synthesizing a compound of the above general formula (II), is condensed with a hydrazine compound represented by general formula (VII), under basic conditions. It is characterized in that, at that time, the compound represented by general formula (VI) is reacted with the compound of (VII), without isolating the compound represented by general formula (VI). The molar ratio between the compound of general formula (VI) and the compound of general formula (VII) to be used is preferably from 3:1 to 1:3, and more preferably from 1:1.3 to 1:1.

The compounds represented by formula (IX) or (IXa) can be synthesized in accordance with the method of synthesizing the compound represented by formula (VIII).

Examples of the phenidone compound that can be synthesized by the present invention are shown below.

Ph-(1)
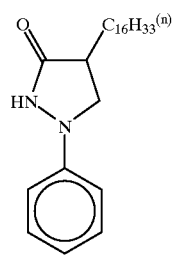
Ph-(2)
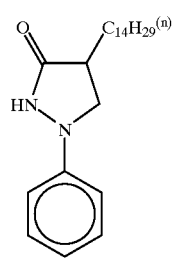
Ph-(3)
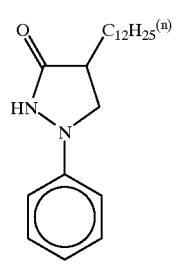
Ph-(4)
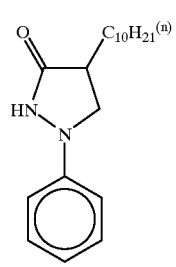
Ph-(5)
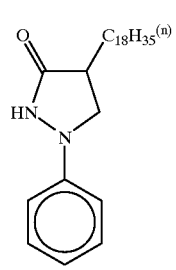
Ph-(6)
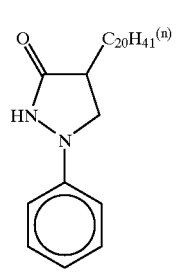
-continued
Ph-(7)
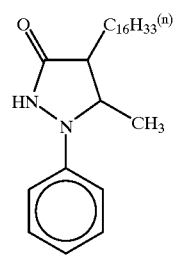
Ph-(8)
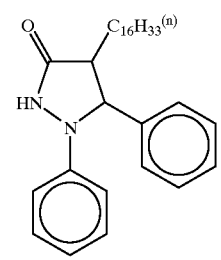
Ph-(9)
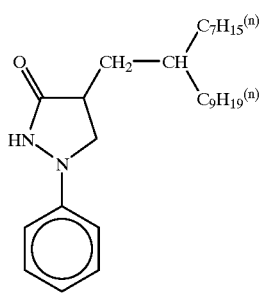
Ph-(10)
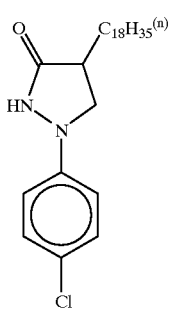
Ph-(11)
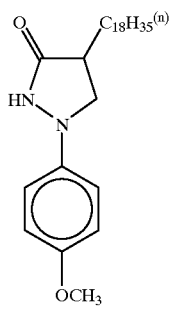

-continued

Ph-(12)

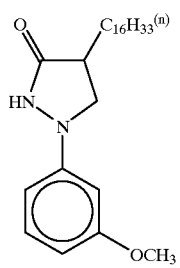

Ph-(13)

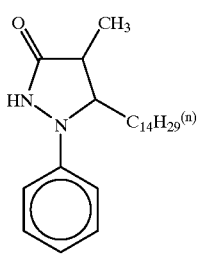

Ph-(14)

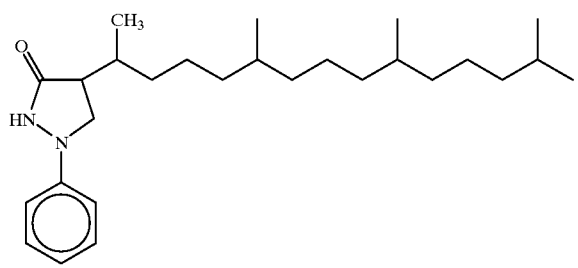

Ph-(15)

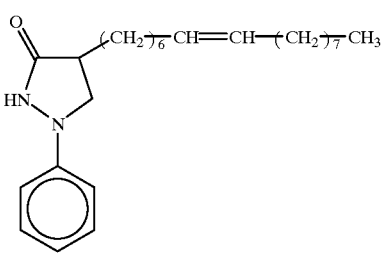

Ph-(16)

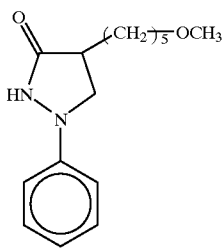

As the base used in this reaction, a metal alkoxide (t-butoxy potassium, sodium methoxide, and sodium ethoxide), a metal hydride (potassium hydride and sodium hydride), and a metal amide (sodium amide and lithium diisopropylamide) are preferable. The amount of the base to be used is preferably 0.1 to 10 equivalents, and more preferably 1 to 1.5 equivalents.

When the hydrazine compound used in the present invention is available in the free state, it can be used as it is. When it is available in the form of a base, it is used after making it once in the free state or by making it in the free state in the reaction system.

When a base of hydrazine is used as the hydrazine compound, preferably one equivalent of an additional base is added in order to make the hydrazine free.

The reaction solvent is preferably an aromatic-series solvent (benzene, toluene, and xylene), an At alcohol-series solvent (n-butanol and n-octanol), or an alkane-series solvent (octane and petroleum ether).

The reaction temperature is preferably −20° C. to 180° C., more preferably 0° C. to 140° C., and further preferably 40° C. to 100° C.

The reaction concentration of the compound of general formula (VI) is from the neat compound (containing no solvent) to 0.001 mol/liter, and more preferably 2 mol/liter to 0.01 mol/liter.

Under basic conditions, the produced phenidones are oxidized and decomposed with oxygen in air. To obviate this, the reaction system is preferably purged or flowed with an inert gas, such as nitrogen gas and argon gas.

Further, a radical inhibitor, such as BHT, may be added in a small amount. The amount of the radical inhibitor to be added is preferably 0.001 mol/liter to 0.1 mol/liter, and more preferably 0.01 mol/liter to 0.05 mol/liter of the phenylhydrazine.

The present invention is described in detail with reference to Synthetic Examples.

Synthetic Example 1

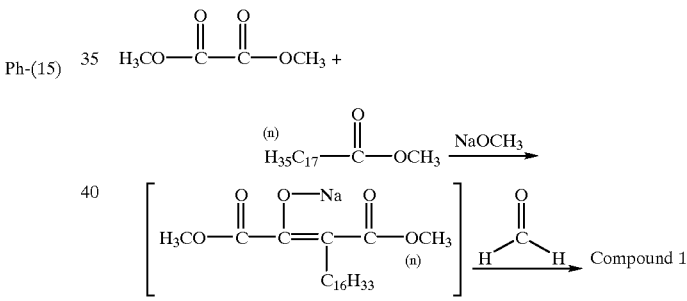

10.28 g (87.1 mmol) of methyl oxalate, 4.95 g (87.1 mmol) of sodium methylate, 20.0 g (67.0 mmol) of methyl stearate, and 50 ml of toluene were placed in a three-necked flask and were heated in an oil bath. They were reacted for 2 hours under normal pressures, while toluene was distilled off. The reaction temperature reached 130° C., finally. Thereafter, the toluene was distilled off under reduced pressure, and the reaction was continued at 130° C. for 30 min. It was cooled to 60° C., and then a solution containing 7.06 g (87.1 mmol) of 37% formalin in 50 ml of methanol was added, dropwise. After reaction was carried out at 60° C. for 30 min, 20 ml of ethyl acetate and 200 ml of 1N hydrochloric acid were added and extraction was carried out. After the organic layer was washed with water once, it was washed with an aqueous sodium bicarbonate solution. After drying, the solvent was concentrated in an evaporator under reduced pressure, to obtain a crude product. It was purified by silica gel column chromatography (hexane/ethyl acetate= 10/1), to obtain 23.0 g (74.04 mmol) of Compound 1 (yield 85.0%). The structure of the product was identified by mass spectrum and NMR at 300 MHz.

Comparative Example 1
(A Synthetic Method in Accordance with Nihon Kagaku Zasshi, 80.502 (1959))

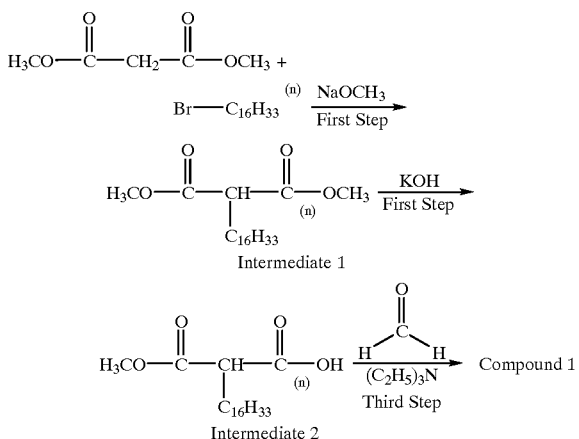

[First Step]

While 25.6 g (194 mmol) of dimethyl malonate, 80 ml of methanol, and 37.5 g (194 mmol) of a methanol solution of sodium methoxide (28%) were stirred at room temperature, 59.2 g (194 mmol) of 1-bromohexadecane was added, dropwise, thereto. After refluxing for 3 hours, the solvent was distilled off, and 100 ml of 1N hydrochloric acid and 100 ml of hexane were added, to carry out extraction. After the organic layer was washed with a saturated brine, the solvent was distilled off under reduced pressure. 51.1 g (143 mmol) of an oil of an intermediate was obtained (the yield: 73.7%).

[Second Step]

51.1 g (143 mmol) of Intermediate 1, 80 ml of methanol, and 9.46 g (143 mmol) of 85% potassium hydroxide were stirred at 40° C. for 2 hours. With cooling with ice, 13 ml of concentrated hydrochloric acid and 50 ml of water were added, dropwise, at a temperature of 10° C. The deposited crystals were collected by filtering; they were washed with 200 ml of water and 100 ml of hexane, and were dried, to obtain 46.5 g (136 mmol) of Intermediate 2 (the yield: 95%).

[Third Step]

While 46.5 g (136 mmol) of Intermediate 2, 100 ml of methanol, and 1.5 g (157 mmol) of triethylamine were stirred at 20° C., 13.5 g (157 mmol) of a 35% aqueous formalin solution were added, dropwise, thereto. After reaction was carried out at room temperature for 24 hours, the deposited crystals were collected by filtering; they were washed with 100 ml of water and 100 ml of methanol, and were dried, to obtain 39.6 g (128 mmol) of Compound 1 (the yield: 94.1%) (the total yield from the first step to the third step: 65.9%).

By comparing Example 1 to Comparative Example 1, it can be understood that the synthetic method of the present invention is excellent, since the synthesis is carried out using inexpensive raw materials, the reactions are simple, the reaction time is quite short, and the yield is high.

Synthetic Example 2

29.0 g of sodium methoxide and 100 ml of toluene were placed in a three-necked flask and were heated in an oil bath at 60° C., and to the resulting solution, a mixture of 54.0 g of diethyl oxalate, 44.0 g of methyl stearate, and 120 ml of toluene was added, dropwise, over 30 min. While reaction was carried out for 90 min, 75 ml of a mixture of ethanol and the solvent was distilled off under reduced pressure. After cooling to 10° C., 110 ml of methanol was added, and then a mixture of 30.6 g of 37% formalin and 10 ml of methanol was added, dropwise, over 10 min. After reaction was carried out for 30 min, 270 ml of ethyl acetate and 180 ml of water were added, to carry out extraction, and the organic layer was washed with 260 ml of diluted hydrochloric acid (1N) and then with water at 50° C.

The organic layer was concentrated under reduced pressure and was purified by silica gel column chromatography (hexane:ethyl acetate=10:1), to obtain 39.3 g of Compound 1 (the yield: 86.0%).

Comparative Example 2

Using the same amounts of the reagents as in Synthesis Example 2, the procedure was carried out in the same manner as Synthesis Example 2, except that, while the dimethyl oxalate, the sodium methoxide, and the toluene were heated, the mixture of methyl stearate and toluene was added thereto, dropwise. The dropping time was 30 min. Since the dimethyl oxalate was decomposed under the basic conditions, the yield was reduced.

As a result, 26.5 g of Compound 1 was obtained (the yield: 58.0%).

Synthetic Example 3

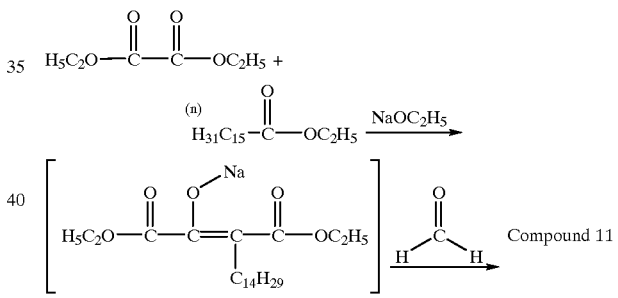

The reaction was carried out in the same manner as in Synthesis Example 1, with the raw materials used being as shown below. As a result, 24.0 g (72.0 mmol) of Compound 11 was obtained (the yield: 78%).

| | |
|---|---|
| Diethyl oxalate | 15.0 g |
| Sodium ethylate | 7.68 g |
| Ethyl hexadecanate | 26.26 g |
| Paraformaldehyde (the content: 80%) | 5.75 g |

Synthetic Example 4

The present invention is described in detail by showing an example for synthesizing a phenidone compound by reacting the compound of general formula (II) continuously without producing it in the isolated state.

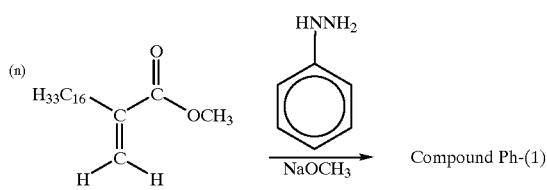

Compound 1 was synthesized according to Synthetic Example 1, except for using 100 ml of toluene, 100 ml of hexane, and 1N hydrochloric acid for the extraction after the reaction. After the organic layer was washed with water once, and then with 100 ml of an aqueous sodium bicarbonate solution, the solvent was distilled off. When the temperature reached 100° C., the distillation-off was stopped, and cooling was carried out, to use it for the phenidone synthesis. At this point, analysis was carried out with HPLC. As a result, it was found that the ethyl hexadecanoate did not remain. Few other by-products were found and the purity was 98%.

While 7.25 g (67.0 mmol) of phenylhydrazine and 4.20 g (73.7 mmol) of sodium methoxide were stirred at 100° C., a toluene solution of the above Compound 1 (74.03 mmol) was added, dropwise, thereto. After reaction was carried out at 100° C. for 30 min, 200 ml of 1N hydrochloric acid and 200 ml of ethyl acetate were added, to carry out extraction, and after the organic layer was washed with water, the solvent was distilled off under reduced pressure. 100 ml of hexane was added, to carry out recrystallization, to obtain 15.1 g of Compound Ph-(1) (the yield: 58.3%).

As is described above, it can be understood that, since the purity of the α-alkyl acrylate synthesized by the present synthetic method is high, even if it is used in the reaction in the subsequent step in the form of a solution without isolating and purifying it, it does not adversely affect the reaction.

Comparative Example 2

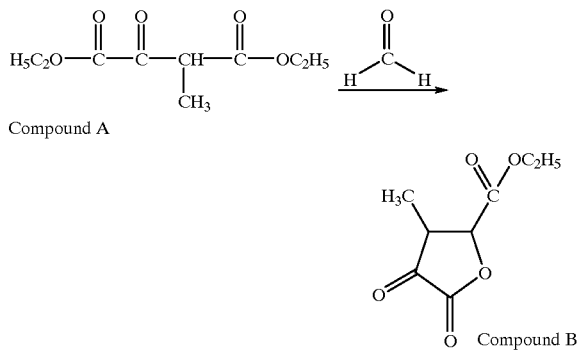

70.7 g (350 mol) of Compound A was dispersed in 200 ml of water, and then 81.1 g (1 mol) of formalin (37%) and 24.2 g (175 mmol) of potassium carbonate were added at 20° C. After reacting for 2 hours, extraction with ethyl acetate was carried out, and the solvent was distilled off under reduced pressure. Purification was carried out by silica gel column chromatography, to obtain 59 g (317 mmol) of Compound B (the yield: 90%).

As is described above, when $R^2$ of general formula (I) is a methyl group, a lactone product was given as a main product, which differed from the reaction of the present invention.

Now, the silver halide color photographic light-sensitive material of the present invention is described.

First, the Hammett substituent constant $\sigma_p$ value used in the present specification is described a little. The Hammett rule is an empirical rule suggested by L. P. Hammett in 1935 in order to deal quantitatively with the influence of substituents on reactions or equilibria of benzene derivatives, and nowadays its validity is widely accepted. The substituent constants determined by the Hammett rule include $\sigma_p$ values and $\sigma_m$ values, many of which are described in general books and are described in detail, for example, edited by J. A. Dean in "Lange's Handbook of Chemistry," 12th edition, 1979 (McGraw-Hill), and in "Kagaku no Ryoiki" Zokan, No. 122, pages 96 to 103, 1979 (Nanko-do). In the present invention, substituents are stipulated or explained by the Hammett substituent constant $\sigma_p$ values, but the present invention should, of course, not be construed as being limited to the substituents whose values are known and described in literature in the above books; rather the present invention includes substituents whose Hammett substituent constant $\sigma_p$ values are not known in the literature but will fall within the above range when measured in accordance with the Hammett rule. The compound represented by general formula (I) of the present invention is not a benzene derivative, but, as a scale for indicating the electron effect of the substituent, the $\sigma_p$ value is used irrespective of the substitution position. In the present invention, hereinafter, the $\sigma_p$ value is used in this sense. Further, "lipophilic" referred to in the present invention means that the solubility in water at room temperature is 10% or less.

"Aliphatic" in this specification may be one that is straight-chain, branched-chain, or cyclic and may be saturated or unsaturated and, for example, represents alkyl, alkenyl, alkynyl, cycloalkyl, or cycloalkenyl, which may be further substituted. Further, "aromatic" represents aryl, which may be further substituted; and "heterocyclic" means a ring having a hetero atom(s) in the ring, including an aromatic heterocyclic group, which may be further substituted. In this specification, the substituents, and the substituents that may be possessed by these aliphatic, aromatic, and heterocyclic, may be groups that can substitute unless otherwise specified, and examples of these substituents include an aliphatic group, an aromatic group, a heterocyclic group, an acyl group, an acyloxy group, an acylamino group, an aliphatic oxy group, an aromatic oxy group, a heterocyclic oxy group, an aliphatic oxycarbonyl group, an aromatic oxycarbonyl group, a heterocyclic oxycarbonyl group, an aliphatic carbamoyl group, an aromatic carbamoyl group, an aliphatic sulfonyl group, an aromatic sulfonyl group, an aliphatic sulfamoyl group, an aromatic sulfamoyl group, an aliphatic sulfonamido group, an aromatic sulfonamido group, an aliphatic amino group, an aromatic amino group, an aliphatic sulfiniyl group, an aromatic sulfinyl group, an aliphatic thio group, an aromatic thio group, a mercapto group, a hydroxy group, a cyano group, a nitro group, a hydroxyamino group, a halogen atom, and the like.

Hereinbelow the cyan coupler represented by general formula (A) of the present invention is described in detail. $Z^a$ and $Z^b$ each represent —C($R^{13}$)= or —N=, provided that one of $Z^a$ and $Z^b$ is —N= and the other is —C($R^{13}$)=.

$R^{13}$ represents a hydrogen atom or a substituent, and as the substituent, can be mentioned a halogen atom, an alkyl group, a cycloalkyl group, an aryl group, a heterocyclic group, a cyano group, a hydroxy group, a nitro group, a carboxy group, a sulfo group, an amino group, an alkoxy group, an aryloxy group, an acylamino group, an alkylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonylamino group, an imido group, a heterocyclic thio group, a sulfinyl group, a phosphonyl group, an aryloxycarbonyl group, an acyl group, and the like, each of which may further be substituted by the substituent(s) shown by way of example in $R^3$.

More specifically, $R^{13}$ represents a hydrogen atom, a halogen atom (e.g., a chlorine atom and a bromine atom), an alkyl group (e.g., a straight-chain or branched-chain alkyl group, an aralkyl group, an alkenyl group, an alkynyl group, a cycloalkyl group, and a cycloalkenyl group, each having 1 to 32 carbon atoms, and specifically, for example, methyl, ethyl, propyl, isopropyl, t-butyl, tridecyl, 2-methanesulfonylethyl, 3-(3-pentadecylphenoxy)propyl, 3-{4-{2-[4-(4-hydroxyphenylsulfonyl)phenoxy]dodecaneamido}phenyl}propyl, 2-ethoxytridecyl, trifluoromethyl, and 3-(2,4-di-t-amylphenoxy)propyl), an aryl group (e.g., phenyl, 4-t-butylphenyl, 2,4-di-t-amylphenyl, and 4-tetradecaneamidophenyl), a heterocyclic group (e.g., imidazolyl, pyrazolyl, triazolyl, 2-furyl, 2-thienyl, 2-pyrimidinyl, and 2-benzothiazolyl), a cyano group, a hydroxy group, a nitro group, a carboxy group, an amino group, an alkoxy group (e.g., methoxy, ethoxy, 2-methoxyethoxy, 2-dodecylethoxy, and 2-methanesulfonylethoxy), an aryloxy group (e.g., phenoxy, 2-methylphenoxy, 4-t-butylphenoxy, 3-nitrophenoxy, 3-t-butyloxycarbamoylphenoxy, and 3-methoxycarbamoyl), an acylamino group (e.g., acetamido, benzamido, tetradecaneamido, 2-(2,4-di-t-amylphenoxy)butaneamido, 4-(3-t-butyl-4-hydroxyphenoxy)butaneamido, and 2-{4-(4-hydroxyphenylsulfonyl)phenoxy}decaneamido), an alkylamino group (e.g., methylamino, butylamino, dodecylamino, diethylamino, and methylbutylamino), an anilino group (e.g., phenylamino, 2-chloroanilino, 2-chloro-5-tetradecaneaminoanilino, 2-chloro-5-dodecyloxycarbonylanilino, N-acetylanilino, and 2-chloro-5-{2-(3-t-butyl-4-hydroxyphenoxy)dodecaneamido}anilino), a ureido group (e.g., phenylureido, methylureido, and N,N-dibutylureido), a sulfamoylamino group (e.g., N,N-dipropylsulfamoylamino and N-methyl-N-decylsulfamoylamino), an alkylthio group (e.g., methylthio, octylthio, tetradecylthio, 2-phenoxyethylthio, 3-phenoxypropylthio, and 3-(4-t-butylphenoxy)propylthio), an arylthio group (e.g., phenylthio, 2-butoxy-5-t-octylphenylthio, 3-pentadecylphenylthio, 2-carboxyphenylthio, and 4-tetradecaneamidophenylthio), an alkoxycarbonylamino group (e.g., methoxycarbonylamino and tetradecyloxycarbonylamino), a sulfonamido group (e.g., methanesulfonamido, hexadecanesulfonamido, benzenesulfonamido, p-toluenesulfonamido, octadecanesulfonamido, and 2-methoxy-5-t-butylbenzenesulfonamido), a carbamoyl group (e.g., N-ethylcarbamoyl, N,N-dibutylcarbamoyl, N-(2-dodecyloxyethyl)carbamoyl, N-methyl-N-dodecylcarbamoyl, and N-{3-(2,4-di-t-amylphenoxy)propyl}carbamoyl), a sulfamoyl group (e.g., N-ethylsulfamoyl, N,N-dipropylsufamoyl, N-(2-dodecyloxyethyl)sulfamoyl, N-ethyl-N-dodecylsulfamoyl, and N,N-diethylsulfamoyl), a sulfonyl group (e.g., methanesulfonyl, octanesulfonyl, benzenesulfonyl, and toluenesulfonyl), an alkoxycarbonyl group (e.g., methoxycarbonyl, butyloxycarbonyl, dodecyloxycarbonyl, and octadecyloxycarbonyl), a heterocyclic oxy group (e.g., 1-phenyltetrazole-5-oxy and 2-tetrahydropyranyloxy), an azo group (e.g., phenylazo, 4-methoxyphenylazo, 4-pivaroylaminophenylazo, and 2-hydroxy-4-propanoylphenylazo), an acyloxy group (e.g., acetoxy), a carbamoyloxy group (e.g., N-methylcarbamoyloxy and N-phenylcarbamoyloxy), a silyloxy group (e.g., trimethylsilyloxy and dibutylmethylsilyloxy), an aryloxycarbonylamino group (e.g., phenoxycarbonylamino), an imido group (e.g., N-succinimido, N-phthalimido, and 3-octadecenylsuccinimido), a heterocyclic thio group (e.g., 2-benzothiazolylthio, 2,4-di-phenoxy-1,3,5-tirazole-6-thio, and 2-pyridylthio), a sulfinyl group (e.g., dodecanesulfinyl, 3-pentadecylphenylsulfinyl, and 3-phenoxypropylsulfinyl), a phosphonyl group (e.g., phenoxyphosphonyl, octyloxyphosphonyl, and phenylphosphonyl), an aryloxycarbonyl group (e.g., phenoxycarbonyl), or an acyl group (e.g., acetyl, 3-phenylpropanoyl, benzoyl, and 4-dodecyloxybenzoyl).

As $R^{13}$, preferably can be mentioned an alkyl group, an aryl group, a heterocyclic group, a cyano group, a nitro group, an acylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an acyloxy group, a carbamoyloxy group, an aryloxycarbonylamino group, an imido group, a heterocyclic thio group, a sulfinyl group, a phosphonyl group, an aryloxycarbonyl group, and an acyl group.

More preferably, an alkyl group or an aryl group, further preferably, in view of cohesiveness, an alkyl group or aryl group having at least one substituent, and furthermore preferably an alkyl group or aryl group having, as a substituent, at least one alkyl group, alkoxy group, sulfonyl group, sulfamoyl group, carbamoyl group, acylamido group or sulfonamido group, is mentioned. Particularly preferably, an alkyl group or aryl group having, as a substituent, at least one alkyl group, acylamido group, or sulfonamido group, is mentioned. In the case of an aryl group, if the aryl group has these substituents, more preferably the aryl group has the substituent at least in the ortho position or the para position.

In the cyan coupler of the present invention, each of $R^{11}$ and $R^{12}$ is an electron-attracting group of 0.20 or more and the sum of the $\sigma_p$ values of $R^{11}$ and $R^{12}$ is 0.65 or more, thereby forming color as a cyan image. The sum of the $\sigma_p$ values of $R^{11}$ and $R^{12}$ is preferably 0.70 or more, and the upper limit is in the order of 1.8.

$R^{11}$ and $R^{12}$ each are an electron-attracting group whose Hammett substituent constant $\sigma_p$ value is 0.20 or more and preferably 0.30 or more, with the upper limit being 1.0 or less.

As a specific example of $R^{11}$ and $R^{12}$ that are electron-attracting groups whose $\sigma_p$ value is 0.20 or more, can be mentioned an acyl group, an acyloxy group, a carbamoyl group, an alkoxycarbonyl group, an aryloxycarbonyl group, a cyano group, a nitro group, a dialkylphosphono group, a diarylphosphono group, a diarylphosphinyl group, an alkylsulfinyl, an arylsulfinyl group, an alkylsulfonyl group, an arylsulfonyl group, a sulfonyloxy group, an acylthio group, a sulfamoyl group, a thiocyanate group, a thiocarbonyl group, a halogenated alkyl group, a halogenated alkoxy group, a halogenated aryloxy group, a halogenated alkylamino group, a halogenated alkylthio group, an aryl group substituted by another electron-attracting group whose $\sigma_p$ value is 0.20 or more, a heterocyclic group, a halogen atom, an azo group, or a selenocyanate group. Out of these substituents, the groups that can be further substituted may further have the substituent(s) as mentioned for $R^{13}$.

With respect to $R^{11}$ and $R^{12}$, more specifically, the electron-attracting group whose $\sigma_p$ value is 0.20 or more represents an acyl group (e.g., acetyl, 3-phenylpropanoyl, benzoyl, and 4-dodecyloxybenzoyl), an acyloxy group (e.g., acetoxy), a carbamoyl group (e.g., carbamoyl, N-ethylcarbamoyl, N-phenylcarbamoyl, N,N-dibutylcarbamoyl, N-(2-dodecyloxyethyl)carbamoyl, N-(4-n-pentadecaneamido)phenylcarbamoyl, N-methyl-N-dodecylcarbamoyl, and N-{3-(2,4-di-t-amylphenoxy)propyl}carbamoyl), an alkoxycarbonyl group (e.g., methoxycarbonyl, ethoxycarbonyl, iso-propyloxycarbonyl, tert-butyloxycarbonyl, iso-butyloxycarbonyl, butyloxycarbonyl, dodecyloxycarbonyl, and octadecyloxycarbonyl), an aryloxycarbonyl group (e.g., phenoxycarbonyl), a cyano group, a nitro group, a dialkylphosphono group (e.g., dimethylphosphono), a diarylphosphono group (e.g., diphenylphosphono), a diarylphosphinyl group (e.g., diphenylphosphinyl), an alkylsulfinyl group (e.g., 3-phenoxypropylsulfinyl), an arylsulfinyl group (e.g., 3-pentadecylphenylsulfinyl), an alkylsulfonyl group (e.g., methanesulfonyl and octanesulfonyl), an arylsulfonyl group (e.g., benzenesulfonyl and toluenesulfonyl), a sulfonyloxy group (e.g., methanesulfonyloxy and toluenesulfonyloxy), an acylthio group (e.g., acetylthio and benzoylthio), a sulfamoyl group (e.g., N-ethylsulfamoyl, N,N-dipropylsulfamoyl, N-(2-dodecyloxyethyl)sulfamoyl, N-ethyl-N-dodecylsulfamoyl, and N,N-diethylsulfamoyl), a thiocyanate group, a thiocarbonyl group (e.g., methylthiocarbonyl and phenylthiocarbonyl), a halogenated alkyl group (e.g., trifluoromethane and heptafluoropropane), a halogenated alkoxy group (e.g., trifluoromethyloxy), a halogenated aryloxy group (e.g., pentafluorophenyloxy), a halogenated alkylamino group (e.g., N,N-di-(trifluoromethyl)amino), a halogenated alkylthio group (e.g., difluoromethylthio and 1,1,2,2-tetrafluoroethylthio), an aryl group substituted by another electron-attracting group with $\sigma_p$ 0.20 or more (e.g., 2,4-dinitrophenyl, 2,4,6-trichlorophenyl, and pentachlorophenyl), a heterocyclic group (e.g., 2-benzooxazolyl, 2-benzothiazolyl, 1-phenyl-2-benzimidazolyl, 5-chloro-1-tetrazolyl, and 1-pyrrolyl), a halogen atom (e.g., a chlorine atom and a bromine atom), an azo group (e.g., phenylazo), or a selenocyanate group. Out of these substituents, the groups that can be further substituted may further have the substituent(s) as mentioned for $R^{13}$.

As preferable $R^{11}$ and $R^{12}$, can be mentioned an acyl group, an acyloxy group, a carbamoyl group, an alkoxycarbonyl group, an aryloxycarbonyl group, a cyano group, a nitro group, an alkylsulfinyl group, an arylsulfinyl group, an alkylsulfonyl group, an arylsulfonyl group, a sulfamoyl group, a halogenated alkyl group, a halogenated alkyloxy group, a halogenated alkylthio group, a halogenated aryloxy group, an aryl group substituted by two or more electron-attracting groups with $\sigma_p$ 0.20 or more, and a heterocyclic group; and more preferably an alkoxycarbonyl group, a nitro group, a cyano group, an arylsulfonyl group, a carbamoyl group, and a halogenated alkyl group. Most preferably $R^{11}$ is a cyano group. Particularly preferably $R^{12}$ is an alkoxycarbonyl group, and most preferably a branched-chain alkoxycarbonyl group (particularly a cycloalkoxycarbonyl group).

X represents a hydrogen atom or a group capable of being split-off upon coupling reaction with the oxidized product of an aromatic primary amine color-developing agent, and specifically examples of the group capable of being split-off include a halogen atom, an alkoxy group, an aryloxy group, an acyloxy group, an alkyl- or aryl-sulfonyloxy group, an acylamino group, an alkyl- or aryl-sulfonamido group, an alkoxycarbonyloxy group, an aryloxycarbonyloxy group, an alkylthio, arylthio, or heterocyclic thio group, a carbamoylamino group, a carbamoyloxy group, a heterocyclic carbonyloxy group, a 5- or 6-membered nitrogen-containing heterocyclic group, an imido group, an arylazo group, and the like, each of which may further be substituted by the group that is an allowable substituent of $R^{13}$.

More specifically, examples of X include a halogen atom (e.g. fluorine atom, chlorine atom, and bromine atom), an alkoxy group (e.g. ethoxy, dodecyloxy, methoxyethylcarbamoylmethoxy, carboxypropyloxy, methanesulfonylethoxy, and ethoxycarbonylmethoxy), an aryloxy group (e.g. 4-methylphenoxy, 4-chlorophenoxy, 4-methoxyphenoxy, 4-carboxyphenoxy, 3-ethoxycarbonylphenoxy, 3-acetylaminophenoxy, and 2-carboxyphenoxy), an acyloxy group (e.g. acetoxy, tetradecanoyloxy, and benzoyloxy), an alkyl- or arylsulfonyloxy group (e.g. methansulfonyloxy, and toluenesulfonyloxy), an acylamino group (e.g. dichloroacetylamino and heptafluorobutyrylamino), an alkyl- or arylsulfonamido group (e.g. methanesulfonylamino, trifuloromethanesulfonylamino, and p-toluenesufonylamino), an alkoxycarbonyloxy group (e.g. ethoxycarbonyloxy and benzyloxycarbonyloxy), an aryloxycarbonyloxy group (e.g. phenoxycarbonyloxy), an alkylthio, arylthio, or heterocyclic thio group (e.g. dodecylthio, 1-carboxydodecylthio, phenylthio, 2-butoxy-5-t-octylphenylthio, tetrazolylthio), a carbamoylamino group (e.g. N-methylcarbamoylamino and N-phenylcarbamoylamino), a carbamoyl group (e.g. N,N-diethylcarbamoyl, N-ethylcarbamoyl, N-ethyl-N-phenylcarbamoyl), a heterocyclic carbonyloxy group (e.g. morpholinocarbonyloxy and piperidinocarbonyloxy), a 5- or 6-membered nitrogen-containing heterocyclic group (e.g. imidazolyl, pyrazolyl, triazolyl, tetrazolyl, 1,2-dihydro-2-oxo-1-pyridyl), an imido group (e.g. succinimido and hydantoinyl), and an aryl azo group (e.g. phenylazo and 4-methoxyphenylazo). In addition to these, in some cases, X takes the form of a bis-type coupler that is obtained by condensing a four-equivalent coupler with aldehydes or ketones, as a split-off group bonded through a carbon atom. Further, X may contain a photographically useful group, such as a development inhibitor and a development accelerator.

Preferable X is a halogen atom, an alkoxy group, an aryloxy group, an alkyl- or aryl-thio group, an alkyloxycarbonyloxy group, an aryloxycarbonyloxy group, a carbamoyloxy group, a heterocyclic carbonyloxy group, or a 5- or 6-membered nitrogen-containing heterocyclic group bonded through the nitrogen atom to the coupling active site. More preferable X is a halogen atom, an alkyl- or aryl-thio group, an alkyloxycarbonyloxy group, an aryloxycarbonyloxy group, a carbamoyloxy group, or a heterocyclic carbonyloxy group, and particularly preferably a carbamoyloxy group or a heterocyclic carbonyloxy group.

With respect to the cyan coupler represented by general formula (A), the group represented by $R^{11}$, $R^{12}$, $R^{13}$ or X may be a divalent group, to form a dimer or a higher polymer, or to bond to a polymer chain to form a homopolymer or a copolymer. The homopolymer or the copolymer formed by bonding to a polymer chain is typically a monopolymer or a copolymer of an addition polymer ethylenically unsaturated compound having a cyan coupler residue represented by general formula (A). In this case, the polymer may contain one or more types of the cyan color-forming repeating units having the cyan coupler residue represented by general formula (A), and the copolymer may be a copolymer containing one or more types of non-color-forming ethylenically monomers as a copolymer component. The cyan color-forming repeating unit having a cyan coupler residue represented by general formula (A) is preferably represented by the following general formula (P):

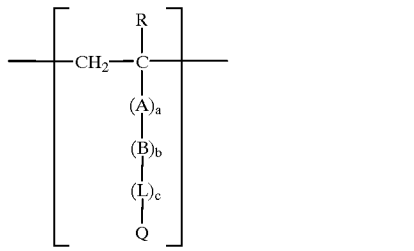

(P)

wherein R represents a hydrogen atom, an alkyl group having 1 to 4 carbon atoms, or a chlorine atom, A represents —CONH—, —COO—, or a substituted or unsubstituted phenylene group, B represents a substituted or unsubstituted alkylene group, phenylene group, or aralkylene group, L represents —CONH—, —NHCONH—, —NHCOO—, —NHCO—, —OCONH—, —NH—, —COO—, —OCO—, —CO—, —O—, —S—, —$SO_2$—, —$NHSO_2$— or —$SO_2NH$—. a, b, and c represent 0 or 1. Q represents a cyan coupler residue formed by releasing a hydrogen atom from $R^{11}$, $R^{12}$, $R^{13}$, or X of the compound represented by general formula (A). As the polymer, a copolymer of a cyan-color-forming monomer represented by the coupler unit of general formula (A) with a non-color-forming ethylenically monomer that does not couple with the oxidized product of an aromatic primary amine developing agent is preferable.

As the non-color-forming ethylenically monomer that does not couple with the oxidized product of an aromatic primary amine developing agent, there, for example, are acrylic acid, α-chloroacrylic acid, and an α-alkyl acrylic acids (e.g., methacrylic acid and the like) and amides or esters derived from these acrylic acids (e.g., acrylamide, methacrylamide, n-butylacrylamide, t-butylacrylamide, diacetone acrylamide, methyl acrylate, ethyl acrylate, n-propyl acrylate, n-butyl acrylate, t-butyl acrylate, iso-butyl acrylate, 2-ethylhexyl acrylate, n-octyl acrylate, lauryl acrylate, methyl methacrylate, ethyl methacrylate, n-butyl methacrylate, and β-hydroxymethacrylate), vinyl esters (e.g., vinyl acetate, vinyl propionate, and vinyl laurate), acrylonitrile, methacrylonitrile, aromatic vinyl compounds (e.g., styrene and its derivative, such as vinyltoluene, divinylbenzene, vinylacetophenone, and sulfostyrene), itaconic acid, citraconic acid, crotonic acid, vinylidene chloride, vinyl alkyl ethers (e.g., vinyl ethyl ether), maleates, N-vinyl-2-pyrrolidone, N-vinylpyridine, and 2- and 4-vinylpyridine.

Particularly, acrylates, methacrylates, and maleates are preferable. The non-color-forming ethylenically monomers used herein can be used in the form of a combination of two or more; for example, methyl acrylate and butyl acrylate, butyl acrylate and styrene, butyl methacrylate and methacrylic acid, methacrylate and diacetone acrylamide, and the like may be used.

As is well known in the field of polymer couplers, the ethylenically unsaturated monomer to be copolymerized with the vinyl-series monomer corresponding to the above general formula (A) can be chosen so that the physical properties and/or the chemical properties of the copolymer to be formed—for example, the solubility, the compatibility with the binder of photographic colloid compositions, such as gelatin; the flexibility, the heat stability, and the like—may be favorably influenced.

To incorporate the cyan coupler of the present invention into the silver halide light-sensitive material preferably into a red-sensitive silver halide emulsion layer, preferably the cyan coupler is made into a so-called incorporated coupler, and to do so, preferably at least one group of $R^{11}$, $R^{12}$, $R^{13}$, and X is a so-called ballasting group (preferably having 10 or more carbon atoms in total), and more preferably the number of carbon atoms in total is 10 to 50. In particular, preferably $R^{13}$ has a ballasting group.

The cyan coupler represented by general formula (A) is more preferably a compound having a structure represented by the following general formula (D):

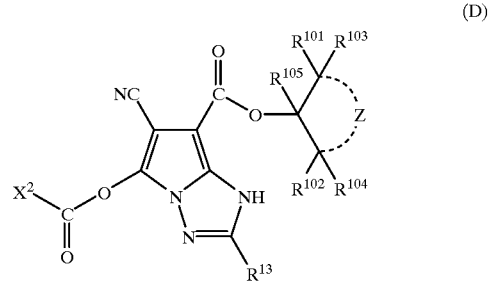

(D)

wherein $R^{101}$, $R^{102}$, $R^{103}$, $R^{104}$, and $R^{105}$, which are the same or different, each represent a hydrogen atom or a substituent. As the substituent, a substituted or unsubstituted aliphatic group or a substituted or unsubstituted aryl group is preferable, and more preferable ones are described below.

$R^{101}$ and $R^{102}$ preferably represent an aliphatic group, for example, a straight-chain, branched-chain or cyclic alkyl group, aralkyl group, alkenyl group, alkynyl group, or cycloalkenyl group, each having 1 to 36 carbon atoms, and specifically, for example, methyl, ethyl, propyl, isopropyl, t-butyl, t-amyl, t-octyl, tridecyl, cyclopentyl, or cyclohexyl. The aliphatic group has more preferably 1 to 12 carbon atoms. $R^{103}$, $R^{104}$, and $R^{105}$ represent a hydrogen atom or an aliphatic group. As the aliphatic group, those mentioned above for $R^{101}$ and $R^{102}$ can be mentioned. Particularly preferably $R^{103}$, $R^{104}$, and $R^{105}$ are a hydrogen atom.

Z represents a group of non-metal atoms required to form a 5- to 8-membered ring, which ring may be substituted and may be a saturated ring or have a unsaturated bond. As preferable non-metal atoms, a nitrogen atom, an oxygen atom, a sulfur atom, and a carbon atom can be mentioned, and a carbon atom is more preferable.

As the ring formed by Z, for example, a cyclopentane ring, a cyclohexane ring, a cycloheptane ring, a cyclooctane ring, a cyclohexene ring, a piperazine ring, an oxane ring, and a thiane ring can be mentioned. These rings may be substituted by such substituents as represented by $R^{13}$ described later.

The ring formed by Z is preferably an optionally substituted cyclohexane ring, and particularly preferably a cyclohexane ring whose 4-position is substituted by an alkyl group having 1 to 24 carbon atoms (that may be substituted by such a substituent as represented by $R^{13}$ described above).

R$^{13}$ in formula (D) has the same meaning as R$^{13}$ in formula (A), and it is particularly preferably an alkyl group or an aryl group and more preferably a substituted aryl group. Concerning the number of carbon atoms, in the case of the alkyl group, preferably the alkyl group has 1 to 36 carbon atoms and in the case of the aryl group, preferably the aryl group has 6 to 36 carbon atoms.

Out of the aryl groups, one wherein the ortho position to the position where it is attached to the coupler mother nucleus is substituted by an alkoxy group is not preferable, because the fastness to light of the dye originated from the coupler is low.

In this connection, the substituent of the aryl group is preferably a substituted or unsubstituted alkyl group, and inter alia an unsubstituted alkyl group is most preferable. Particularly, an unsubstituted alkyl group having 1 to 30 carbon atoms is preferable.

X$^2$ represents a hydrogen atom or a substituent. The substituent is preferably a group that accelerates the release of the X$^2$—C(=O)O— group at the time of the oxidation coupling reaction. Preferably X$^2$ is, out of them, a heterocyclic ring, a substituted or unsubstituted amino group, or an aryl group. As the heterocyclic ring, a 5- to 8-membered ring having a nitrogen atom(s), an oxygen atom(s), or a sulfur atom(s) and 1 to 36 carbon atoms is preferable. A 5- or 6-membered ring bonded through a nitrogen atom is more preferable, with particular preference given to a 6-membered ring. These rings may form a condensed ring with a benzene ring or a heterocyclic ring. As specific examples, imidazole, pyrazole, triazole, lactam compounds, piperidine, pyrrolidine, pyrrole, morpholine, pyrazolidine, thiazolidine, pyrazoline, and the like can be mentioned, with preference given to morpholine and piperidine and particular preference to morpholine.

As the substituent of the substituted amino group, an aliphatic group, an aryl group, or a heterocyclic group can be mentioned. As the aliphatic group, the substituents of R$^{13}$ mentioned above can be mentioned, which may further be substituted by a cyano group, an alkoxy group (e.g., methoxy), an alkoxycarbonyl group (e.g., ethoxycarbonyl), a chlorine atom, a hydroxyl group, a carboxyl group, or the like. As the substituted amino group, a di-substituted amino group is preferred over a mono-substituted amino group. The substituent is preferably an alkyl group.

As the aryl group, one having 6 to 36 carbon atoms is preferable, and a single ring is more preferable. As specific examples, phenyl, 4-t-butylphenyl, 2-methylphenyl, 2,4,6-trimethylphenyl, 2-methoxyphenyl, 4-methoxyphenyl, 2,6-dichlorophenyl, 2-chlorophenyl, 2,4-dichlorophenyl, and the like can be mentioned.

Preferably the cyan coupler represented by general formula (D) used in the present invention has, in the molecule, a group that makes it soluble in an oil, so that the cyan coupler may be easily soluble in a high-boiling organic solvent, and that this cyan coupler itself and the dye formed by the oxidation coupling of this cyan coupler with a color-forming reducing agent (developing agent) are non-diffusible in hydrophilic colloid layers.

For the coupler represented by general formula (D), R$^{13}$ may contain a coupler residue represented by general formula (D) to form a dimer or a higher polymer, or R$^{13}$ may contain a polymer chain to form a homopolymer or a copolymer. The homopolymer or the copolymer containing a polymer chain is typically a homopolymer or a copolymer of an addition copolymer ethylenically unsaturated compound having a coupler residue represented by general formula (D). In this case, with respect to the cyan color-forming repeating unit having a coupler residue represented by general formula (D), one or more kinds of such cyan color-forming repeating units may be contained in the polymer. The copolymer may contain, as a copolymer component(s), one, or two or more non-color-forming ethylenically monomers that do not couple with the oxidation product of an aromatic primary amine developing agent, such as acrylates, methacrylates, and maleates.

Hereinbelow, specific examples of the cyan coupler defined by the present invention are shown, but the present invention is not restricted to them.

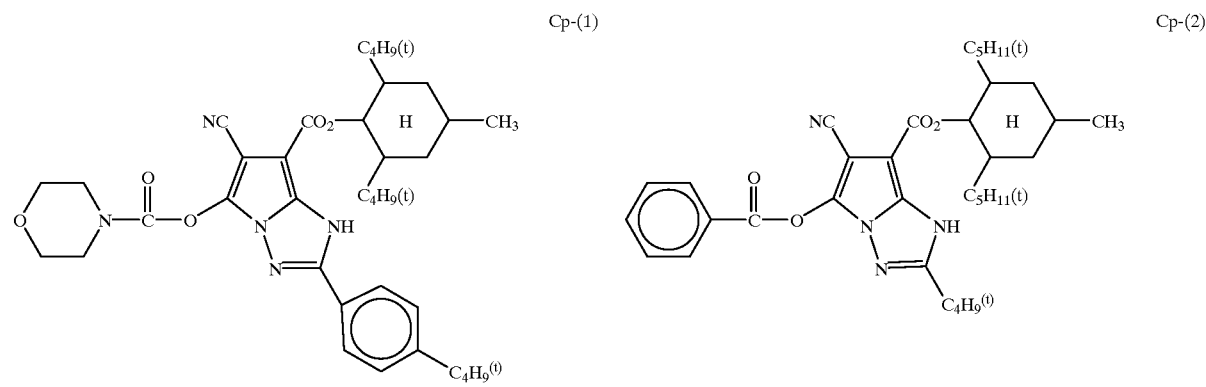

-continued
Cp-(3)
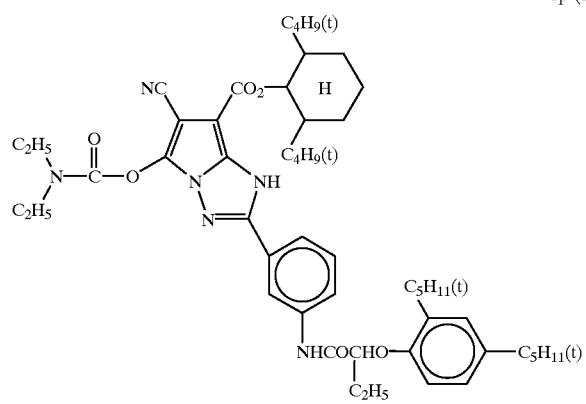
Cp-(4)
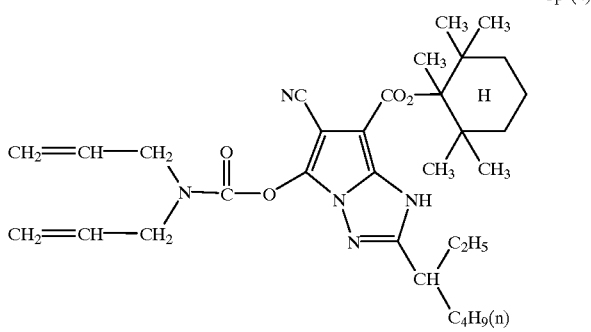
Cp-(5)
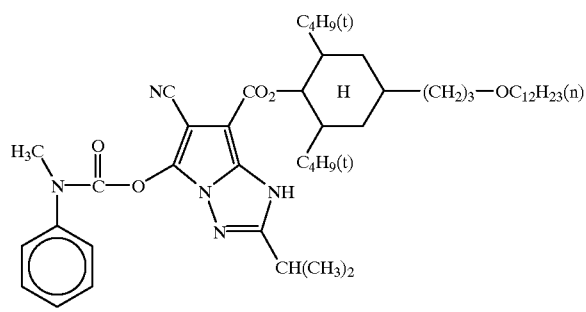
Cp-(6)
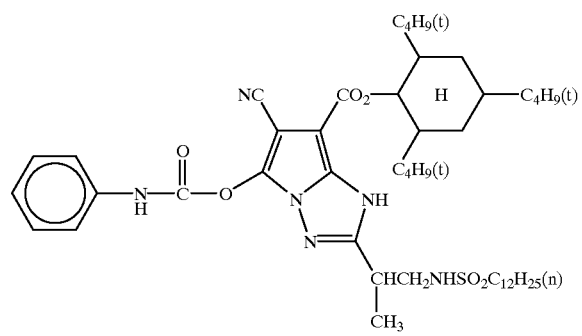
Cp-(7)
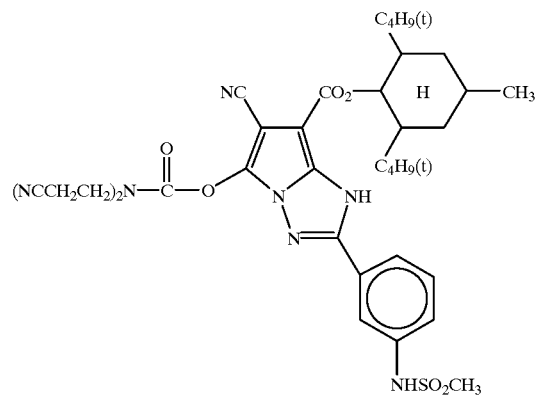
Cp-(8)
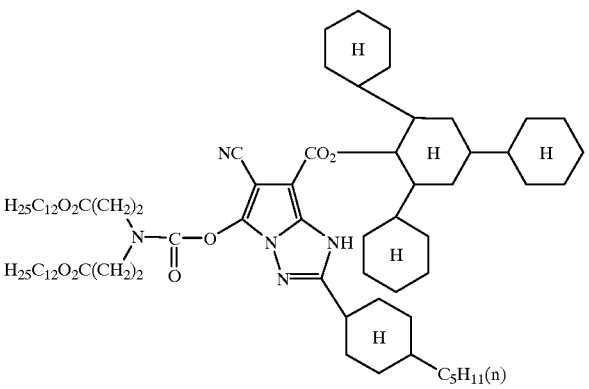
Cp-(9)
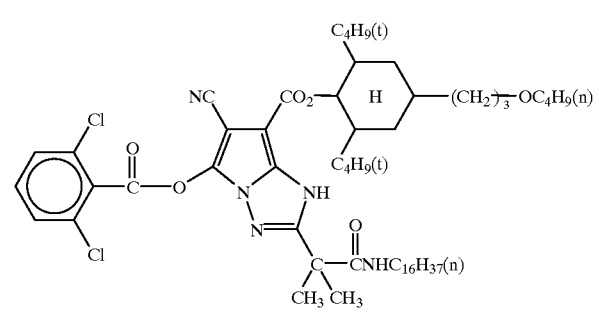
Cp-(10)
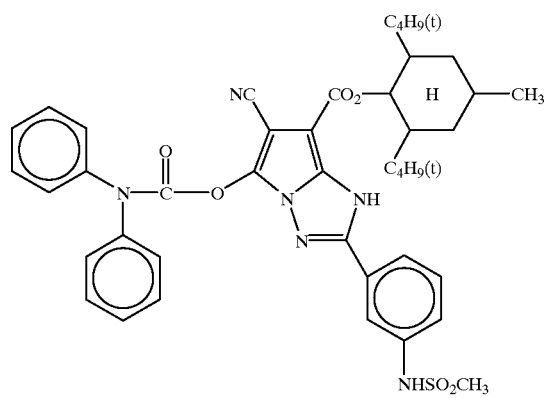

-continued
Cp-(11)
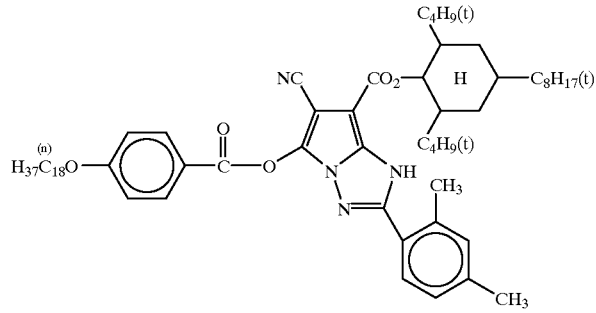
Cp-(12)
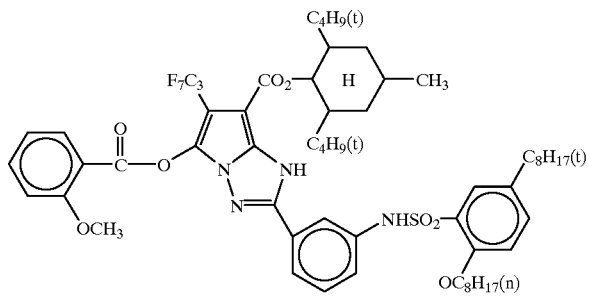
Cp-(13)
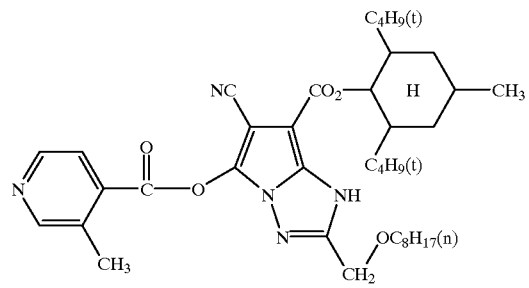
Cp-(14)
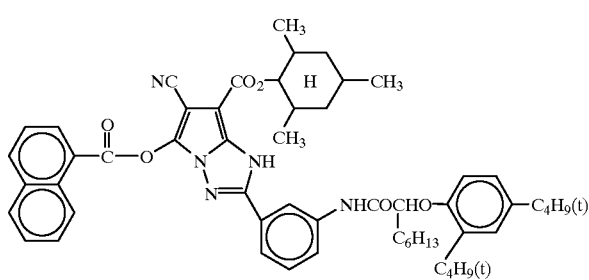
Cp-(15)
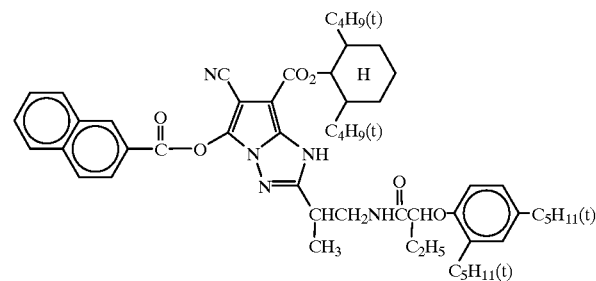
Cp-(16)
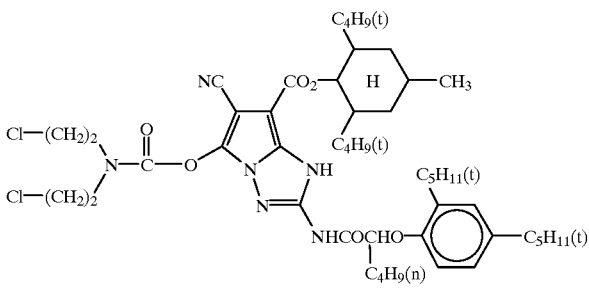
Cp-(17)
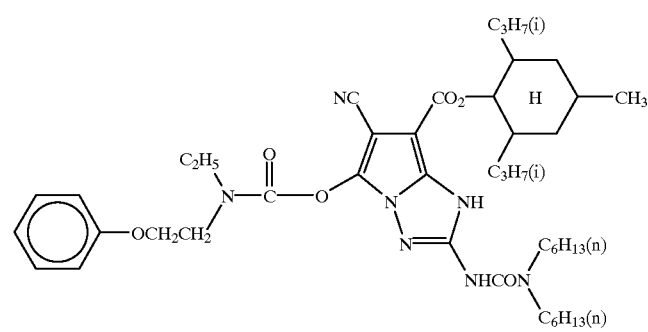

-continued
Cp-(18)
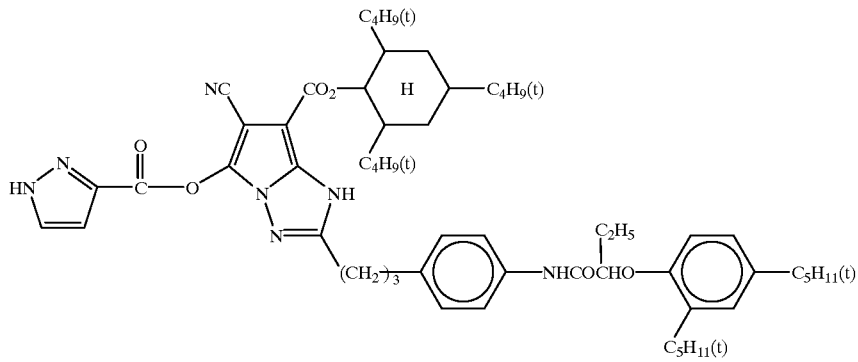
Cp-(19)
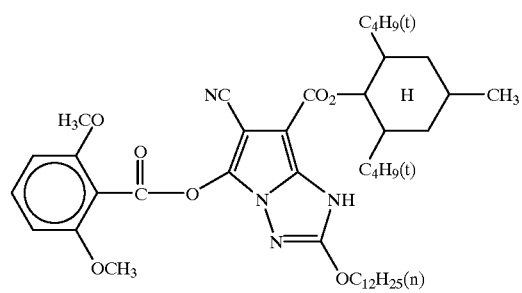
Cp-(20)
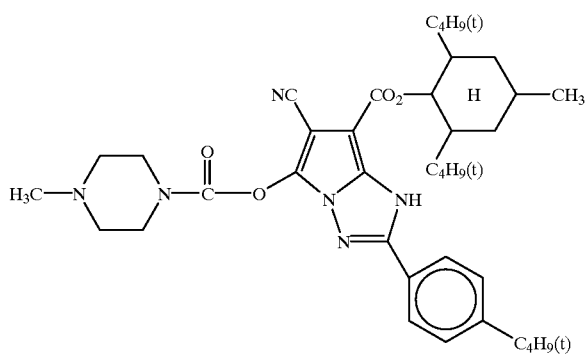
Cp-(21)
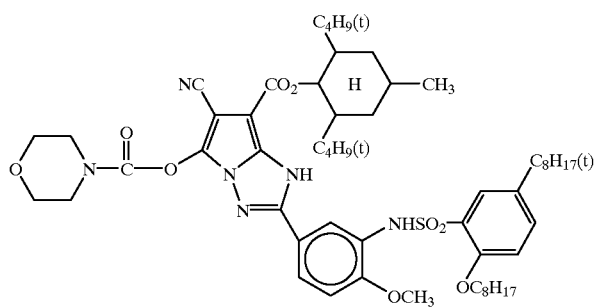
Cp-(22)
Cp-(23)
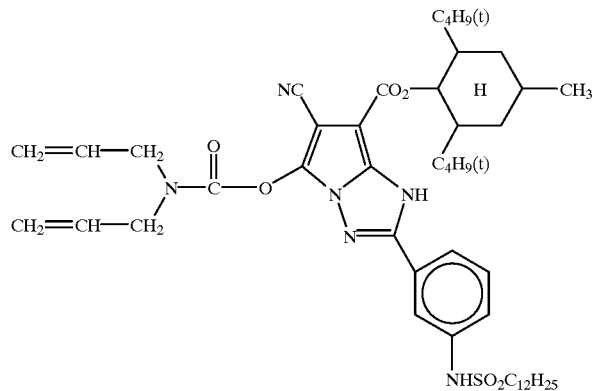
Cp-(24)
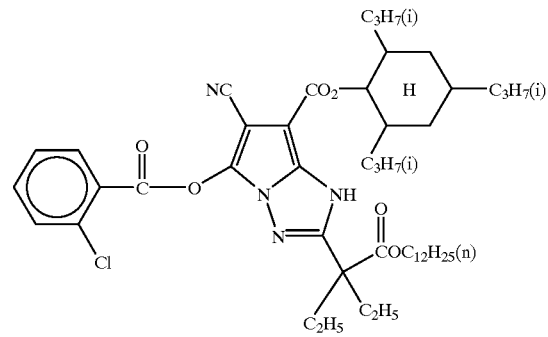

-continued
Cp-(25)
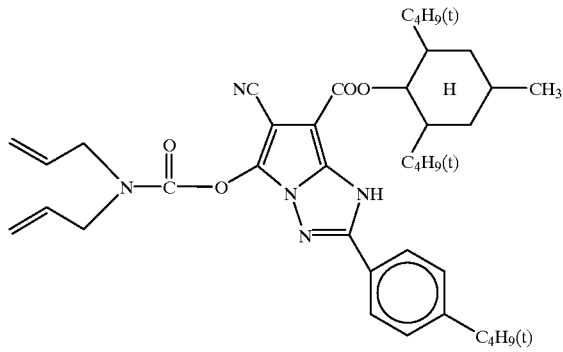
Cp-(26)
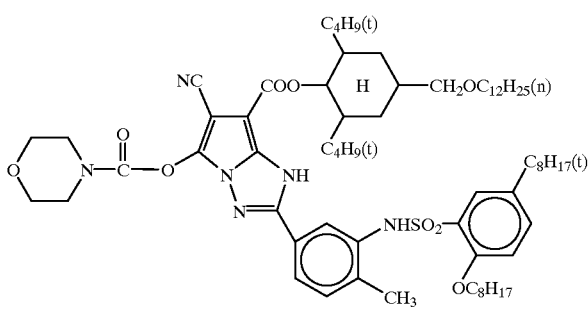
Cp-(27)
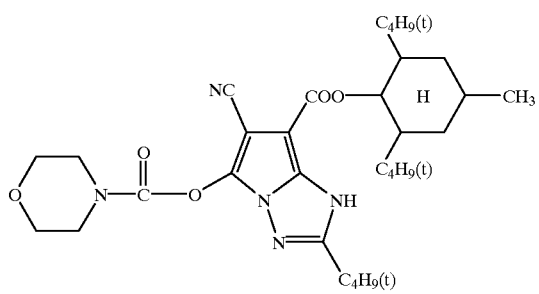
Cp-(28)
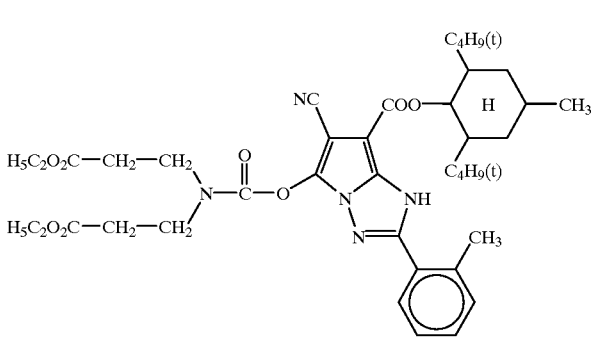
Cp-(29)
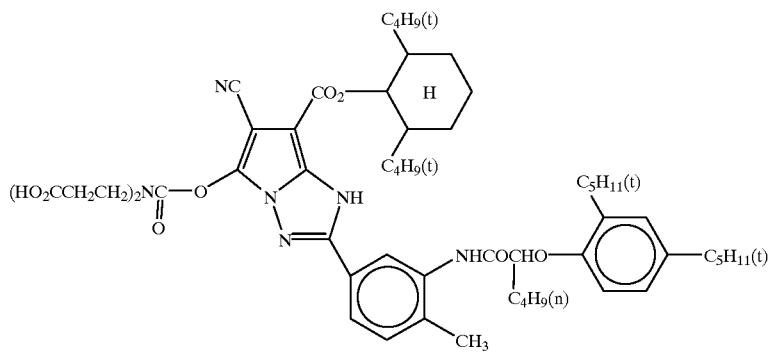
Cp-(30)
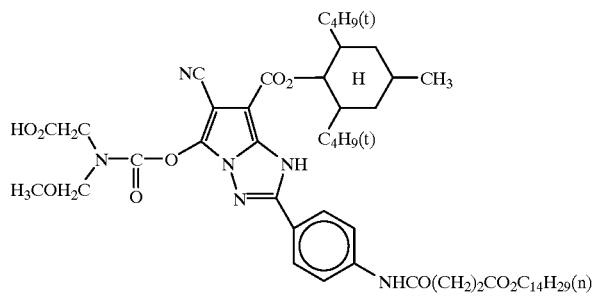
Cp-(31)
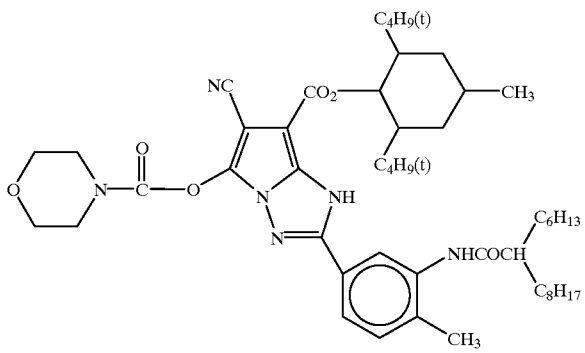

-continued
Cp-(32)
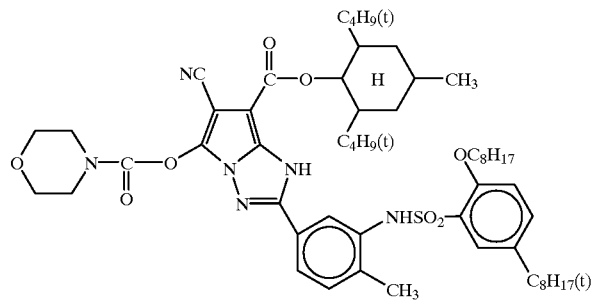
Cp-(33)
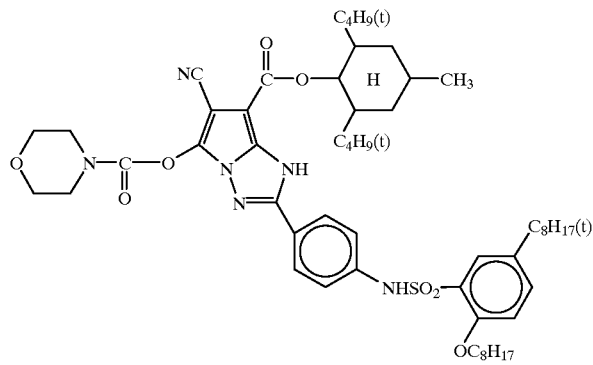
Cp-(34)
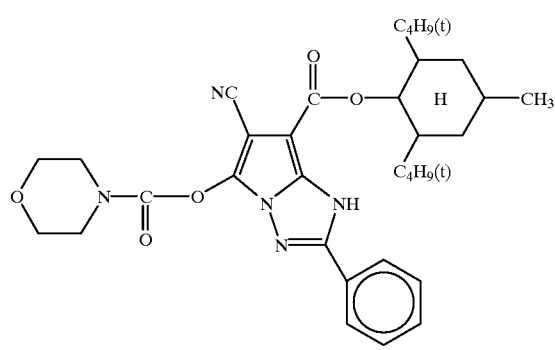
Cp-(35)
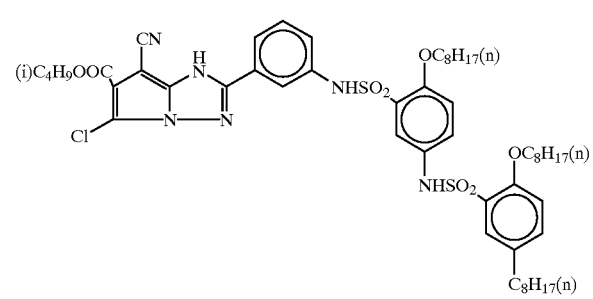
Cp-(36)
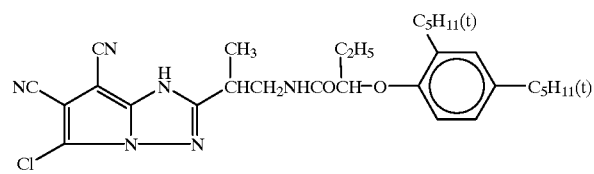
Cp-(37)
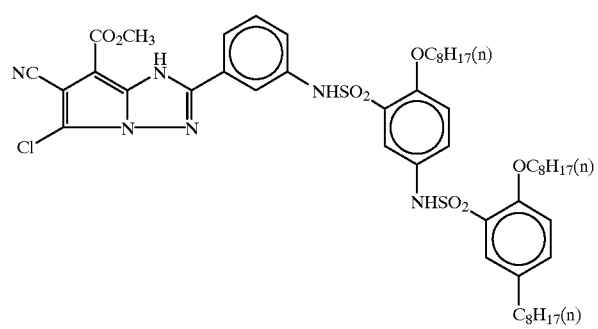
Cp-(38)
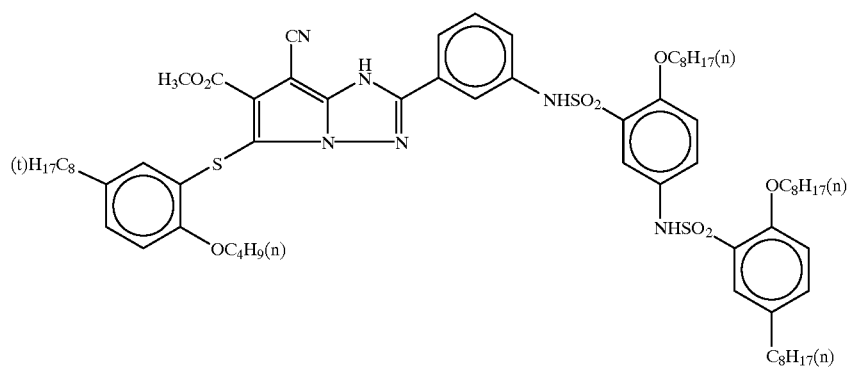

-continued
Cp-(39)
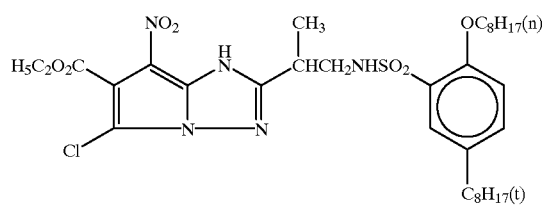
Cp-(40)
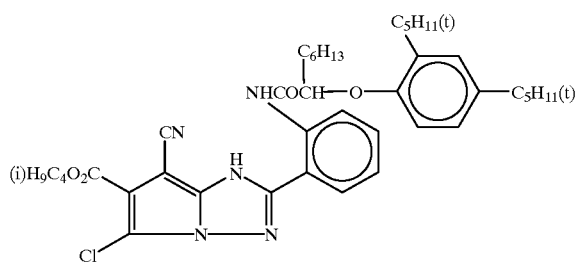
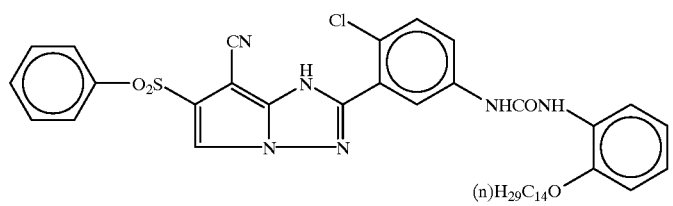
Cp-(41)
Cp-(42)
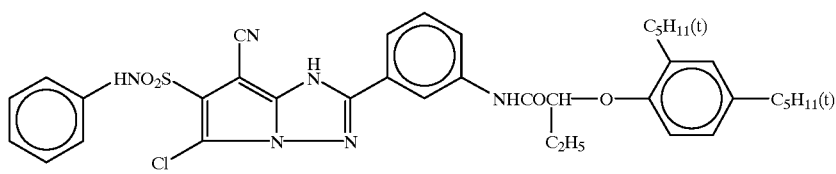
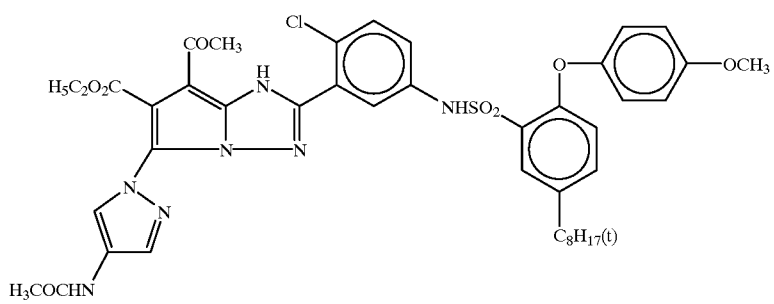
Cp-(43)
Cp-(44)
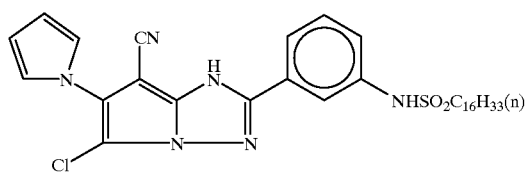
Cp-(45)
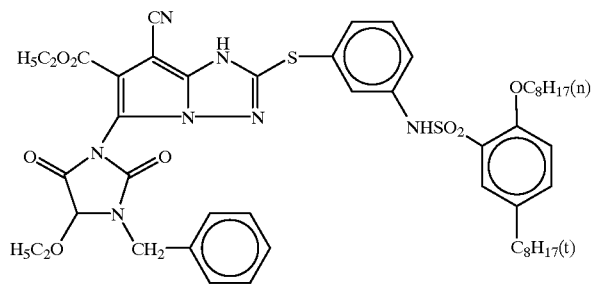

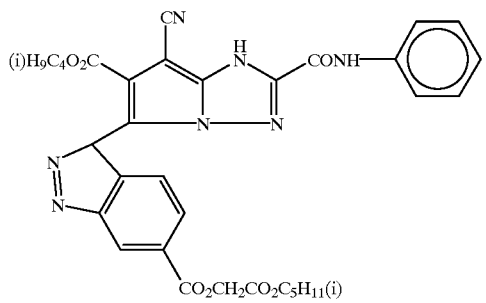

Cp-(46)

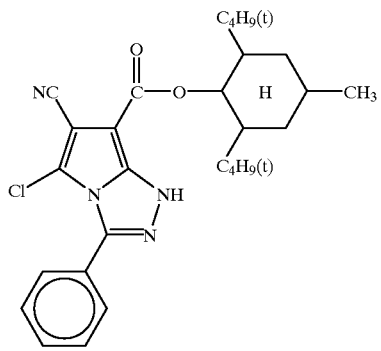

Cp-(47)

The compound represented by general formula (A) can be synthesized by the known method, for example, by methods described in JP-A-5-150423, JP-A-5-255333, JP-A-5-202004, JP-A-7-48376, and JP-A-9-189988.

Now, the compound represented by general formula (B) is described in detail. $R^a$ and $R^b$ each independently represent a substituted or unsubstituted aryl group, or a substituted or unsubstituted alkyl group having 2 to 30 carbon atoms in all including the number of carbon atoms in the substituent.

When $R^a$ and $R^b$ represent an aryl group, the substituent that substitutes the aryl group includes the substituents described for $R^{13}$ in formula (A), and as their specific examples, can be mentioned those described for $R^{13}$.

Out of them, an alkyl group, an alkoxy group, an acylamino group, a halogen atom, an aminocarbonylamino group, and an alkoxycarbonylamino group are more preferable.

An alkyl group (having 1 to 10 carbon atoms), a halogen atom (a chlorine atom and a bromine atom), and an alkoxy group (having 1 to 10 carbon atoms) are most preferable. When $R^a$ and $R^b$ are an aryl group, preference is given to an unsubstituted aryl group over a substituted aryl group.

When $R^a$ and $R^b$ are an alkyl group, the number of carbon atoms is 2 to 30 in all including the number of carbon atoms in its substituent. The unsubstituted alkyl group may be straight-chain or branched-chain. Preferably, the straight-chain alkyl is one having 2 to 26 carbon atoms (e.g., ethyl, n-propyl, n-butyl, n-hexyl, n-octyl, n-decyl, n-octadecyl, and n-eicosyl), and preferably, the branched-chain alkyl has 2 to 26 carbon atoms (e.g., i-propyl, t-butyl, and 2-ethylhexyl).

When $R^a$ and $R^b$ are a substituted alkyl group, the substituent includes the substituents described for $R^{13}$ of formula (A), and preferably the number of carbon atoms is 2 to 20 in all including the number of carbon atoms in the substituent. As their specific examples, can be mentioned those described for $R^{13}$, and specific examples thereof include ethoxymethyl, acetoxymethyl, stearoyloxymethyl, p-phenoxymethyl, 1-nitrophenoxymethyl, 1-chlorooctyl, and the like.

$R^{14}$ and $R^{15}$ represent a hydrogen atom, a substituted or unsubstituted alkyl group, or a substituted or unsubstituted aryl group. When $R^{14}$ and $R^{15}$ are a substituted alkyl group or a substituted aryl group, the substituent includes those substituents described for $R^{13}$ of formula (A) and their specific examples include those described for $R^{13}$.

When $R^{14}$ or $R^{15}$ is an alkyl group, preferably the number of carbon atoms is 1 to 20. Preference is given to an unsubstituted alkyl group over a substituted alkyl group.

When $R^{14}$ or $R^{15}$ are an aryl group, preferably the number of carbon atoms is 6 to 20. Preferably at least one of $R^{14}$ or $R^{15}$ is a hydrogen atom, and most preferably both $R^{14}$ and $R^{15}$ are hydrogen atoms.

$R^{16}$ is a substituted or unsubstituted aryl group, the substituent that substitutes the aryl group includes the substituents described for $R^{13}$ of formula (A). As specific examples of the substituent, can be mentioned those described for formula (A).

Preferably the substituent is an alkyl group (having 1 to 20 carbon atoms, e.g., methyl, ethyl, i-propyl, t-butyl, and n-octyl), an alkoxy group (having 1 to 20 carbon atoms, e.g., methoxy, ethoxy, i-propoxy, t-butoxy, n-octyloxy, n-tetradecyloxy, n-hexadecyloxy, and n-octadecyloxy), an acylamino group (having 1 to 20 carbon atoms, e.g., an acetylamino group, propionylamino, and stearoylamino), an alkoxycarbonylamino (having 2 to 20 carbon atoms, e.g., methoxycarbonylamino, ethoxycarbonylamino, and octyloxycarbonylamino), an aminocarbonylamino (having 1 to 20 carbon atoms, e.g., dimethylaminocarbonylamino and dioctylaminocarbonylamino), an alkylsulfonylamino group (having 1 to 20 carbon atoms, e.g., methanesulfonylamino, ethanesulfonylamino, butanesulfonylamino, and octanesulfonylamino), an arylsulfonylamino (having 6 to 20 carbon atoms, e.g., benzenesulfonylamino, toluenesulfonylamino, and dodecylbenzenesulfonylamino).

In view of the nondiffusibility, in the compound of formula (B), preferably at least one of $R^a$, $R^b$, $R^{14}$, $R^{15}$, and $R^{16}$ has a so-called ballasting group. Preferably, the molecular weight is 200 or more, more preferably 250 or more, further preferably 300 or more, and most preferably 350 or more.

The compound of formula (C) is described in detail. $R^{14}$, $R^{15}$, and $R^{16}$ of formula (C) have the same meanings as those of formula (B). Their specific examples and preferable examples are the same as those of formula (B). $R^c$ represents a substituted or unsubstituted alkyl group, or a substituted or unsubstituted aryl group.

When $R^c$ is an alkyl group or an aryl group, the substituent possessed by them includes those substituents described for $R^{13}$ of formula (A). Their specific examples include those described for $R^{13}$.

Preferably $R^c$ is an alkyl group (having 1 to 20 carbon atoms, e.g., methyl, ethyl, i-propyl, t-butyl, n-octyl, n-octadecyl, 2-ethylhexyl, 2-methoxyethyl, and 2-chloroethyl), or an aryl group (having 6 to 20 carbon atoms, e.g., phenyl, naphthyl, p-chlorophenyl, m-methoxyphenyl, and o-methylphenyl).

In view of the nondiffusibility, in the compound of formula (C), preferably at least one of $R^c$, $R^{14}$, $R^{15}$, and $R^{16}$ has a so-called ballasting group. Preferably, the molecular weight is 200 or more, more preferably 250 or more, further preferably 300 or more, and most preferably 350 or more.

Out of the phenidone compounds represented by general formula (B) or (C) of the present invention, preferable ones are the compounds represented by general formula (C).

Among them, the phenidone compounds of the structure represented by general formula (VIII) are preferable. The definition and preferable examples of $R^{2a}$, $R^4$, $R^5$, $R^6$, $R^7$, $R^8$, and $R^9$ are the same as described above.

$R^{2a}$ is preferably a substituted or unsubstituted alkyl group having 1 to 30 carbon atoms; $R^4$ is preferably a hydrogen atom; and preferably, at least one of $R^5$, $R^6$, $R^7$, $R^8$, and $R^9$ is an alkoxy group, an acylamino group, an alkylsulfonylamino group, or an arylsulfonylamino group and all the others are a hydrogen atom, or all $R^5$, $R^6$, $R^7$, $R^8$, and $R^9$ are preferably a hydrogen atom.

Most preferably, $R^{2a}$ is an unsubstituted alkyl group having 12 to 30 carbon atoms (preferably 14 to 28 carbon atoms, and more preferably 16 to 26 carbon atoms), and all $R^4$, $R^5$, $R^6$, $R^7$, $R^8$, and $R^9$ are a hydrogen atom.

In passing, as specific examples of the group represented by $R^{c2}$ in formula (IX), can be mentioned those described for $R^2$ of formula (II). Further, as specific examples of the groups represented by $R^{14}$ and $R^{15}$, can be mentioned those described for $R^{14}$ and $R^{15}$ of formula (B). Further, specific examples of the group represented by $R^{c2'}$ in formula (IXa) are the same as those of $R^{c2}$ of formula (IX) and $R^{14}$ and $R^{15}$ are the same as those shown in formula (IX).

The compound represented by general formula (B) or (C) of the present invention includes Ph-(1) to Ph-(16) and in addition the following specific examples, but the present invention is not limited to them.

Ph-(17)
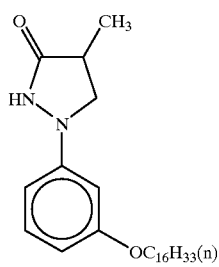

Ph-(18)
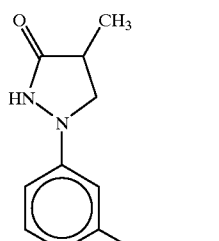

Ph-(19)
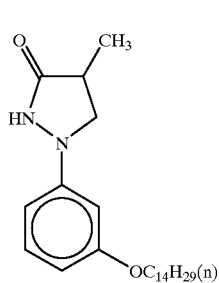

Ph-(20)
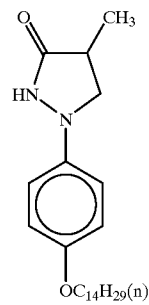

Ph-(21)
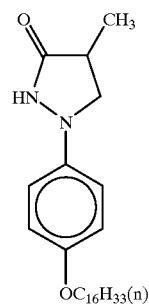

Ph-(22)
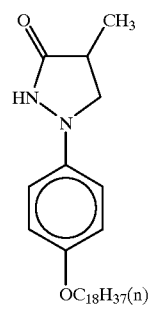

Ph-(23)
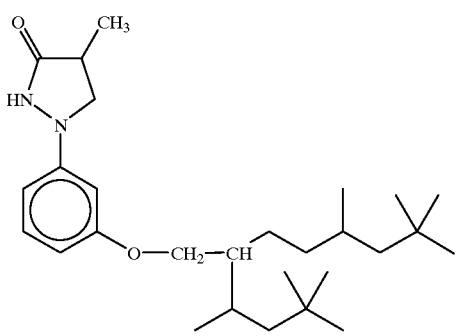

Ph-(24)
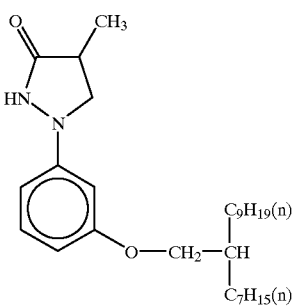

Ph-(25)
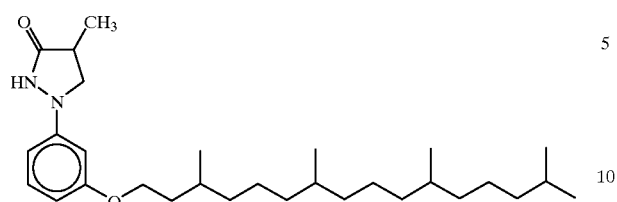
Ph-(26)
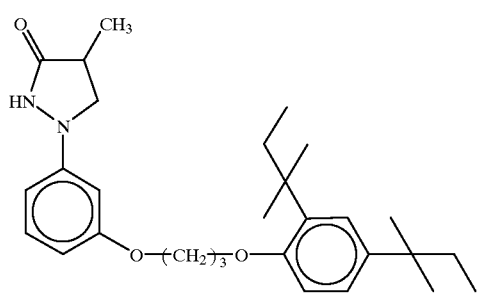
Ph-(27)
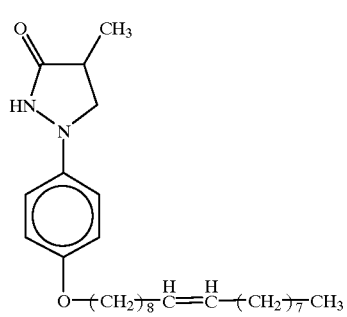
Ph-(28)
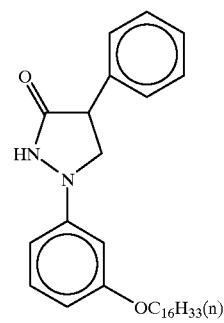
Ph-(29)
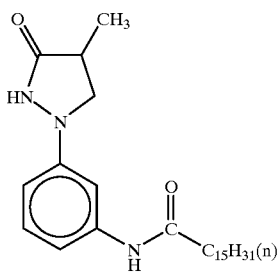
Ph-(30)
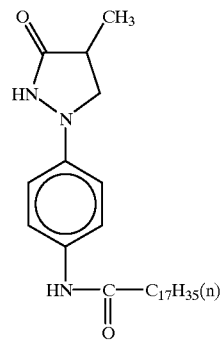
Ph-(31)
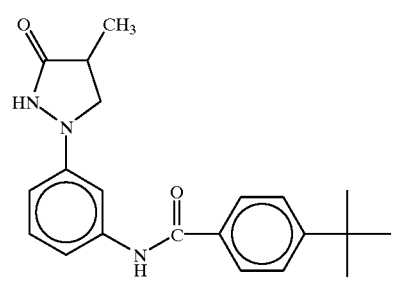
Ph-(32)
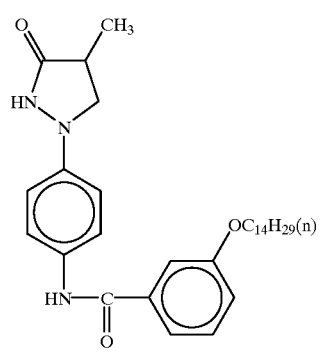
Ph-(33)
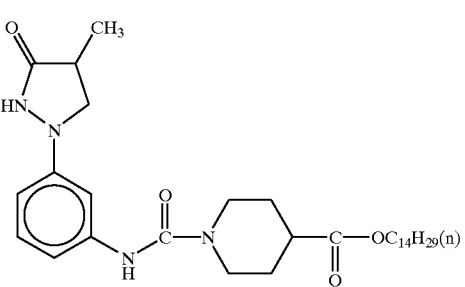
Ph-(34)
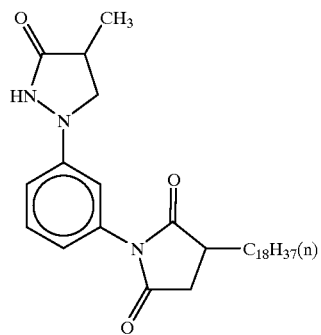

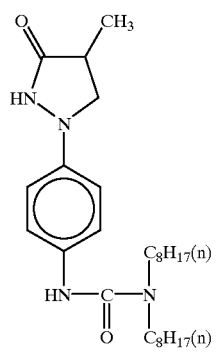
Ph-(35)
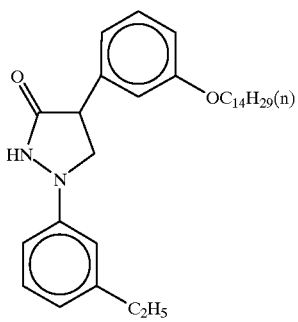
Ph-(36)
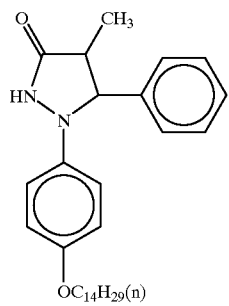
Ph-(37)
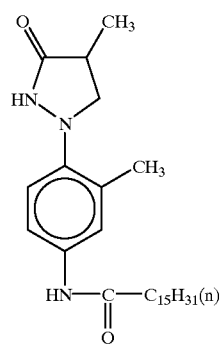
Ph-(38)
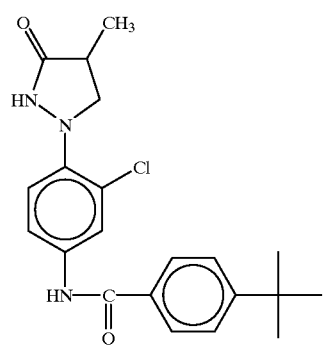
Ph-(39)
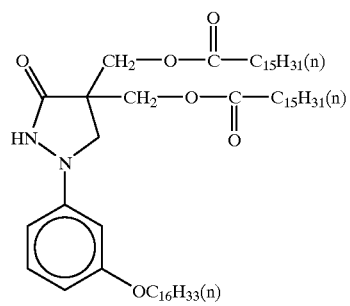
Ph-(40)
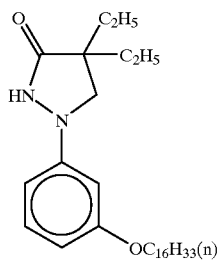
Ph-(41)
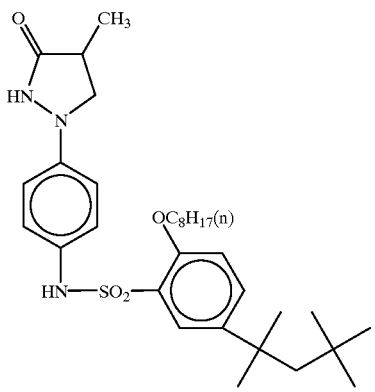
Ph-(42)

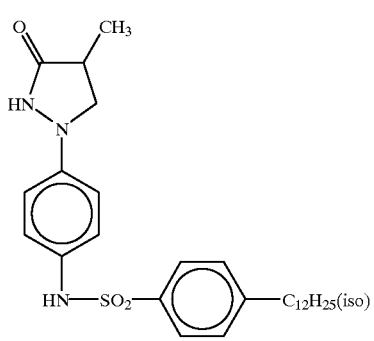
Ph-(43)
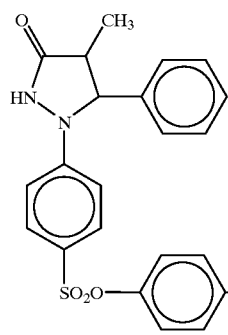
Ph-(47)
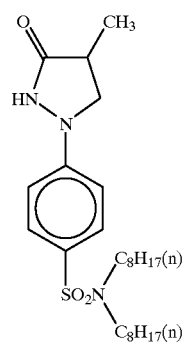
Ph-(44)
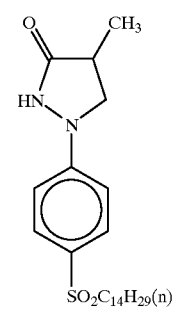
Ph-(48)
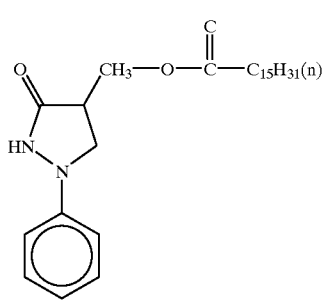
Ph-(45)
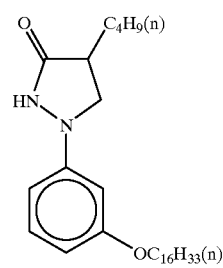
Ph-(49)
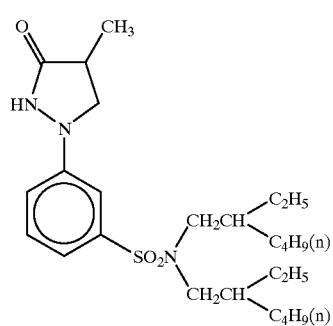
Ph-(46)
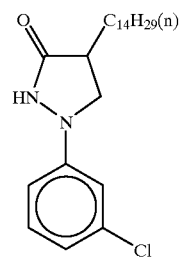
Ph-(50)

Ph-(51)
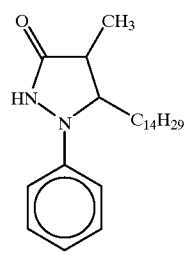
Ph-(56)
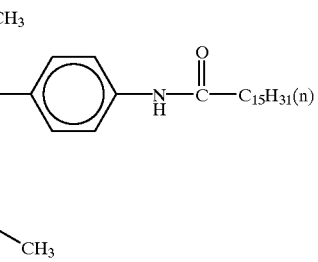
Ph-(52)
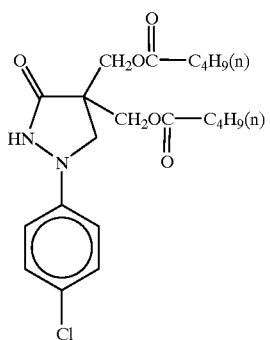
Ph-(57)
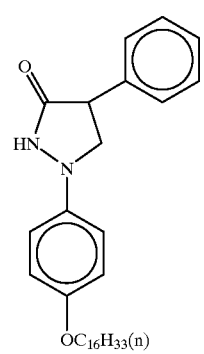
Ph-(53)
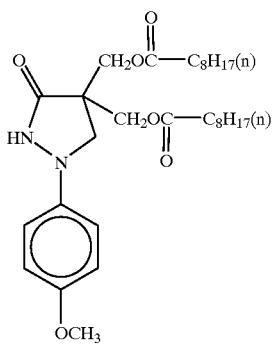
Ph-(58)
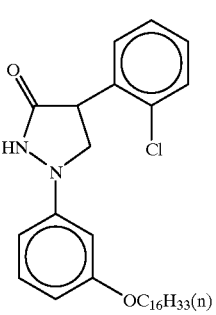
Ph-(54)
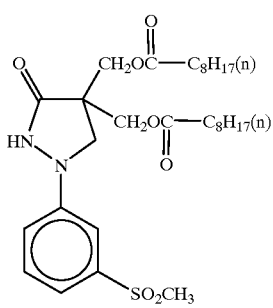
Ph-(59)
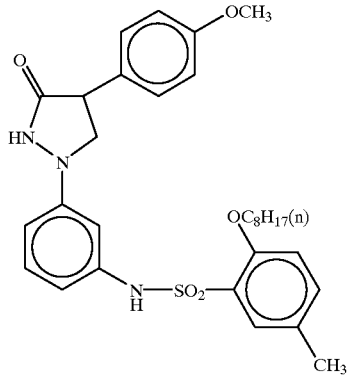
Ph-(55)
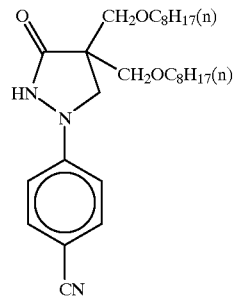
Ph-(60)
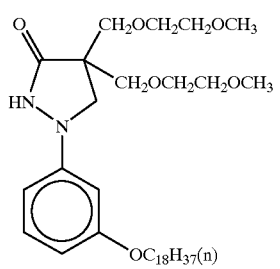

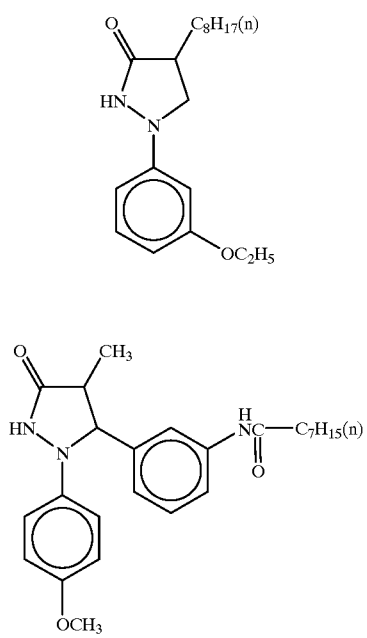
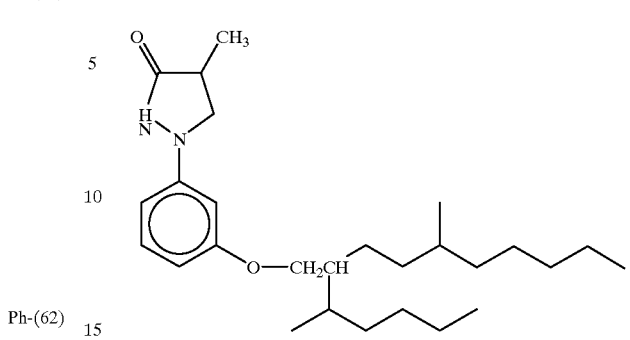
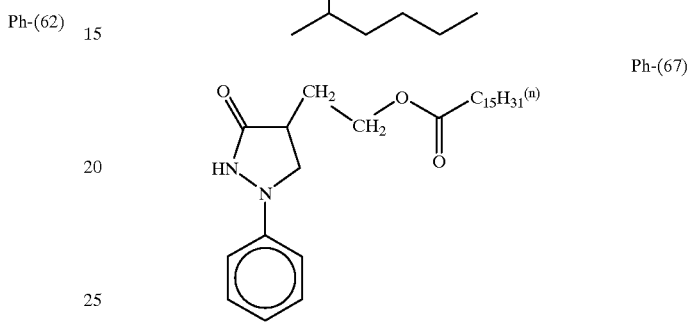
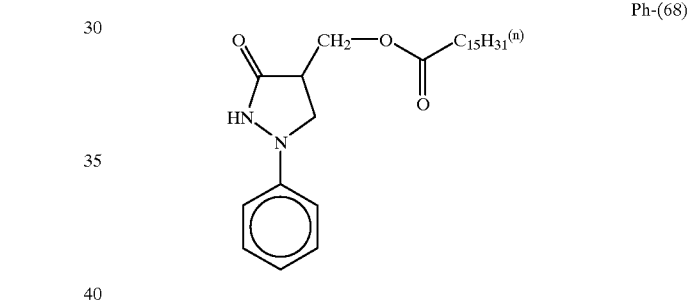
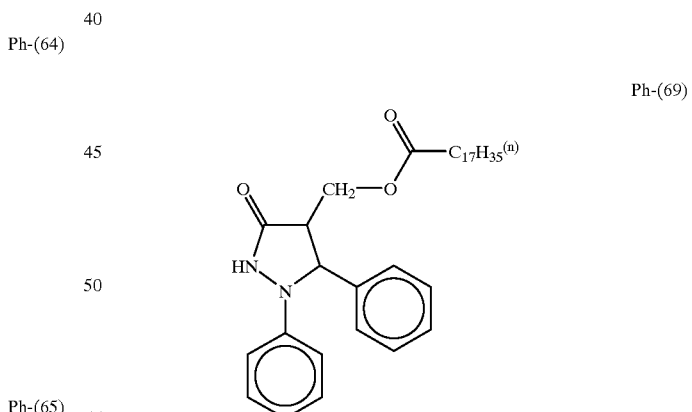
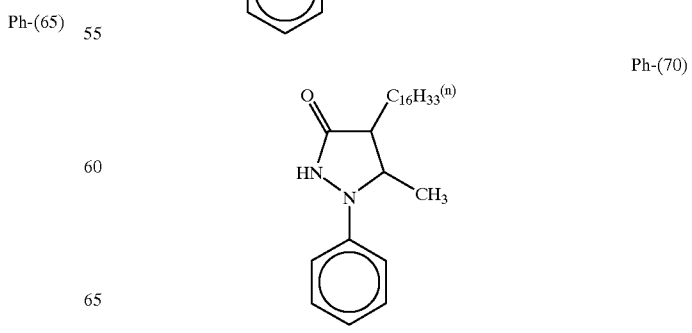
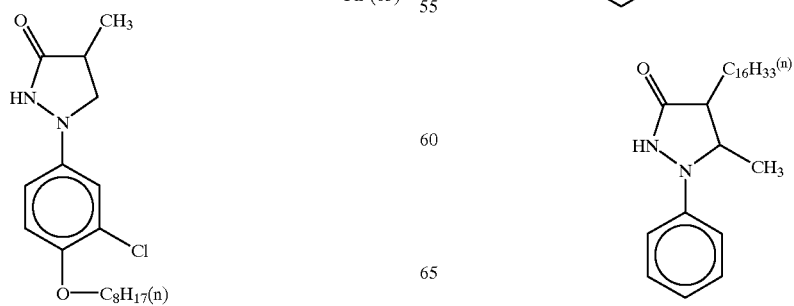

Ph-(71) 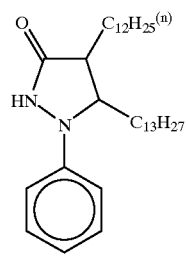
Ph-(72) 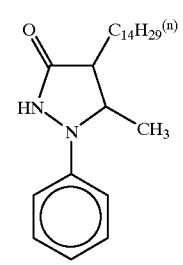
Ph-(73) 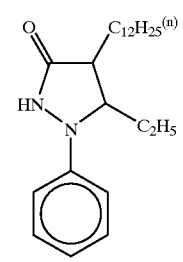
Ph-(74) 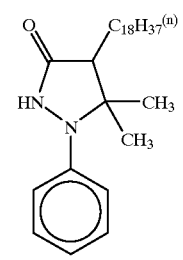
Ph-(75) 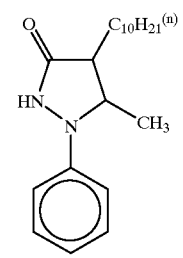
Ph-(76) 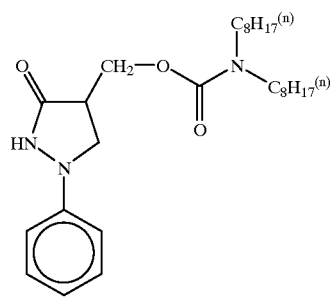
Ph-(77) 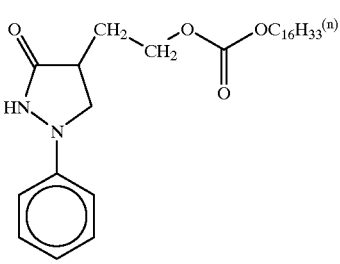
Ph-(78) 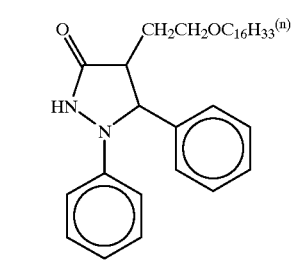
Ph-(79) 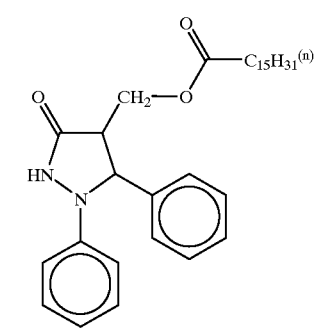
Ph-(80) 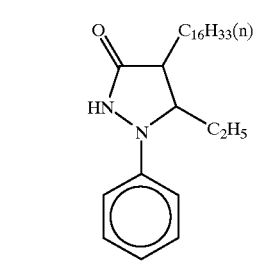
The methods of synthesizing the compounds represented by general formula (B) or (C) are described.
The compound represented by general formula (B) of the present invention can be synthesized according to the following synthetic method:

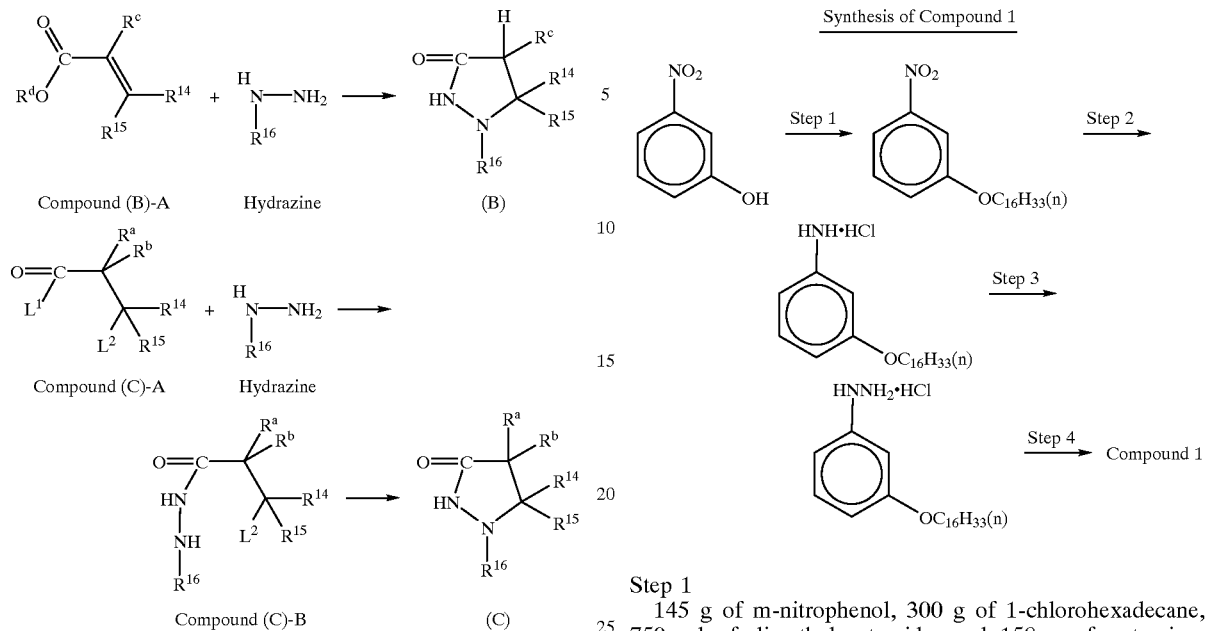

Compound (B)-A and Hydrazine are condensed to form a ring, to synthesize a compound represented by general formula (B). In Compound (B)-A, $R^d$ is an alkyl group or an aryl group, and $R^c$, $R^{14}$, and $R^{15}$ have the same meanings as those of $R^c$, $R^{14}$, and $R^{15}$ of general formula (B). $R^{16}$ of the hydrazine has the same meaning as that of $R^{16}$ of general formula (B).

Preferably, in this reaction, one equivalent or more of a base is permitted to act in a suitable solvent. When a salt of the hydrazine is used, preferably two equivalents or more of a base are used to cause the hydrazine to be free. As the base, an alkoxide is preferable, and potassium t-butoxide, sodium methoxide, and the like exemplify the base. As examples of the solvent, n-butanol, t-butanol, dimethyl sulfoxide, dimethylacetamide, and the like can be mentioned.

The reaction can be carried out under the reaction temperature at generally −20° C. to 180° C., preferably 0° C. to 120° C., and more preferably 30° C. to 90° C.

Generally the reaction time is suitably 5 min to 24 hours, preferably 30 min to 6 hours, and more preferably 1 hour to 3 hours.

Preferably the ratio of the hydrazine and Compound (B)-A to be used is 2:1 to 1:2, and more preferably 1.2:1 to 1:1.2, in terms of molar ratio.

General formula (C)-A and the hydrazine are reacted to synthesize a compound represented by general formula (C). $R^a$, $R^b$, $R^{14}$, and $R^{15}$ in general formula (C)-A have the same meanings as those of $R^a$, $R^b$, $R^{14}$, and $R^{15}$ in general formula (C). $L^1$ and $L^2$ are a group that splits off in a nucleophilic reaction.

Preferably, $L^1$ is a halogen atom, or an oxygen atom activated with a condensation agent. Preferably $L^2$ is a hydroxy group or a halogen atom.

The reaction can be carried out under the reaction temperature at generally −20° C. to 180° C., preferably 0° C. to 120° C., and more preferably 30° C. to 90° C.

Generally the reaction time is suitably 5 min to 24 hours, and preferably 1 hour to 6 hours.

The reaction of (C) from Compound (C)-B is preferably under acid conditions when $L^2$ is a hydroxyl group.

When $L^2$ is a halogen atom, the reaction may be carried out under either neutral, acid or alkaline conditions.

Step 1

145 g of m-nitrophenol, 300 g of 1-chlorohexadecane, 750 ml of dimethylacetamide, and 158 g of potassium carbonate were reacted at 115° C. for 2 hours. The resulting reaction mixture was cooled to 50° C., and thereto 750 ml of acetonitrile was added, and then 200 ml of water was added, dropwise. The deposited crystals were taken out by filtration; they were washed with methanol well, and were dried.

358 g (quantitative) of m-hexadecyloxynitrobenzene was obtained.

Step 2

250 g of m-hexadecyloxynitrobenzene was added to 226 g of reduced iron, 18.05 g of ammonium chloride, 250 g of water, and 2.5 liters of isopropyl alcohol that were being refluxed. After reacting for 30 min, filtration, using Celite as a filtering medium, was carried out, to remove the reduced iron. 58 ml of concentrated hydrochloric acid was added to the filtrate, followed by cooling, for crystallization. The crystals were taken out by filtration, and they were washed with methanol well and dried.

211.8 g of m-hexadecyloxyaminobenzene hydrochloride was obtained (yield: 82.9%).

Step 3

210 g of m-hexadecyloxyaminobenzene hydrochloride and 1.4 liters of acetic acid were stirred, and 80 ml of concentrated hydrochloric acid was added, dropwise, at 20° C. After stirring for 5 min, 86.3 g of isoamyl nitrite was added, dropwise. After reacting for 30 min, a solution of 201 g of tin (II) chloride in 245 ml of concentrated hydrochloric acid was added, dropwise, at 10° C. After reacting for 1 hour at 20° C, 1.4 liters of methanol was added, and crystallization was carried out at 10° C. The crystals were taken out by filtration and were washed with methanol well, to obtain crude crystals. The crude crystals were recrystallized from 800 ml of methanol.

130.2 g of m-hexadecyloxyphenylhydrazine hydrochloride was obtained (yield: 59.6%).

Step 4

83.5 g of potassium-t-butoxide was added to a mixture of 125 g of m-hexadecyloxyphenylhydrazine hydrochloride, 1.5 g of 4-t-butylcatechol, and 625 ml of dimethyl sulfoxide, with the mixture being stirred. After stirring for 10 min, 40.8 g of ethyl methacrylate was added, dropwise. After reacting for 30 min at 45° C., concentrated hydrochloric acid was added to make the pH of the reaction liquid acidic, crystals were deposited; then the crystals were taken out by filtration and were washed with methanol, to obtain crude crystals. The crude crystals were recrystallized from 300 ml of methanol, to obtain 81.2 g (yield: 60.1%) of Compound 1.

The structure of Compound 1 was identified by NMR and mass spectrum. Other compounds of the present invention can easily be synthesized in the same manner.

In the present invention, the cyan coupler represented by general formula (A) and the phenidone compound represented by general formula (B) or (C) are added to the same layer. The phenidone compound is used in an amount to be added of generally 0.1 to 300 mol %, preferably in the range of 5 to 100 mol %, and more preferably in the range of 10 to 30 mol %, to the cyan coupler.

Preferably the cyan coupler of general formula (A) is contained in a silver halide emulsion layer. The amount of silver in the said emulsion layer, to the said cyan coupler can be any value, but, in view of high color-forming property and color reproduction, it is preferably 2.0 or more, but 8.0 or less; more preferably 2.8 or more, but 6.0 or less; and most preferably 2.8 or more, but 5.0 or less. Herein, the ratio of the silver to the cyan coupler is to be defined by the ratio in terms of mole of the silver, to the cyan coupler.

The above cyan coupler is applied on a base generally in an amount of 0.01 to 1 g/m², preferably 0.05 to 0.4 g/m², and more preferably 0.1 to 0.3 g/m².

To introduce the above cyan coupler into a silver halide light-sensitive material, a known dispersion method, such as a latex dispersion method and an oil-in-water dispersion method using a high-boiling organic solvent described later, can be used.

In the oil-in-water dispersion method, the cyan coupler and other photographically useful compounds can be dissolved in a high-boiling organic solvent, and they can be emulsified and dispersed together with a dispersant, such as a surfactant, into a hydrophilic colloid, preferably into an aqueous gelatin solution, to form fine particles by a known apparatus, such as an ultrasonic, a colloid mill, a homogenizer, a Manton-Gaulin, and a high-speed dissolver.

Further, in dissolving the coupler, an auxiliary solvent may be used. Herein, the term "an auxiliary solvent" means an organic solvent useful in emulsifying and dispersing, which can finally be removed substantially from the light-sensitive material after the drying step at the time of applying. Examples of the auxiliary organic solvent include acetates of a lower alcohol, such as ethyl acetate and butyl acetate; ethyl propionate, secondary butyl alcohol, methyl ethyl ketone, methyl isobutyl ketone, β-ethoxyethyl acetate, methyl cellosolve acetate, methyl carbitol acetate, methyl carbitol propionate, and cyclohexanone.

Further, if necessary, an organic solvent that completely admix with water, such as methyl alcohol, ethyl alcohol, acetone, tetrahydrofuran, and dimethylformamide, can be additionally used as a part of the auxiliary solvent. These organic solvents can be used in combination with two or more.

For the purpose of, for example, improving stability with time at storage in the state of an emulsified dispersion, and improving stability with time and inhibiting the change of photographic property of the end-composition for coating (applying) that is mixed with an emulsion, if necessary, from the thus-prepared emulsified dispersion, the auxiliary solvent may be removed in its entirety or part of it, for example, by distillation under reduced pressure, noodle washing, ultrafiltration.

Preferably, the average particle size of the lipophilic fine particle dispersion obtained in this way is 0.04 to 0.50 μm, more preferably 0.05 to 0.30 μm, and most preferably 0.08 to 0.20 μm. The average particle size can be measured by using Coulter Submicron Particle Analyzer Model N4 (Coulter Electronics Co.) or the like.

In the oil-in-water dispersion method that uses a high-boiling organic solvent, the weight ratio of the high-boiling organic solvent to the total weight of couplers to be used can be any weight ratio, but preferably it is 0.1 or more, but 5.0 or less; more preferably 0.3 or more, but 3.0 or less; and most preferably 0.5 or more, but 2.5 or less. The method can be used without using any high-boiling organic solvent at all.

In the color light-sensitive material of the present invention, out of the high-boiling organic solvents that can be used together with the above cyan coupler, in view of the high color-forming property, the color reproduction, and the fastness to light, a compound represented by the below-described general formula [E] can be preferably used.

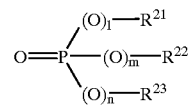

[E]

wherein, in general formula [E], $R^{21}$, $R^{22}$, and $R^{23}$ each represent an acyclic alkyl group, a cycloalkyl group, or an aryl group, and l, m, and n each represent 1 or 0.

The high-boiling organic solvent represented by general formula [E] is described in detail. When $R^{21}$, $R^{22}$, and $R^{23}$ in general formula [E] are an acyclic alkyl group, it may be any of a straight-chain alkyl and a branched-chain alkyl, and it may have an unsaturated bond on the chain, and it may be substituted. As examples of the substituent, can be mentioned a halogen atom, an aryl group, an alkoxy group, an aryloxy group, an alkoxycarbonyl group, a hydroxyl group, an acyloxy group, an epoxy group, and the like. Indeed the substituent is not limited to these and includes a phosphoric acid, a phosphorous acid, a hypophosphite residue, a phosphine oxide residue, and the like represented by the form formed by removing $R^{21}$ from general formula [E].

When $R^{21}$, $R^{22}$, and $R^{23}$ are a cycloalkyl group or a group containing a cycloalkyl group, the cycloalkyl group may be a 3- to 8-membered ring, which may contain an unsaturated bond in the ring, and may have a substituent and a crosslinking group. As examples of the substituent, can be mentioned a halogen atom, an alkyl group, a hydroxyl group, an acyl group, an aryl group, an alkoxy group, an aryloxy group, an alkoxycarbonyl group, an acyloxy group, an epoxy group, and the like. Further, as the crosslinking group, methylene, ethylene, isopropylidene, and the like can be mentioned.

When $R^{21}$, $R^{22}$, and $R^{23}$ are an aryl group or a group containing an aryl group, the aryl group may be substituted by a substituent, such as a halogen atom, an alkyl group, an alkoxy group, an aryloxy group, an alkoxycarbonyl group, an acyloxy group, or the like.

Now, high-boiling organic solvents preferable in the present invention are described. In general formula [E], $R^{21}$, $R^{22}$, and $R^{23}$ are each an acyclic alkyl group having a total number of carbon atoms (hereinafter abbreviated to C-number) from 1 to 24 (more preferably having a C-number of 4 to 18), a cycloalkyl group having a C-number of 5 to 24 (more preferably a C-number of 6 to 18), or an aryl group having a C-number of 6 to 24 (more preferably 6 to 18). As specific examples of the substituted or unsubstituted acyclic alkyl group, can be mentioned an n-butyl group, a 2-ethylhexyl group, a 3,3,5-trimethylhexyl group, an n-dodecyl group, an n-octadecyl group, a benzyl group, an oleyl group, a 2-chloroethyl group, a 2,3-dichloropropyl group, a 2-butoxyethyl group, a 2-phenoxyethyl group, and the like. As specific examples of the cycloalkyl group, can be mentioned a cyclopentyl group, a cyclohexyl group, a 4-t-butylcyclohexyl group, a 4-methylcyclohexyl group, a 2-cyclohexenyl group, and the like. Further, as specific examples of the aryl group, can be mentioned a phenyl group, a cresyl group, a p-nonylphenyl group, a xylyl group, a cumenyl group, a p-methoxyphenyl group, a p-methoxycarbonylphenyl group, a p-isopropylphenyl group, a m-isopropylphenyl group, an o-isopropylphenyl group, a p,o-diisopropylphenyl group, and the like.

Particularly the high-boiling organic solvent represented by general formula [E] is preferably one wherein $R^{21}$, $R^{22}$, and $R^{23}$ represent a substituted or unsubstituted aryl group. Out of them, one wherein $R^{21}$, $R^{22}$, and $R^{23}$ represent an aryl group substituted by an alkyl group is most preferable.

With respect to l, m, and n of the high-boiling organic solvent represented by general formula [E], preferably all of l, m, and n are 1 or at least one of them is 0, and particularly preferably all of l, m, and n are 1. Herein, the high-boiling organic solvent is one having a boiling point of about 150° C. or more and preferably 170° C. or more at normal pressures. The high-boiling organic solvent is not limited to one that is in the state of a liquid at room temperature, but it may be one that is in any state, such as in the state of low-melting crystals, in the state of an amorphous solid, and in the state of a paste, at room temperature. If the high-boiling organic solvent is in the crystalline state at room temperature, preferably the melting point is 100° C. or below, and more preferably 80° C. or below. These high-boiling organic solvents may be used singly or two or more such high-boiling organic solvents may be used as a mixture. When two or more high-boiling organic solvents are used in the form of a mixture, if at least one of them is a high-boiling organic solvent of general formula [E], the others may be any high-boiling organic solvent. As the kind of organic solvents that will be used by mixing, can be mentioned, for example, esters of an aromatic carboxylic acid, such as phthalic acid and benzoic acid; esters of an aliphatic carboxylic acid, such as succinic acid and adipic acid; amide-series compounds, epoxy-series compounds, aniline-series compounds, phenolic compounds, and the like. If the high-boiling organic solvent of general formula [E] is crystalline and has a melting point of 80° C. or more, desirably two or more such high-boiling organic solvents are used as a mixture. When the high-boiling organic solvent of general formula [E] is used by mixing it with another high-boiling organic solvent, preferably the mixing proportion is 25% by weight or more and more preferably 50% by weight or more, if the former is a phosphate. It is preferably 10% by weight or more and more preferably 20% by weight or more, if the former is a phosphonate, a phosphinate, or a phosphine oxide.

Specific examples of the high-boiling organic solvent represented by general formula [E] are listed below, which, of course, does not intend to limit the present invention.

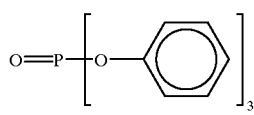
SS-1

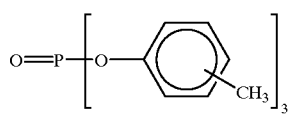
SS-2

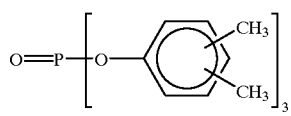
SS-3

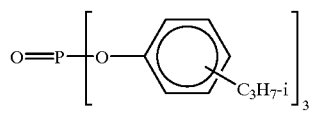
SS-4

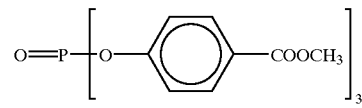
SS-5

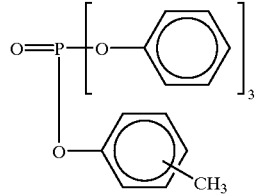
SS-6

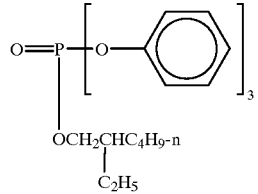
SS-7

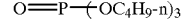
SS-8

SS-9

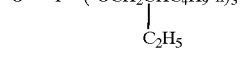
SS-10

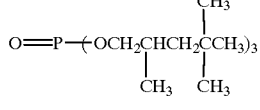
SS-11

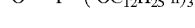
SS-12

SS-13

SS-14

SS-15

SS-16

SS-17

-continued

SS-18, SS-19, SS-20, SS-21, SS-22, SS-23, SS-24, SS-25, SS-26, SS-27, SS-28, SS-29, SS-30, SS-31, SS-32, SS-33, SS-34, SS-35, SS-36, SS-37

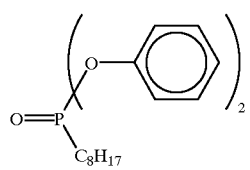 SS-38
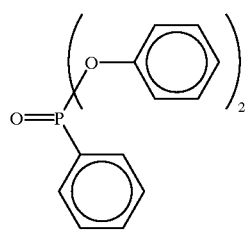 SS-39
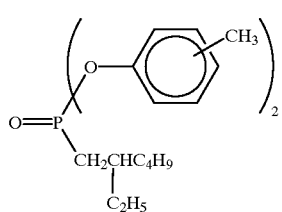 SS-40
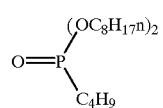 SS-41
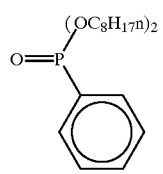 SS-42
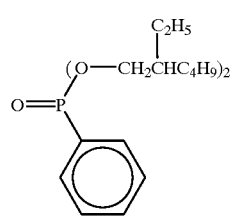 SS-43
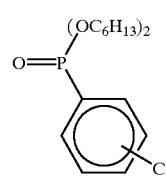 SS-44
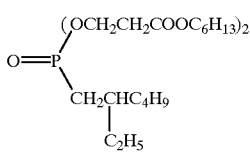 SS-45
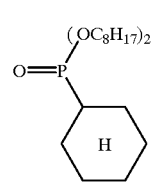 SS-46
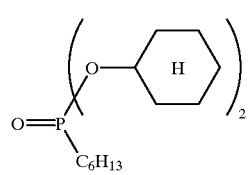 SS-47
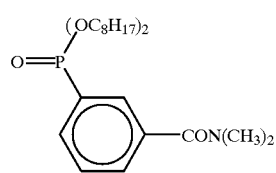 SS-48
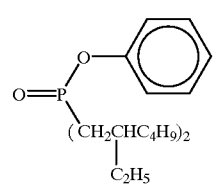 SS-49
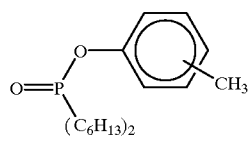 SS-50
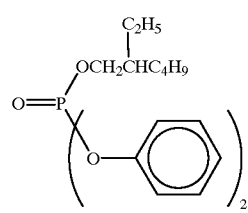 SS-51
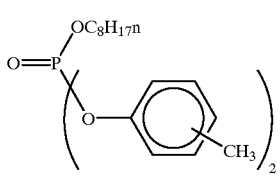 SS-52
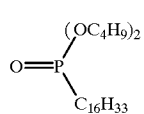 SS-53

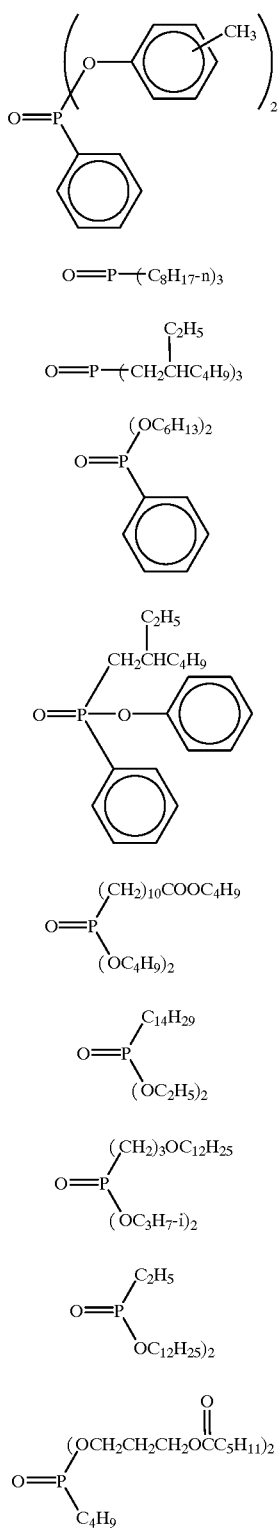

Out of these compounds, particularly SS-4, SS-30, and SS-31 are preferable.

Further, in the present invention, in consideration of the high color-forming property and the improvement in fastness to light, a compound represented by general formula [F] can preferably be used additionally.

General Formula [F]

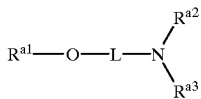

general formula [F]

wherein, in general formula [F], L represents a single bond or an arylene group. $R^{a1}$, $R^{a2}$, and $R^{a3}$, which are the same or different, each represent an alkyl group, an alkenyl group, an aryl group, or a heterocyclic group. When L is a single bond, $R^{a1}$ also represents a radical (.). $R^{a3}$ also represents a hydrogen atom. $R^{a1}$ and L, $R^{a2}$ and L, $R^{a3}$ and L, $R^{a1}$ and $R^{a2}$, $R^{a1}$ and $Ra^3$, and $R^{a2}$ and $Ra^3$ may bond together to form a 5- to 7-membered ring.

The compound represented by general formula [F] is described in detail.

L represents a single bond or an arylene group (e.g., phenylene and naphthylene). $R_{a1}$, $R^{a2}$, and $R^{a3}$, which are the same or different, each represent an alkyl group (a straight-chain, branched-chain, or cyclic alkyl group, e.g., methyl, ethyl, isoprosyl, t-butyl, cyclohexyl, octyl, sec-octyl, t-octyl, decyl, dodecyl, i-tridecyl, tetradecyl, hexadecyl, and octadecyl), an alkenyl group (a straight-chain, branched-chain, or cyclic alkenyl group, e.g., vinyl, allyl, cyclohexenyl, and oleyl), an aryl group (e.g., phenyl and naphthyl), or a heterocyclic group (a 5- to 7-membered heterocyclic group having at least one of N, O, S, and P as a ring constituting atom, e.g., thienyl, furyl, pyranyl, pyrrolyl, imidazolyl, indolyl, chromanyl, and piperidinyl). When L is a single bond, $R^{a1}$ also represents a radical (.). $R^{a3}$ also represents a hydrogen atom. $R^{a1}$ and L, $R^{2a}$ and L, $R^{a3}$ and L, $R^{a1}$ and $R^{2a}$, $R^{a1}$ and $R^{a3}$, and $R^{a2}$ and $R^{a3}$ may bond together to form a 5- to 7-membered ring.

Each of the groups in general formula [F] may be further substituted by a substituent, and, as the substituents, can be mentioned, for example, an alkyl group, an alkenyl group, an aryl group, a heterocyclic group, a halogen atom, a cyano group, a nitro group, a hydroxyl group, an alkoxy group, an alkenoxy group, an aryloxy group, a heterocyclic oxy group, an alkylthio group, an alkenylthio group, an arylthio group, a heterocyclic thio group, an amino group, an alkylamino group, an alkenylamino group, an arylamino group, a heterocyclic amino group, an acylamino group, a sulfonamido group, an acyl group, an acyloxy group, an alkoxycarbonyl group, an alkenoxycarbonyl group, an aryloxycarbonyl group, a heterocyclic-oxycarbonyl group, a sulfonyl group, a sulfinyl group, an alkoxycarbonylamino group, an alkenoxycarbonylamino group, an aryloxycarbonylamino group, a heterocyclic oxycarbonylamino group, a carbamoyl group, a sulfamoyl group, a ureido group, a sulfonyloxy group, a carbamoyloxy group, a sulfamoyloxy group, a phosphoryloxy group, a silyloxy group, and the like.

In general formula [F], preferably L is a single bond or a phenylene group, and more preferably a single bond. Preferably each of $R^{a1}$, $R^{2a}$, and $R^{a3}$ is an alkyl group or an alkenyl group. Preferably the sum of the numbers of carbon atoms of $R^{a1}$, $R^{a2}$, $R^{a3}$, and L is 10 or more, and more preferably 15 or more.

In general formula [F], a more preferable one can be represented by the following general formula [A-I]:

general formula [A-I]

$R^{a1}$—O—$L^{a1}$—N⟨$Z^{a1}$⟩ wherein, in general formula [A-I], $R^{a1}$ has the same meaning as in general formula [F]. $Z^{a1}$ represents a divalent group wherein both the two atoms bonded to the N are carbon atoms and which is a group of non-metal atoms required to form a 5- to 7-membered ring together with the N. $L^{a1}$ represents a single bond or a phenylene group.

Out of the compounds represented by general formula [A-I], most preferable one can be represented by the following general formula [A-II] or [A-III]:

general formula [A-II]

$R^{a4}$—O—N(CH$_3$)(CH$_3$)⟨$Z^{a1}$⟩(CH$_3$)(CH$_3$)

general formula [A-III]

$R^{a1}$—O—⟨phenyl ring with ($R^{a5}$)$_n$⟩—N⟨$Z^{a1}$⟩ wherein, in general formula [A-II] or [A-III], $R^{a1}$ has the same meaning as in general formula [VI]. $R^{a4}$ represents an alkyl group, an alkenyl group, or a radical (.), and $R^{a5}$ represents a substituent. n represents 0 or an integer of 1 to 4. $Z^{a2}$ represents a group of non-metal atoms required to form a 6-membered ring. $Z^{a1}$ has the same meaning as in general formula [A-I].

$Z^{a2}$ in general formula [A-II] is preferably a group required to form a piperidine ring. In general formula [A-III], preferably $R^{a1}$ is an alkyl group or an alkenyl group, and more preferably $R^{a1}$ is in the para position to the ring consisting of N$Z^{a1}$.

Specific examples of the compound represented by general formula [F] that can be used in the present invention are shown below, which do not restrict the scope of the compound.

(a-1) CH$_3$O—N(piperidine with 2,2,6,6-tetramethyl)—OCOC$_{13}$H$_{27}$ (a-2) C$_3$H$_7$O—N(piperidine with 2,2,6,6-tetramethyl)—OCOCH(C$_2$H$_5$)—O—phenyl(2-C$_5$H$_{11}$(t), 4-C$_5$H$_{11}$(t))

(a-3) (sec)C$_4$H$_9$O—N(piperidine with 2,2,6,6-tetramethyl)—OCO—phenyl—N—(C$_8$H$_{17}$(i))$_2$ (a-4) CH$_2$=CH—CH$_2$O—N(piperidine)—OCO—(CH$_2$)$_4$—CO—O—N(piperidine)—OCH$_2$CH=CH$_2$ (a-5) phenyl-CH$_2$—O—N(piperidine)—OCO—(CH$_2$)$_4$—CO—O—N(piperidine)—OCH$_2$-phenyl -continued
(a-6) 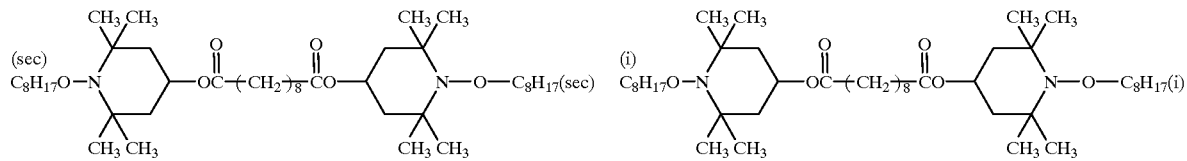 (a-7)
(a-8) 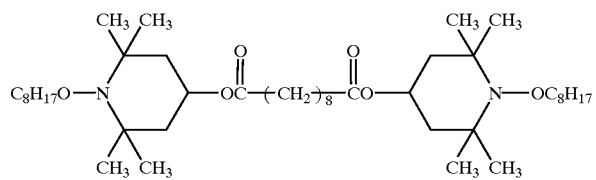
(a-9) 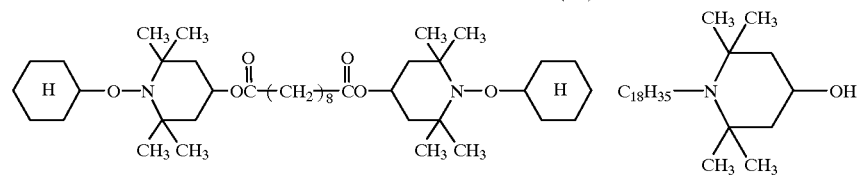 (a-10)
(a-11) 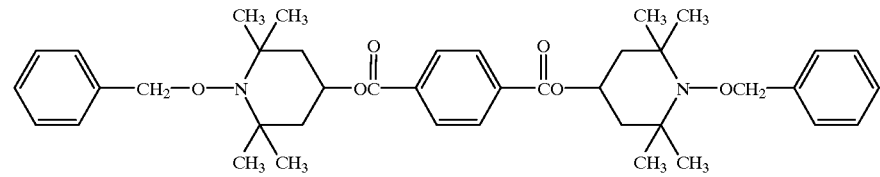
(a-12) 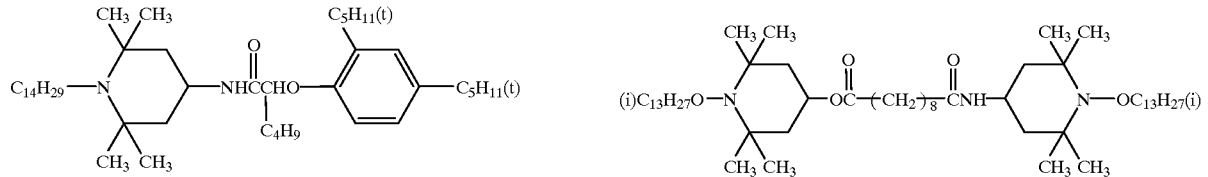 (a-13)
(a-14) 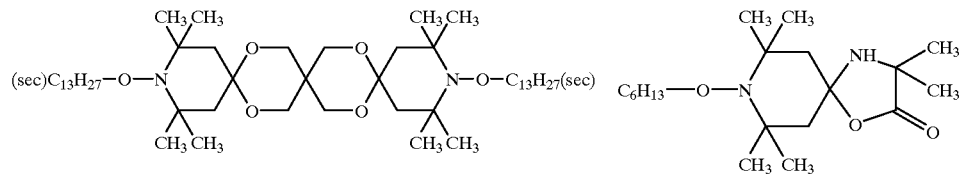 (a-15)
(a-16) 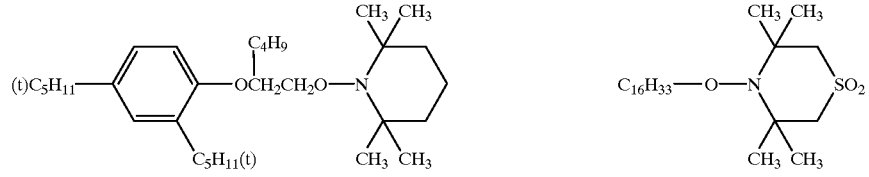 (a-17)
(a-18) 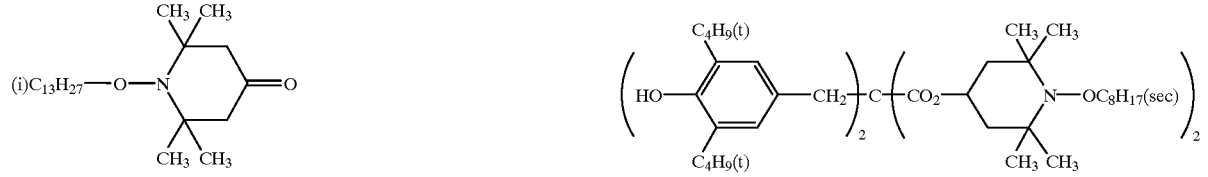 (a-19)

(a-20) 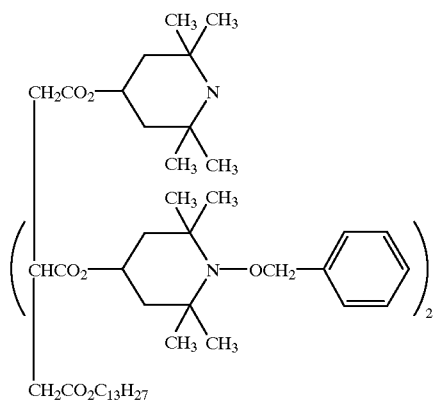
(a-21) 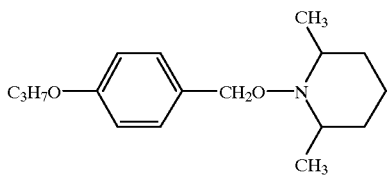
(a-22) 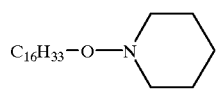
(a-23) 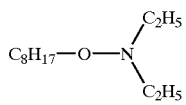
(a-24) 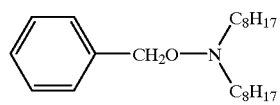
(a-25) 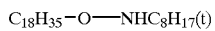
(a-26) 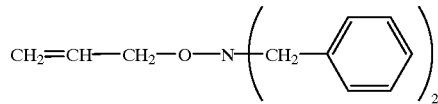
(a-27) 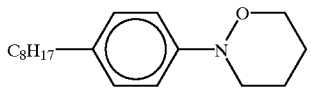
(a-28) 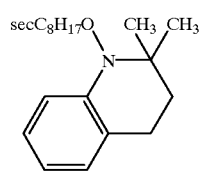
(a-29) 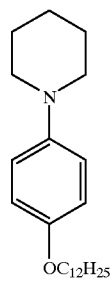
(a-30) 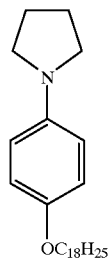
(a-31) 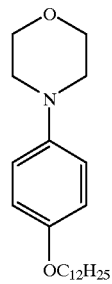

-continued
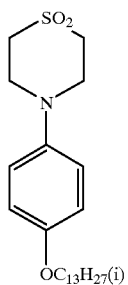 (a-32)
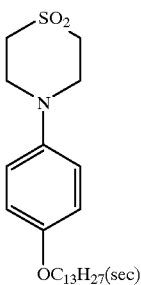 (a-33)
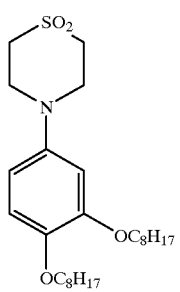 (a-34)
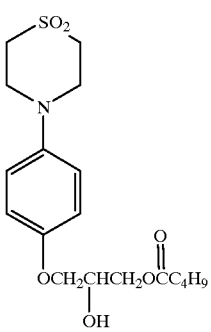 (a-35)
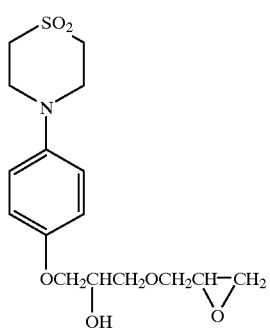 (a-36)
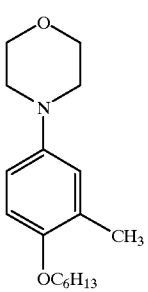 (a-37)
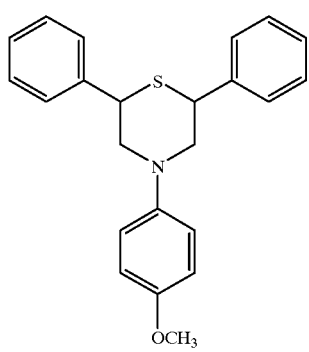 (a-38)
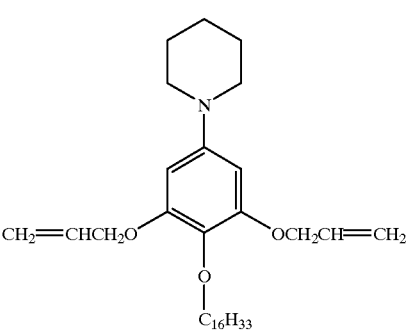 (a-39)

-continued
(a-40)
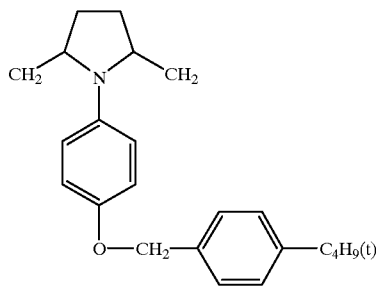
(a-41)
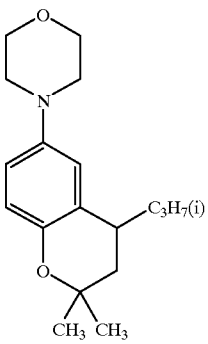
(a-42)
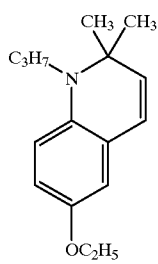
(a-43)
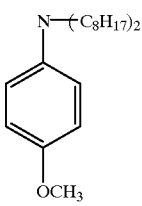
(a-44)
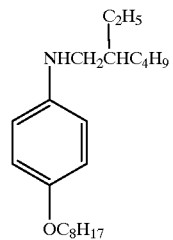
(a-45)
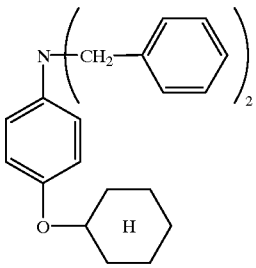
(a-46)
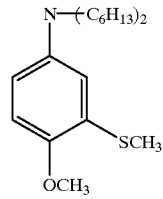
(a-47)
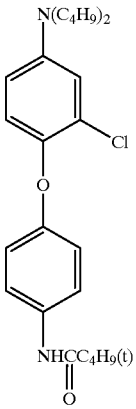
(a-48)
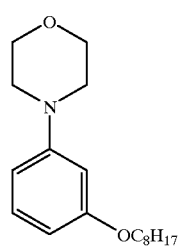
(a-49)
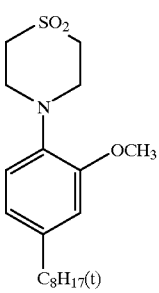

-continued

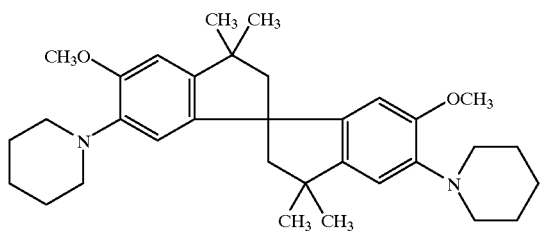
(a-50)

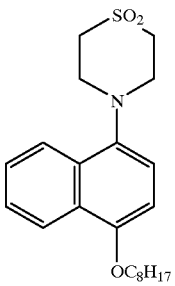
(a-51)

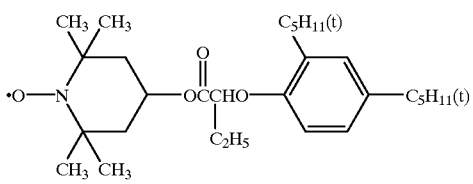
(a-52)

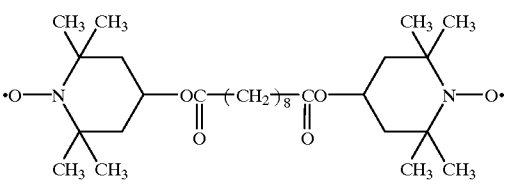
(a-53)

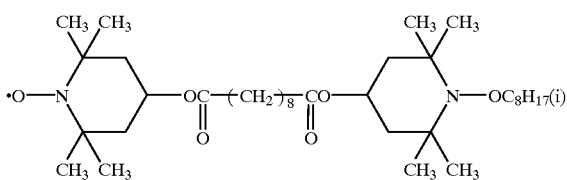
(a-54)

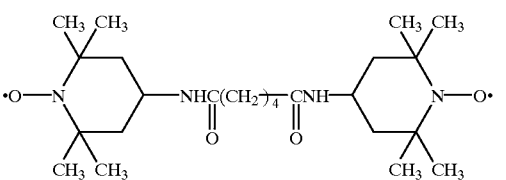
(a-55)

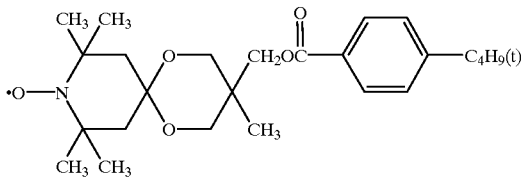
(a-56)

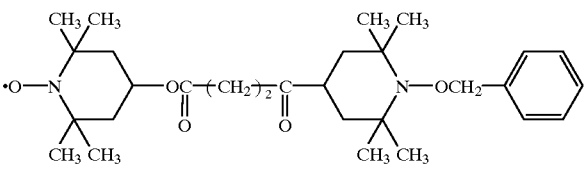
(a-57)

These compounds represented by general formula [F] having an effect for improving fastness of image are added preferably in an amount of 0 to 500 mol %, more preferably 2 to 300 mol %, and most preferably 5 to 200 mol %, to the cyan coupler of general formula (A). These compounds may be used singly or in combination, and they may be added to the same silver halide emulsion layer as that of the cyan coupler, or they may be added to the adjacent layer or another layer.

The compound represented by general formula [F] that can be used in the present invention can easily be synthesized in accordance with methods described, for example, in JP-A-1-132562, JP-A-1-113368, U.S. Pat. Nos. 4,921,962, 4,639,415, and JP-B-6-75175 ("JP-B" means examined Japanese patent publication).

The silver halide photographic light-sensitive material of the present invention can be used for color negative films, color positive films, color reversal films, color reversal photographic printing papers, color photographic printing papers, and the like, and it is preferably used for color photographic printing papers inter alia.

For the silver halide photographic light-sensitive material of the present invention, other conventionally known photographic elements and additives can be used.

For example, as the photographic base (support), a transmission-type base or a reflective-type base can be used. As the transmission-type base, a transparent film, such as a cellulose nitrate film and a polyethylene terephthalate film; and one wherein a film, for example, of a polyester of 2,6-naphthalenedicarboxylic acid (NDCA) with ethylene glycol (EG) or a polyester of NDCA, terephthalic acid, and EG, is provided with an information recording layer, such as a magnetic layer, are preferably used. As a reflective-type base, particularly, a reflective-type base, wherein a laminate has a plurality of polyethylene layers or polyester layers and wherein at least one of such water-resistant resin layers (laminated layers) contains a white pigment, such as titanium oxide, is preferable.

Further, the above water-resistant resin layers preferably contain a fluorescent whitening agent. Further, a fluorescent whitening agent may be dispersed in the hydrophilic colloid layer of the light-sensitive material. As the fluorescent whitening agent, preferably a benzoxazole-series fluorescent whitening agent, a cumarin-series fluorescent whitening agent, or a pyrazoline-series fluorescent whitening agent can be used, and more preferably a benzoxazolylnaphthalene-series fluorescent whitening agent or a benzoxazolylstilbene-series fluorescent whitening agent is used. The amount to be used is not particularly limited, but preferably it is 1 to 100 mg/m². When it is mixed with a water-resistant resin, preferably the mixing proportion is 0.0005 to 3% by weight, and more preferably 0.001 to 0.5% by weight, to the resin.

The reflective-type base may be one wherein a hydrophilic colloid layer containing a white pigment is applied on a transparent-type base or a reflective-type base described in the above.

Further, the reflective-type base may be a base having a specular reflective- or a second-type diffusion reflective metal surface.

In view of the rapid processibility, the silver halide emulsion for use in the present invention is preferably a silver chloride or silver chlorobromide emulsion having a silver chloride content of 95 mol % or more, and more preferably it is a silver halide emulsion having a silver chloride content of 98 mol % ore more. Among such silver halide emulsions, a silver halide emulsion having a silver bromide localized phase on the surface of silver chloride grains are particularly preferable, because a high sensitivity can be obtained and the photographic performance can be stabilized.

For the above reflective-type base, silver halide emulsions, as well as different metal ion species to be doped into silver halide grains, antifoggants or storage stabilizers of silver halide emulsions, chemical sensitizing methods (sensitizers), and spectrally sensitizing methods (spectral sensitizers) for silver halide emulsions, cyan, magenta, and yellow couplers and methods for emulsifying and dispersing them, dye-image-preservability improving agents (antistaining agents and anti-fading agents), dyes (colored layers), gelatins, layer structures of light-sensitive materials, the pH of coatings of light-sensitive materials, and the like, those described in the patents shown in Tables 1 to 2 are preferably applied in the present invention.

TABLE 1

| Element | JP-A-7-104448 | JP-A-7-77775 | JP-A-7-301895 |
|---|---|---|---|
| Reflective-type bases | Column 7, line 12 to Column 12, line 19 | Column 35, line 43 to Column 44, line 1 | Column 5, line 40 to Column 9, line 26 |
| Silver halide emulsions | Column 72, line 29 to Column 74, line 18 | Column 44, line 36 to Column 46, line 29 | Column 77, line 48 to Column 80, line 28 |
| Different metal ion species | Column 74, lines 19 to 44 | Column 46, line 30 to Column 47, line 5 | Column 80, line 29 to Column 81, line 6 |
| Storage stabilizers or antifoggants | Column 75, lines 9 to 18 | Column 47, lines 20 to 29 | Column 18, line 11 to Column 31, line 37 (Especially, mercaptheterocyclic compounds) |
| Chemical sensitizing methods (Chenical sensitizers) | Column 74, line 45 to Column 75, line 6 | Column 47, lines 7 to 17 | Column 81, lines 9 to 17 |
| Spectrally sensitizing methods (Spectrally sensitizers) | Column 75, line 19 to Column 76, line 45 | Column 47, line 30 to Column 49, line 6 | Column 81, line 21 to Column 82, line 48 |
| Cyan couplers | Column 12, line 20 to Column 39, line 49 | Column 62, line 50 to Column 63, line 16 | Column 88, line 49 to Column 89, line 16 |
| Yellow couplers | Column 87, line 40 to Column 88, line 3 | Column 63, lines 17 to 30 | Column 89, lines 17 to 30 |
| Magenta couplers | Column 88, lines 4 to 18 | Coluwn 63, line 31 to Column 64, line 11 | Column 32, line 34 to Column 77, line 44 and column 89, lines 32 to 46 |
| Emulsifying and dispersing methods of couplers | Column 71, line 3 to Column 72, line 11 | Column 61, lines 36 to 49 | Column 87, lines 35 to 48 |

TABLE 2

| Element | JP-A-7-104448 | JP-A-7-77775 | JP-A-7-301895 |
|---|---|---|---|
| Dye-image-preservability improving agents (antistaining agents) | Column 39, line 50 to Column 70, line 9 | Column 61, line 50 to Column 62, line 49 | Column 87, line 49 to Column 88, line 48 |
| Anti-fading agents | Column 70, line 10 to Column 71, line 2 | | |
| Dyes (colored layers) | Column 77, line 42 to Column 78, line 41 | Column 7, line 14 to Column 19, line 42, and Column 50, line 3 to Column 51, line 14 | Column 9, line 27 to Column 18, line 10 |
| Geratins | Column 78, lines 42 to 48 | Column 51, lines 15 to 20 | Column 83, lines 13 to 19 |
| Layer construction of light-sensitive materials | Column 39, lines 11 to 26 | Column 44, lines 2 to 35 | Column 31, line 38 to Column 32, line 33 |
| pH of coatings of light-sensitive material | Column 72, lines 12 to 28 | | |
| Scanning exposure | Column 76, line 6 to Column 77, line 41 | Column 49, line 7 to Column 50, line 2 | Column 82, line 49 to Column 83, line 12 |
| Preservatives in developing solution | Column 88, line 19 to Column 89, line 22 | | |

As the cyan, magenta, and yellow couplers additionally used in the present invention, further, couplers described in JP-A-62-215272, page 91, right upper column, line 4 to page 121, left upper column, line 6; JP-A-2-33144, page 3 right upper column, line 14 to page 18, left upper column, the last line, and page 30, right upper column, line 6 to page 35, right lower column, line 11; and EP-A-0 355 660 (A2), page 4, line 15 to line 27, page 5, line 30 to page 28, the last line, page 45, line 29 to line 31, and page 47, line 23 to page 63, line 50, are also useful.

As fungiproofing/mildewproofing agents that can be used in the present invention, those described in JP-A-63-271247 are useful. As a hydrophilic colloid used in photographic layers that constitute the light-sensitive material, gelatin is preferable, and in particular, heavy metals contained as impurities, such as iron, copper, zinc, and manganese are 5 ppm or less and more preferably 3 ppm or less.

The light-sensitive material of the present invention is for use in not only printing systems that use usual negative printers, it is also suitable for scanning exposure systems using cathode rays (CRT).

In comparison with apparatuses using lasers, cathode ray tube exposure apparatuses are simple and compact and make the cost low. Further, the adjustment of optical axes and colors is easy.

For the cathode ray tubes used for image exposure, use is made of various emitters that emit light in spectral regions as required. For example, any one of, or a mixture of two or more of, a red emitter, a green emitter, and a blue emitter may be used. The spectral region is not limited to the above red, green, and blue, and an emitter that emits a color in the yellow, orange, purple, or infrared region may also be used. In particular, a cathode ray tube that emits white light by mixing these phosphors is often used.

When the light-sensitive material has multiple light-sensitive layers different in spectral sensitivity distributions, and the cathode ray tube has phosphors that show light emission in multiple spectral regions, multiple colors may be exposed at a time; namely, image signals of multiple colors are inputted into the cathode ray tube, to emit lights from the tube surface. A method in which exposure is made in such a manner that image signals for respective colors are inputted successively, to emit the respective colors successively, and they are passed through films for cutting out other colors (surface-successive exposure), may be employed, and generally the surface-successive exposure is preferred to make image quality high, since a high-resolution cathode ray tube can be used.

The light-sensitive material of the present invention is preferably used for digital scanning exposure system that uses monochromatic high-density light, such as a second harmonic generating light source (SHG) that comprises a combination of a nonlinear optical crystal with a semiconductor laser or a solid state laser using a semiconductor laser as an excitation light source, a gas laser, a light-emitting diode, or a semiconductor laser. To make the system compact and inexpensive, it is preferable to use a semiconductor laser or a second harmonic generating light source (SHG) that comprises a combination of a nonlinear optical crystal with a semiconductor laser or a solid state laser. Particularly, to design an apparatus that is compact, inexpensive, long in life, and high in stability, the use of a semiconductor laser is preferable, and it is preferable to use a semiconductor laser for at least one of the exposure light sources.

If such a scanning exposure light source is used, the spectral sensitivity maximum wavelength of the light-sensitive material of the present invention can arbitrarily be set by the wavelength of the light source for the scanning exposure to be used. In an SHG light source obtained by combining a nonlinear optical crystal with a semiconductor laser or a solid state laser that uses a semiconductor laser as an excitation light source, since the emitting wavelength of the laser can be halved, blue light and green light can be obtained. Therefore, the spectral sensitivity maximum of the light-sensitive material can be present in each of the usual three wavelength regions, the blue region, the green region and the red region.

If the exposure time in this scanning exposure is defined as the time for which a picture element size is exposed to light with the density of the picture element being 400 dpi, preferably the exposure time is $10^{-4}$ sec or less, more preferably $10^{-6}$ sec or less.

Preferable scanning exposure systems that can be applied to the present invention are described in detail in the patents listed in the above Tables.

Further, to process the light-sensitive material of the present invention, processing materials and processing methods described in JP-A-2-207250, page 26, right lower column, line 1, to page 34, right upper column, line 9, and in JP-A-4-97355, page 5, left upper column, line 17, to page 18, right lower column, line 20, are preferably applied. Further, as the preservative used for this developing solution, compounds described in the patents listed in the above Tables are preferably used.

As the systems for developing the light-sensitive material of the present invention after the exposure thereof, a wet system, such as the conventional method, in which development is carried out by using a developing solution containing an alkali agent and a developing agent, and a method in which a developing agent is built in the light-sensitive material and the development is carried out by using an activator solution, such as an alkali solution, free from any developing agent, as well as a heat development system that does not use a processing solution, can be used. Particularly, since the activator method does not contain a developing agent in the processing solution, the control and the handling of the processing solution are easy, and the load at the time of waste liquor treatment is less, which makes the activator method preferable in view of environmental conservation.

In the activator method, as the developing agent or its precursor to be built in the light-sensitive material, hydrazine-type compounds described, for example, in Japanese Patent Application Nos. 7-63572, 7-334190, 7-334192, 7-334197, and 7-344396 are preferable.

Further, a development method in which the coated amount of silver in the light-sensitive material is decreased, and an image intensification processing (intensification processing) is carried out using hydrogen peroxide, is also preferably used. Particularly, it is preferable to use this method for the activator method. Specifically, preferably use is made of image-forming methods described in Japanese Patent Application Nos. 7-63587 and 7-334202, wherein an activator solution containing hydrogen peroxide is used.

Although, in the activator method, after the processing with an activator solution, a desilvering process is generally carried out, in the image intensifying process in which a light-sensitive material with the amount of silver lowered is used, the desilvering process can be omitted, and a simple process, such as a washing process or a stabilizing process, can be carried out. Further, in a system in which image information is read from a light-sensitive material by a scanner or the like, a processing mode without requiring a desilvering process can be employed, even when a light-sensitive material having a large amount of silver, such as a light-sensitive material for shooting (photographing), is used.

As the activator solution, the desilvering solution (bleach/fix solution), the processing material of washing and stabilizing solution, and the processing method that are used in the present invention, known ones can be used. Preferably, those described in Research Disclosure Item 36544 (September 1994), pages 536 to 541, and Japanese Patent Application No. 7-63572, can be used.

EXAMPLES

Now, the present invention will be described in more detail with reference to examples, but the present invention is not restricted to the examples.

Example 1

A paper base whose both surfaces had been laminated with a polyethylene, was subjected to surface corona discharge treatment; it was then provided with a gelatin undercoat layer containing sodium dodecylbenzenesulfonate, and it was coated with various photographic constitutional layers, to prepare a multi-layer color printing paper (101) having the layer constitution shown below.

The coating solutions were prepared as follows.
Preparation of Fifth-Layer Coating Solution 10 g of a cyan coupler (Cp-1) of general formula (A) was dissolved in 30 g of a solvent (Solv-8) and 50 ml of ethyl acetate, and the resultant solution was emulsified and dispersed in 400 g of a 12% aqueous gelatin solution containing 1.2 g of a surface active agent (Cpd-12), to prepare an emulsion C having average grain size of 0.18 μm.

On the other hand, a silver chlorobromide emulsion C (cubes, a mixture of a large-size emulsion C having an average grain size of 0.55 μm, and a small-size emulsion C having an average grain size of 0.42 μm (1:4 in terms of mol of silver), the deviation-coefficients of the grain size distributions being 0.09 and 0.11 respectively, and each emulsion having 0.8 mol % of silver bromide locally contained in part of the grain surface whose substrate was made up of silver chloride) was prepared. To the large-size emulsion C of this emulsion, had been added $5.0 \times 10^{-5}$ mol, per mol of silver, of each of red-sensitive sensitizing dyes G, and H shown below, and to the small-size emulsion C of this emulsion, had been added $8.0 \times 10^{-5}$ mol, per mol of silver, of each of red-sensitive sensitizing dyes G, and H shown below. Further, $2.6 \times 10^{-3}$ mol, per mol of silver halide, of an additive X was added. The chemical ripening of this emulsion was carried out optimally with a sulfur sensitizer and a gold sensitizer being added.

The above emulsified dispersion C and this silver chlorobromide emulsion C were mixed and dissolved, and a fifth-layer coating solution was prepared so that it would have the composition shown below. The coating amount of the emulsion is in terms of silver.

The coating solutions for the first layer to seventh layer were prepared in the similar manner as that for the fifth layer coating solution. These coating solutions were coated within 15 minutes after the preparation. As the gelatin hardener for each layer, 1-oxy-3,5-dichloro-s-triazine sodium salt was used.

Further, to each layer, were added antiseptics AS-1, AS-2, AS-3, and AS-4, so that the total amounts would be 15.0 mg/m², 6.0 mg/m², 5.0 mg/m², and 10.0 mg/m², respectively.

(AS-1) Antiseptic

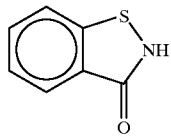

(AS-2) Antiseptic

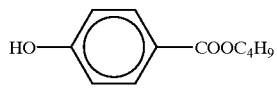

(AS-3) Antiseptic

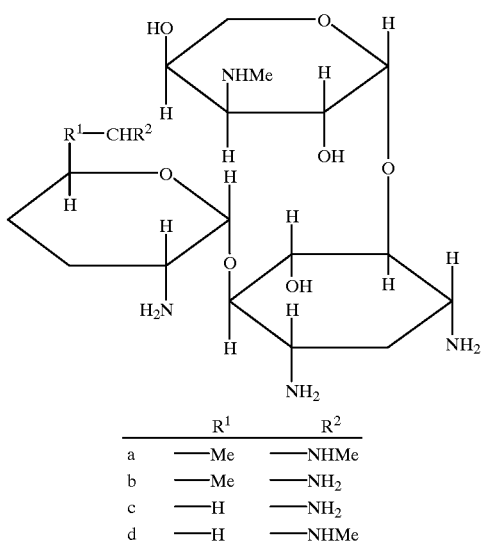

| | $R^1$ | $R^2$ |
|---|---|---|
| a | —Me | —NHMe |
| b | —Me | —$NH_2$ |
| c | —H | —$NH_2$ |
| d | —H | —NHMe |

A mixture in 1:1:1:1 (weight ratio) of a, b, c and D (AS-4) Antiseptic

For the silver chlorobromide emulsion of each photosensitive emulsion layer, the following spectral sensitizing dyes were used.
Blue-sensitive emulsion layer Sensitizing dye A Sensitizing dye B Sensitizing dye C (The sensitizing dyes were added, respectively, to the large-size emulsion, in an amount of $1.4 \times 10^{-4}$ mol per mol of the silver halide, and to the small-size emulsion in an amount of $1.7 \times 10^{-4}$ per mol of the silver halide.)

Green-sensitive Emulsion Layer

Sensitizing dye D

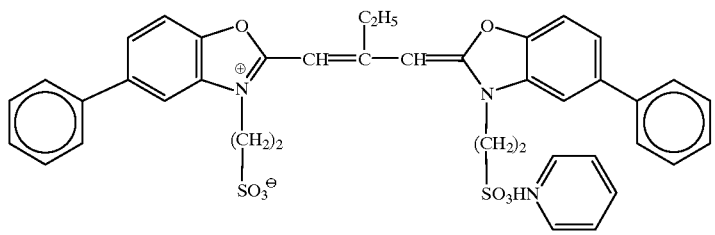

Sensitizing dye E

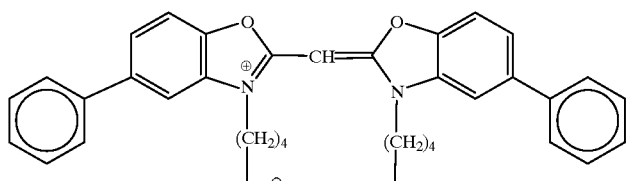

Sensitizing dye F

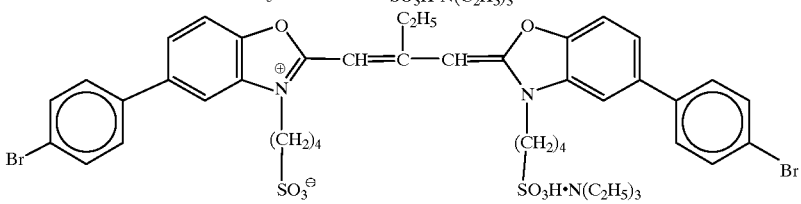

(The sensitizing dye D was added to the large-size emulsion in an amount of $3.0\times10^{-4}$ mol per mol of the silver halide, and to the small-size emulsion in an amount of $3.6\times10^{-4}$ mol per mol of the silver halide; the sensitizing dye E was added to the large-size emulsion in an amount of $4.0\times10^{-5}$ mol per mol of the silver halide, and to the small-size emulsion in an amount of $7.0\times10^{-5}$ mol per mol of the silver halide; and the sensitizing dye F was added to the large-size emulsion in an amount of $2.0\times10^{-4}$ mol per mol of the silver halide, and to the small-size emulsion in an amount of $2.8\times10^{-4}$ mol per mol of the silver halide.)

Red-sensitive emulsion layer

Sensitizing dye G

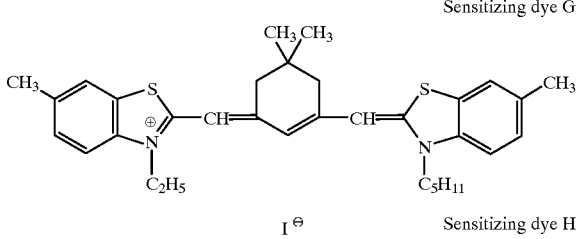

Sensitizing dye H

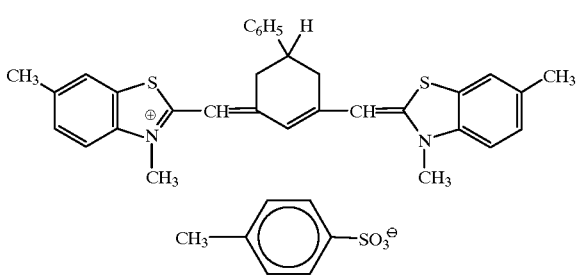

(The sensitizing dyes were added, respectively, to the large-size emulsion, in an amount of $5.0\times10^{-5}$ mol per mol of the silver halide, and to the small-size emulsion in an amount of $8.0\times10^{-5}$ per mol of the silver halide.

Further, the following additive X was added in the red-sensitive emulsion layer in an amount of $2.6\times10^{-3}$ mol per mol of the silver halide.

Additive X

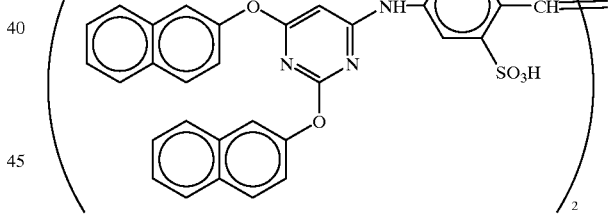

Further, to the blue-sensitive emulsion layer, the green-sensitive emulsion layer, and the red-sensitive emulsion layer, was added 1-(5-methylureidophenyl)-5-mercaptotetrazole in amounts of $3.3\times10^{-4}$ mol, $1.0\times10^{-3}$ mol, and $5.9\times10^{-4}$ mol, per mol of the silver respectively.

Further, to the second layer, the fourth layer, the sixth layer, and the seventh layer, it was added in amounts of 0.2 mg/m$^2$, 0.2 mg/m$^2$, 0.6 mg/m$^2$, and 0.1 mg/m$^2$, respectively.

Further, to the blue-sensitive emulsion layer and the green-sensitive emulsion layer, was added 4-hydroxy-6-methyl-1,3,3a,7-tetrazaindene in amounts of $1\times10^{-4}$ mol and $2\times10^{-4}$ mol, respectively, per mol of the silver halide.

Further, as irradiation-neutralizing water-soluble dyes, the following compounds were added, with dividing them up, to the second layer, the fourth layer, and the sixth layer.

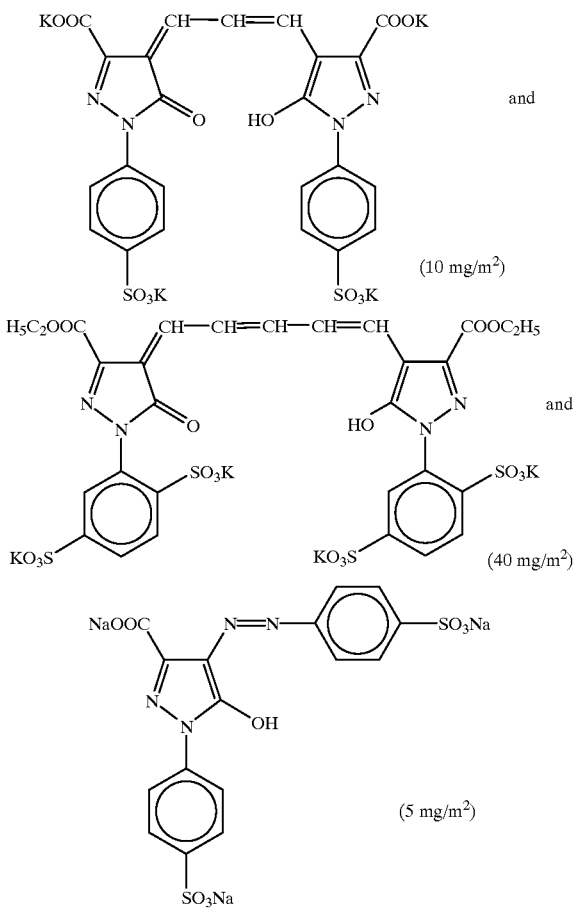

(10 mg/m²)

(40 mg/m²)

(5 mg/m²)

(Layer Constitution)

The composition of each layer is shown below. The numbers show coating amounts (g/m²). In the case of the silver halide emulsion, the coating amount is in terms of silver.

Base

Polyethylene Laminated Paper

[The polyethylene on the first layer side contained a white pigment (TiO$_2$: content of 15 wt %), and a blue dye (ultramarine)]

First Layer (Blue-Sensitive Emulsion Layer)

| | |
|---|---|
| A silver chlorobromide emulsion A: cubes, a mixture of a large-size emulsion A having an average grain size of 0.88 μm and a small-size emulsion A having an average grain size of 0.70 μm (3:7 in terms of mol of silver). The deviation coefficients of the grain size distributions were 0.08 and 0.10, respectively, and each emulsion had 0.3 mol % of silver bromide locally contained in part of the grain surface whose substrate was made up of silver chloride. | 0.26 |
| Gelatin | 1.4 |
| Yellow coupler (EXY) | 0.64 |
| Color-image stabilizer (Cpd-1) | 0.078 |
| Color-image stabilizer (Cpd-2) | 0.038 |
| Color-image stabilizer (Cpd-3) | 0.085 |
| Color-image stabilizer (Cpd-5) | 0.020 |
| Color-image stabilizer (Cpd-9) | 0.0050 |

-continued

| | |
|---|---|
| Solvent (Solv-1) | 0.11 |
| Solvent (Solv-6) | 0.11 |

Second Layer (Color-Mixing Inhibiting Layer)

| | |
|---|---|
| Gelatin | 1.0 |
| Color-mixing inhibitor (Cpd-4) | 0.11 |
| Solvent (Solv-1) | 0.065 |
| Solvent (Solv-2) | 0.22 |
| Solvent (Solv-3) | 0.080 |
| Solvent (Solv-7) | 0.010 |
| Ultravioiet absorbing agent (UV-B) | 0.070 |

Third Layer (Green-Sensitive Emulsion Layer)

| | |
|---|---|
| A silver chlorobromide emulsion: cubes, a mixture of a large-size emulsion B having an average grain size of 0.55 μm, and a small-size emulsion B having an average grain size of 0.39 μm (1:3 in terms of mol of silver). The deviation coefficients of the grain size distributions were 0.10 and 0.08, respectively, and each emulsion had 0.7 mol % of silver bromide locally contained in part of the grain surface whose substrate was made up of silver chloride. | 0.11 |
| Gelatin | 1.3 |
| Magenta coupler (ExM) | 0.13 |
| Ultraviolet absorbing agent (UV-A) | 0.12 |
| Color-image stabilizer (Cpd-2) | 0.010 |
| Color-image stabilizer (Cpd-5) | 0.020 |
| Color-image stabilizer (Cpd-6) | 0.010 |
| Color-image stabilizer (Cpd-7) | 0.080 |
| Color-image stabilizer (Cpd-8) | 0.030 |
| Color-image stabilizer (Cpd-10) | 0.0020 |
| Solvent (Solv-3) | 0.15 |
| Solvent (Solv-4) | 0.22 |
| Solvent (Solv-5) | 0.11 |

Fourth Layer (Color-Mixing Inhibiting Layer)

| | |
|---|---|
| Gelatin | 1.0 |
| Color-mixing inhibitor (Cpd-4) | 0.11 |
| Solvent (Solv-1) | 0.065 |
| Solvent (Solv-2) | 0.22 |
| Solvent (Solv-3) | 0.080 |
| Solvent (Solv-7) | 0.010 |
| Ultraviolet absorbing agent (UV-B) | 0.070 |

Fifth Layer (Red-Sensitive Emulsion Layer)

| | |
|---|---|
| A silver chlorobromide emulsion: cubes, a mixture of a large-size emulsion having an average grain size of 0.55 μm, and a small-size emulsion having an average grain size of 0.42 μm (1:4 in terms of mol of silver). The deviation coefficients of the grain size distributions were 0.09 and 0.11, respectively, and each emulsion had 0.8 mol % of silver bromide locally contained in part of the grain surface whose substrate was made up of silver chloride. | 0.086 |

-continued

| | |
|---|---|
| Surface-active agent (Cpd-12) | 0.006 |
| Gelatin | 0.99 |
| Cyan coupler of general formula (I) | |
| (Exemplified compound Cp-1) | 0.15 |
| Solvent (Solv-8) | 0.45 |

Sixth Layer (Ultraviolet Absorbing Layer)

| | |
|---|---|
| Gelatin | 0.63 |
| Ultraviolet absorbing agent (UV-C) | 0.35 |

-continued

| | |
|---|---|
| Color-image stabilizer (Cpd-7) | 0.050 |
| Solvent (Solv-9) | 0.050 |

Seventh Layer (Protective Layer)

| | |
|---|---|
| Acid-processed gelatin | 1.0 |
| Acryl-modified copolymer of polyvinyl alcohol (modification degree: 17%) | 0.043 |
| Liquid paraffin | 0.018 |
| Surface-active agent (Cpd-11) | 0.026 |

(ExY) Yellow coupler (ExY-1)

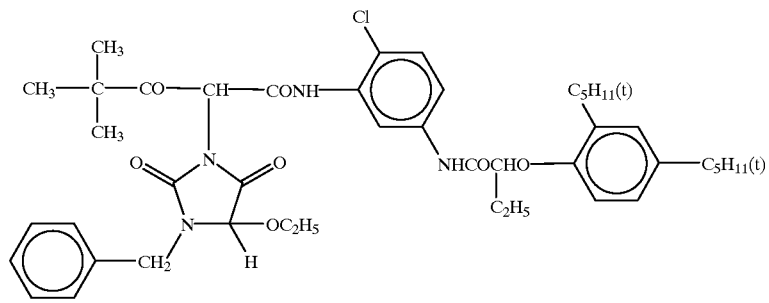

(ExY-2)  (ExY-3)

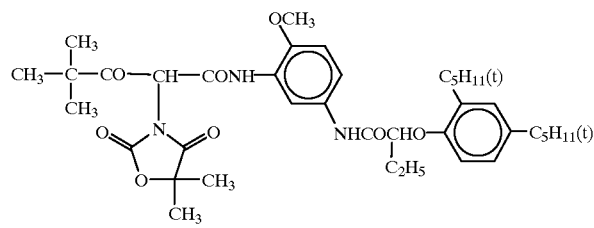 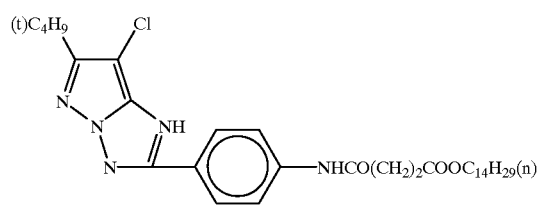

A mixture in a molar ratio of 1:1:1

(ExM) Magenta coupler (ExM-1)  (ExM-2)

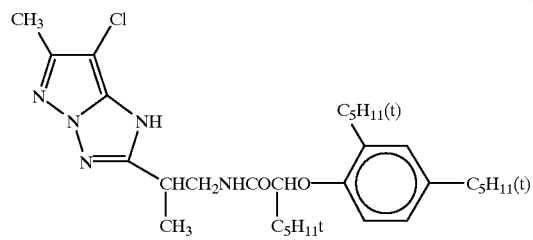

A mixture in a molar ratio of 1:5

(Cpd-1) Color-image stabilizer

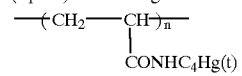

number average molecular weight 60,000

(Cpd-2) Color-image stabilizer

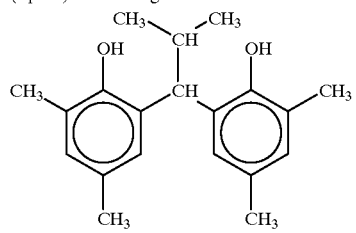

-continued (Cpd-3) Color-image stabilizer

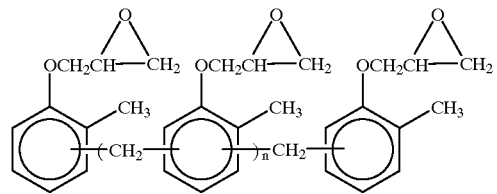

(n = 0–15, average value 7–8)

(Cpd-4) Color-image inhibitor
A mixture in 1:1:1 in weight ratio of

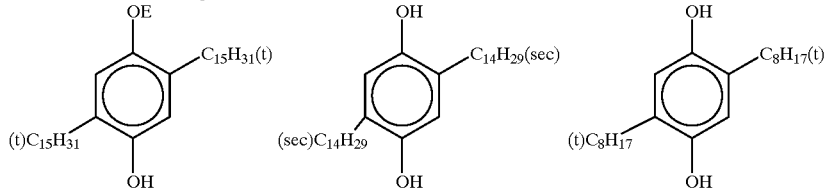

(Cpd-5) Color-image stabilizer

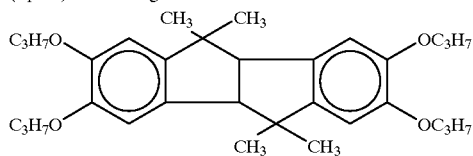

(Cpd-6) Color-image stabilizer (Cpd-7) Color-image stabilizer

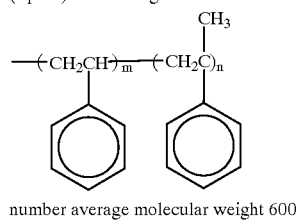

number average molecular weight 600
m/n = 10/90

(Cpd-8) Color-image stabilizer (Cpd-9) Color-image stabilizer

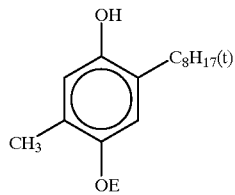

(Cpd-10) Color-image stabilizer (Cpd-11) Surface-active agent
A mixture in 3:1:3 in weight ratio of (1), (2), (3)

(1)

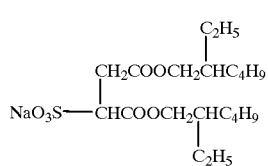

(2)

$C_8F_{17}SO_2NCH_2COOK$
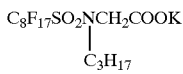
$C_3H_{17}$ (3)

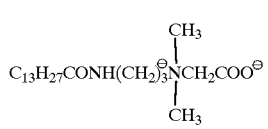

(Cpd-12) Surface-active agent (1)

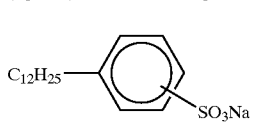

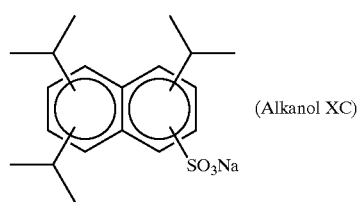
(Alkanol XC)
A mixture in 1:1 of (1) and (2)
(Solv-2) Solvent
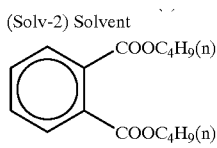
(Solv-4) Solvent
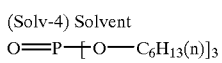
(Solv-6) Solvent
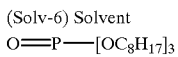
(Solv-8) Solvent
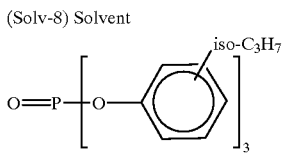
(UV-A) Ultra-violet absorbent
(1)
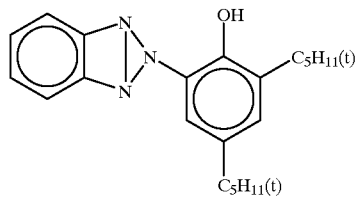
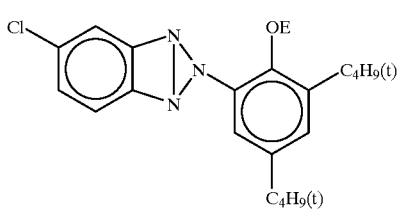
(UV-B) Ultra-violet absorbent
(1)
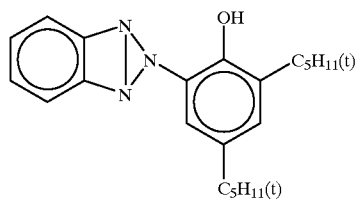
(2)
(Solv-1) Solvent
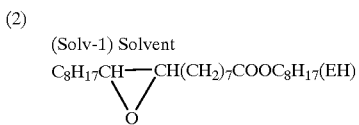
(Solv-3) Solvent
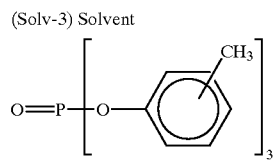
(Solv-5) Solvent
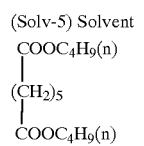
(Solv-7) Solvent
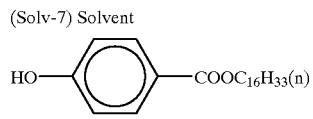
(Solv-9) Solvent
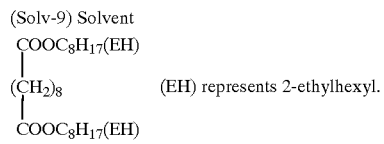
(EH) represents 2-ethylhexyl.
(2)
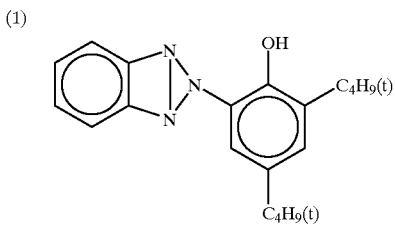
(4)
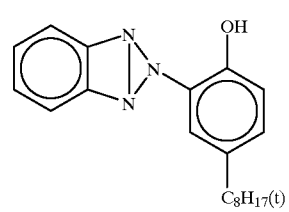
A mixture in 5:2:2:1 (weight ratio) of (1), (2), (3) and (4)
(2)
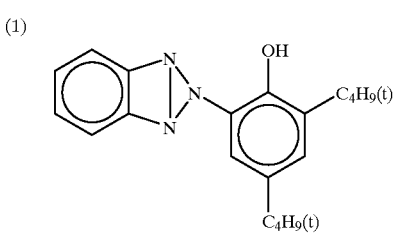

-continued

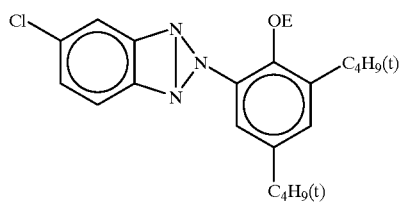
(3)

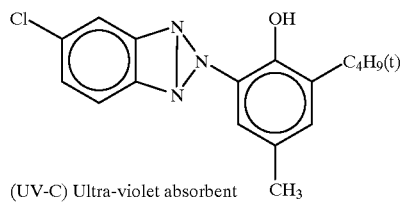
(4)

(UV-C) Ultra-violet absorbent

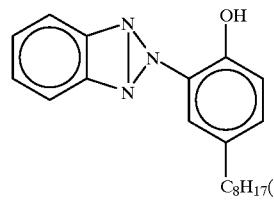
(5)

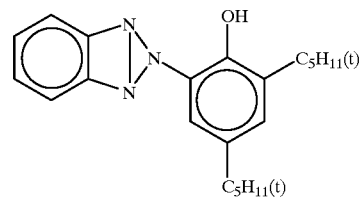
(1)

A mixture in 5:2:2:2:1 (weight ratio) of (1), (2), (3), (4) and (5)

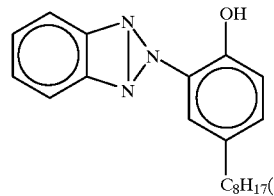
(2)

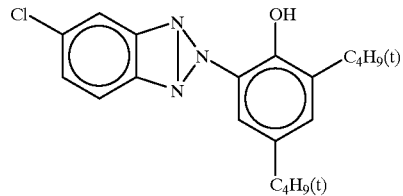
(3)

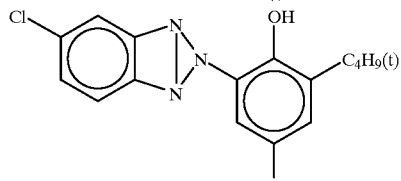
(3)

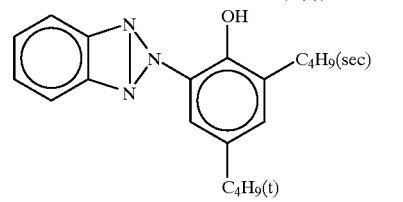
(5)

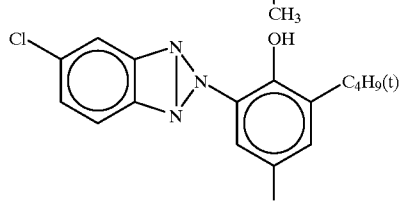
(4)

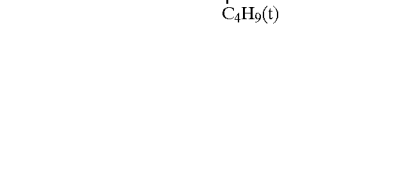
(6)

A mixture in 5:2:2:2:3:1 (weight ratio) of (1), (2), (3), (4), (5) and (6)

Light-Sensitive Materials 102 to 139 were prepared in the same manner as in the thus prepared Light-Sensitive Material 101, except that the composition in the fifth layer was changed as shown in Table 3 shown below. In these changes, the couplers of general formula (A) were changed but used in equivalent mols. Further, the average grain sizes of the coupler-containing lipophilic fine grains prepared in the preparation of these samples were all in the range of 0.17 to 0.19 μm.

TABLE 3

| Sample No. | Coupler of general formula (A) | Compound of general formula (B) or (C) | Ratio of (B) or (C) to (A) | Color-forming property Dmax | Cyan contamination | Processing cyan stain ΔD | Color reproduction | Fastness to light (residual rate %) | Remarks |
|---|---|---|---|---|---|---|---|---|---|
| 101 | Cp-1 | — | — | 2.30 | 0.39 | 0.05 | ○ | 65 | Comparative example |
| 102 | Cp-1 | Ph-(17) | 30 | 2.29 | 0.19 | 0.01 | ○ | 82 | This invention |
| 103 | Cp-1 | Ph-(18) | 30 | 2.25 | 0.21 | 0.02 | ○ | 83 | " |
| 104 | Cp-1 | Ph-(19) | 30 | 2.30 | 0.21 | 0.01 | ○ | 82 | " |
| 105 | Cp-1 | Ph-(20) | 30 | 2.20 | 0.22 | 0.01 | ○ | 80 | " |
| 106 | Cp-1 | Ph-(21) | 30 | 2.19 | 0.21 | 0.01 | ○ | 84 | " |
| 107 | Cp-1 | Ph-(22) | 30 | 2.30 | 0.22 | 0.02 | ○ | 86 | " |
| 108 | Cp-3 | Ph-(23) | 15 | 2.30 | 0.27 | 0.02 | ○ | 78 | " |
| 109 | Cp-3 | Ph-(28) | 10 | 2.31 | 0.28 | 0.02 | ○ | 81 | " |
| 110 | Cp-16 | Ph-(30) | 15 | 2.33 | 0.25 | 0.03 | ○ | 82 | " |
| 111 | Cp-22 | Ph-(33) | 10 | 2.27 | 0.25 | 0.02 | ○ | 78 | " |
| 112 | CP-23 | Ph-(42) | 15 | 2.24 | 0.22 | 0.02 | ○ | 79 | " |
| 113 | Cp-25 | Ph-(44) | 20 | 2.22 | 0.25 | 0.01 | ○ | 82 | " |

TABLE 3-continued

| Sample No. | Coupler of general formula (A) | Compound of general formula (B) or (C) | Ratio of (B) or (C) to (A) | Color-forming property Dmax | Cyan contamination | Processing cyan stain ΔD | Color reproduction | Fastness to light (residual rate %) | Remarks |
|---|---|---|---|---|---|---|---|---|---|
| 114 | Cp-31 | Ph-(40) | 25 | 2.21 | 0.22 | 0.01 | ○ | 83 | " |
| 115 | Cp-35 | Ph-(53) | 30 | 2.29 | 0.20 | 0.01 | ○ | 80 | " |
| 116 | CP-38 | Ph-(54) | 15 | 2.26 | 0.23 | 0.02 | ○ | 79 | " |
| 117 | Cp-42 | Ph-(56) | 10 | 2.19 | 0.25 | 0.03 | ○ | 71 | " |
| 118 | A | Ph-(17) | 30 | 1.97 | 0.23 | 0.01 | x | 53 | Comparative example |
| 119 | B | Ph-(17) | 30 | 2.05 | 0.22 | 0.02 | x | 43 | " |
| 120 | C | Ph-(17) | 30 | 1.86 | 0.22 | 0.01 | x | 42 | " |
| 121 | Cp-1 | a | 30 | 2.20 | 0.31 | 0.03 | ○ | 69 | " |
| 122 | Cp-1 | b | 30 | 2.23 | 0.32 | 0.02 | ○ | 71 | " |
| 123 | CP-1 | c | 30 | 2.19 | 0.33 | 0.03 | ○ | 66 | " |

TABLE 4

| Sample No. | Coupler of general formula (A) | Compound of general formula (B) or (C) | Ratio of (B) or (C) to (A) | Color-forming property Dmax | Cyan contamination | Processing cyan stain ΔD | Color reproduction | Fastness to light (residual rate %) | Remarks |
|---|---|---|---|---|---|---|---|---|---|
| 125 | Cp-1 | Ph-(1) | 30 | 2.30 | 0.19 | 0.02 | ○ | 82 | This invention |
| 126 | Cp-1 | Ph-(2) | 30 | 2.26 | 0.22 | 0.02 | ○ | 83 | " |
| 127 | Cp-1 | Ph-(3) | 30 | 2.33 | 0.21 | 0.02 | ○ | 79 | " |
| 128 | Cp-1 | Ph-(5) | 30 | 2.31 | 0.20 | 0.02 | ○ | 81 | " |
| 129 | Cp-1 | Ph-(6) | 30 | 2.33 | 0.21 | 0.02 | ○ | 82 | " |
| 130 | Cp-1 | Ph-(68) | 30 | 2.25 | 0.20 | 0.02 | ○ | 81 | " |
| 131 | Cp-1 | Ph-(67) | 30 | 2.34 | 0.19 | 0.02 | ○ | 80 | " |
| 132 | Cp-1 | Ph-(8) | 30 | 2.16 | 0.23 | 0.02 | ○ | 79 | " |
| 133 | Cp-1 | Ph-(69) | 30 | 2.26 | 0.24 | 0.02 | ○ | 80 | " |
| 134 | Cp-1 | Ph-(70) | 30 | 2.29 | 0.19 | 0.02 | ○ | 84 | " |
| 135 | Cp-1 | Ph-(71) | 30 | 2.21 | 0.25 | 0.02 | ○ | 82 | " |
| 136 | Cp-1 | Ph-(72) | 30 | 2.18 | 0.22 | 0.02 | ○ | 81 | " |
| 137 | Cp-1 | Ph-(73) | 30 | 2.27 | 0.23 | 0.02 | ○ | 80 | " |
| 138 | Cp-1 | Ph-(78) | 30 | 2.33 | 0.21 | 0.02 | ○ | 82 | " |
| 139 | Cp-1 | Ph-(80) | 30 | 2.29 | 0.23 | 0.02 | ○ | 80 | " |

Further, the comparative couplers A to C shown in the Table were as follows.

A.

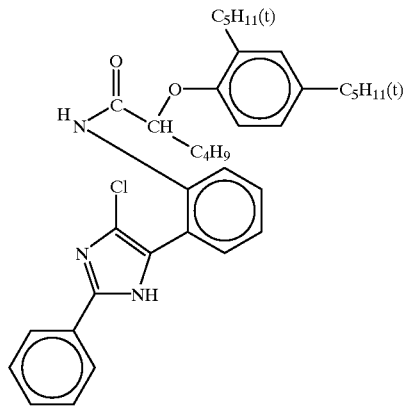

Compound described in EP-249453

B.

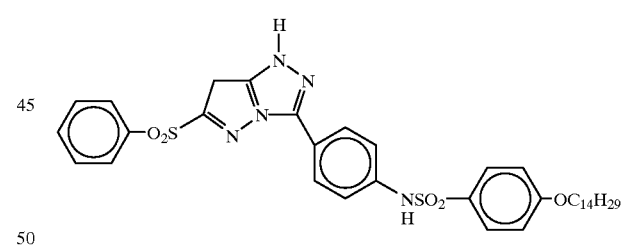

Compound described in JP-A-64-557

C.

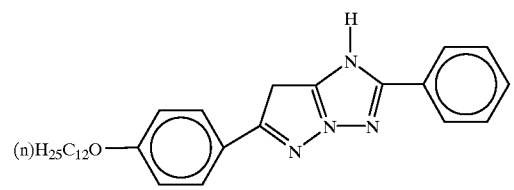

Compound described in JP-A-62-279340

The comparative compounds a, b, c, shown in the Table were as follows.

Comparative compound

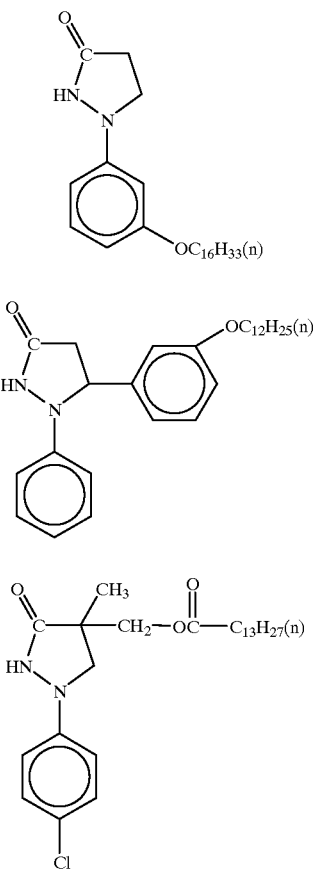

a, b and c each are compounds described in JP-A-5-150423

First, Light-Sensitive Material 104 was exposed to light image-wise, so that about 30% of the coated amount of silver might be developed, and then it was continuously processed using a paper processor until the replenishment rate of the color-developing solution in the following processing steps became twice the volume of the tank.

| Processing step | Temperature | Time | Replenishment rate | Tank volume |
|---|---|---|---|---|
| Color development | 38.5 °C. | 45 sec | 73 ml | 500 ml |
| Bleach-fix | 30–35° C. | 45 sec | 60 ml | 500 ml |
| Rinse (1) | 30–35° C. | 20 sec | — | 500 ml |
| Rinse (2) | 30–35° C. | 20 sec | — | 500 ml |
| Rinse (3) | 30–35° C. | 20 sec | 370 ml | 500 ml |
| Drying | 70–80° C. | 60 sec | | |

*The replenishment rate was the amount per m² of the light-sensitive material.
(the rinse was conducted in a 3-tank counter-current system of Rinse (3) to Rinse (1))

The composition of each processing solution is shown below.

| | Tank solution | Replenisher |
|---|---|---|
| Color Developing Solution | | |
| Water | 700 ml | 700 ml |
| Sodium triisopropylene (β)-sulfonate | 0.1 g | 0.1 g |
| Ethylenediaminetetraacetic acid | 3.0 g | 3.0 g |
| Disodium 1,2-dihydroxybenzene-4,6-disulfonate | 0.5 g | 0.5 g |
| Triethanolamine | 12.0 g | 12.0 g |
| Potassium chloride | 6.5 g | — |
| Potassium bromide | 0.03 g | — |
| Potassium carbonate | 27.0 g | 27.0 g |
| Fluorescent whitening agent (WHITEX 4, made by Sumitomo Chemical Ind. Co.) | 1.0 g | 3.0 g |
| Sodium sulfite | 0.1 g | 0.1 g |
| Diethylhydroxylamine | 1.1 g | 1.1 g |
| Disodium-N,N-bis(sulfonatoethyl)-hydroxylamine | 10.0 g | 13.0 g |
| N-ethyl-N-(β-methane-sulfonamidoethyl)-3-methyl-4-aminoaniline sulfate | 5.0 g | 11.5 g |
| Water to make | 1000 ml | 1000 ml |
| pH (25° C.) | 10.0 | 11.0 |
| Bleach-fixing solution (Both tank solution and replenisher) | | |
| Water | | 600 ml |
| Ammonium thiosulfate (700 g/liter) | | 100 ml |
| Ammonium sulfite | | 40 g |
| Ethylenediaminetetraacetic acid iron(III) ammonium | | 55 g |
| Ethylenediaminetetraacetic acid disodium | | 5 g |
| Ammonium bromide | | 40 g |
| Nitric acid (67%) | | 30 g |
| Water to make | | 1000 ml |
| pH (25° C.) | | 4.8 |

(pH was adjusted by acetic acid and aqueous ammonium)
Rinse solution (Both tank solution and replenisher)
Ion-exchanged water (calcium and magnesium each were 3 ppm or below)

Then, the respective samples were subjected to gradation exposure to light through a three-color separation optical wedge for sensitometry using a sensitometer (FWH type, manufactured by Fuji Photo Film Co., Ltd.; color temperature of the light source: 3,200° K). This exposure was carried out such that the exposure amount would be 250 CMS by the exposure time of 0.1 sec.

Using these samples, the following evaluations were carried out.

Evaluation 1 (Color-forming Property: Dmax)

The exposed samples were processed with the above running solutions by using a paper processor. The maximum color density (Dmax) of cyan in the cyan color-formed section (red-exposed section) of each of the processed samples was measured by an X-Rite 350 densitometer (manufactured by The X-Rite Company).

Evaluation 2 (Cyan Color Contamination at the Time of Processing)

The cyan density in the section where the density of the magenta color-formed section (green-exposed section) of each of the processed samples gave 2.0 was measured, using the similar measuring apparatus as in Evaluation 1.

Evaluation 3 (Cyan Stain at the Time of Processing)

The difference between the cyan density of the Dmin section of each of the samples that were processed with a bleach-fix solution for cyan stain at the time of processing, which solution was prepared by changing the amount of ammonium sulfite contained in the above shown bleach-fix solution from 40 g to 4.0 g, and by changing the pH from 4.8 to 8.0, and the cyan density of the Dmin section of each of the samples that were processed with the above described bleach-fix solution, was determined, to designate this difference as cyan stain at the time of processing.

Evaluation 4 (Color Reproduction)

The reflection absorption spectrum of the cyan color-formed section processed in the processing step in Evaluation 1 was measured. The one whose association band present at the short-wave end of the main absorption band in the cyan region of the absorption spectrum was remarkably large, and whose hue was poor, was designated "X", and the one whose degree of the association band present at the short-wave end was appropriate and advantageous in view of the color reproduction, was designated "◯".

Evaluation V (Fastness to Light)

Each of the samples processed in the processing steps in Evaluation I was irradiated with light for 14 days using a xenon irradiator of 100,000 lux. During the irradiation, a heat-absorbing filter and an ultraviolet-absorbing filter, in the latter filter the light transmittance at 370 nm being 50%, were used. The cyan density residual rate (%) after the irradiation with light, at the points where the cyan density before the irradiation with light was 0.5, was found, to evaluate fastness to light. The evaluation results are also shown in Tables 3.

As is apparent from the results shown in Tables 3, the cyan image produced from the coupler represented by general formula (A) of the present invention has a high density and excellent color reproduction. (Comparison between Sample 101, in which a coupler represented by general formula (A) was used, and Samples 118, 119, and 120, in which Coupler A, B, or C for comparison was used)

Further, it can be understood that the coupler represented by general formula (A) of the present invention is high in processing cyan color contamination and cyan stain, and it is unsatisfactory in fastness to light, while in the case in which the compound represented by general formula (B) or (C) of the present invention is used additionally, all of cyan color contamination, cyan stain, and fastness to light are improved. (Comparison between Sample 101 and Samples 102 to 117)

On the other hand, it can be understood that, even when Compound a, b, or c for comparison is used additionally, the effect of improving cyan stain, cyan color contamination, and fastness to light is not satisfactory. (Comparison between Samples 102 to 117 and Samples 121 to 139)

Example 2

Samples 201 to 221 were prepared in the same manner as for Sample 101 in Example 1, except that the composition in the fifth layer was changed as shown in the below Table 4. Thereafter Samples 201 to 221 were exposed to light and subjected to development in the same manner as in Example 1, to evaluate various items. In passing, in the evaluation of fastness to light, the data of the initial density of 2.0 (Do: 2.0) are shown.

TABLE 5

| Sample No. | Coupler of general formula (A) | Compound of general formula (B) or (C) | Compound of general formula [F] | Processing color contamination | Processing cyan stain ΔD | Color reproduction | Fastness to light (residual rate %) | Remarks |
|---|---|---|---|---|---|---|---|---|
| 201 | Cp-1 | Ph-(1) (30)* | a-6 (100)* | 0.15 | 0.01 | ◯ | 91 | This invention |
| 202 | Cp-1 | Ph-(2) (30) | a-2 (100) | 0.17 | 0.02 | ◯ | 87 | " |
| 203 | Cp-1 | Ph-(3) (30) | a-3 (100) | 0.20 | 0.01 | ◯ | 88 | " |
| 204 | Cp-1 | Ph-(4) (30) | a-4 (100) | 0.21 | 0.02 | ◯ | 87 | " |
| 205 | Cp-1 | Ph-(5) (30) | a-5 (100) | 0.19 | 0.01 | ◯ | 85 | " |
| 206 | Cp-1 | Ph-(6) (30) | a-6 (100) | 0.17 | 0.02 | ◯ | 84 | " |
| 207 | Cp-2 | Ph-(7) (30) | a-6 (200) | 0.22 | 0.01 | ◯ | 82 | " |
| 208 | Cp-3 | Ph-(8) (30) | a-6 (150) | 0.17 | 0.01 | ◯ | 79 | " |
| 209 | Cp-4 | Ph-(1) (20) | a-8 (100) | 0.18 | 0.01 | ◯ | 82 | " |
| 210 | Cp-5 | Ph-(1) (30) | a-9 (100) | 0.19 | 0.02 | ◯ | 83 | " |
| 211 | Cp-6 | Ph-(1) (15) | a-20 (100) | 0.20 | 0.02 | ◯ | 85 | " |
| 212 | Cp-13 | Ph-(37) (20) | a-19 (100) | 0.21 | 0.01 | ◯ | 86 | " |
| 213 | Cp-16 | Ph-(9) (30) | a-29 (100) | 0.22 | 0.01 | ◯ | 82 | " |
| 214 | Cp-23 | Ph-(12) (30) | a-30 (100) | 0.19 | 0.02 | ◯ | 79 | " |
| 215 | Cp-29 | Ph-(13) (30) | a-33 (100) | 0.17 | 0.01 | ◯ | 81 | " |
| 216 | Cp-31 | Ph-(14) (30) | a-41 (100) | 0.18 | 0.02 | ◯ | 83 | " |
| 217 | Cp-33 | Ph-(20) (30) | a-52 (100) | 0.19 | 0.01 | ◯ | 84 | " |
| 218 | Cp-35 | Ph-(23) (30) | a-53 (100) | 0.22 | 0.01 | ◯ | 86 | " |
| 219 | Cp-1 | Ph-(25) (30) | a-54 (100) | 0.21 | 0.02 | ◯ | 87 | " |
| 220 | Cp-1 | Ph-(26) (30) | a-1 (100) | 0.19 | 0.01 | ◯ | 82 | " |
| 221 | Cp-1 | Ph-(29) (30) | a-2 (100) | 0.22 | 0.01 | ◯ | 84 | " |
| 101 | Cp-1 | — | — | 0.39 | 0.05 | ◯ | 65 | Comparative example |

*number in ( ) is the ratio to (A)

According to Table 4, it can be understood that, when the cyan coupler of general formula (A) and the phenidone compound defined in the present invention are used in combination, and the compound represented by [F] is also used, the effect of the present invention is further more effectively exhibited.

Example 3

Sample 301 was prepared in the same manner as Sample 101 in Example 1, except that following points were changed.

(Layer Constitution)

The composition of each layer is shown below. The numbers show coating amounts (g/m$^2$). In the case of the silver halide emulsion, the coating amount is in terms of silver.

Base

Polyethylene Laminated Paper

[The polyethylene on the first layer side contained a white pigment (TiO$_2$: content of 20 wt %), and a blue dye (ultramarine)]

| First Layer (Blue-Sensitive Emulsion Layer) | |
|---|---|
| A silver chlorobromide emulsion A: cubes, a mixture of a large-size emulsion A having an average grain size of 0.89 μm, and a small-size emulsion A having an average grain size of 0.71 μm (3:7 in terms of mol of silver). The deviation coefficients of the grain size distributions were 0.08 and 0.10, respectively, and each emulsion had 0.3 mol % of silver bromide locally contained in part of the grain surface whose substrate was made up of silver chloride. | 0.25 |
| Gelatin | 1.4 |
| Yellow coupler (ExY) | 0.62 |
| Color-image stabilizer (Cpd-1) | 0.040 |
| Color-image stabilizer (Cpd-2) | 0.032 |
| Color-image stabilizer (Cpd-3) | 0.086 |
| Color-image stabilizer (Cpd-5) | 0.015 |
| Color-image stabilizer (Cpd-13) | 0.035 |
| Solvent (Solv-3) | 0.14 |
| Solvent (Solv-6) | 0.070 |
| Second Layer (Color-Mixing Inhibiting Layer) | |
| Gelatin | 1.1 |
| Color-mixing inhibitor (Cpd-4) | 0.11 |
| Color-image stabilizer (Cpd-7) | 0.17 |
| Solvent (Solv-1) | 0.070 |
| Solvent (Solv-2) | 0.28 |
| Solvent (Solv-7) | 0.011 |
| Third Layer (Green-Sensitive Emulsion Layer) | |
| A silver chlorobromide emulsion: cubes, a mixture of a large-size emulsion B having an average grain size of 0.56 μm, and a small-size emulsion B having an average grain size of 0.39 μm (1:3 in terms of mol of silver). The deviation coefficients of the grain size distributions were 0.10 and 0.08, respectively, and each emulsion had 0.7 mol % of silver bromide locally contained in part of the grain surface whose substrate was made up of silver chloride. | 0.12 |
| Gelatin | 1.3 |
| Magenta coupler (ExM) | 0.14 |
| Ultraviolet absorbing agent (UV-E) | 0.13 |
| Color-image stabilizer (Cpd-2) | 0.011 |
| Color-image stabilizer (Cpd-5) | 0.011 |
| Color-image stabilizer (Cpd-6) | 0.010 |
| Color-image stabilizer (Cpd-7) | 0.080 |
| Color-image stabilizer (Cpd-8) | 0.028 |
| Color-image stabilizer (Cpd-10) | 0.0022 |
| Solvent (Solv-4) | 0.20 |
| Solvent (Solv-5) | 0.10 |
| Solvent (Solv-8) | 0.20 |
| Fourth Layer (Color-Mixing Inhibiting Layer) | |
| Gelatin | 1.1 |
| Color-mixing inhibitor (Cpd-4) | 0.11 |
| Color-image stabilizer (Cpd-7) | 0.17 |
| Solvent (Solv-1) | 0.070 |
| Solvent (Solv-2) | 0.28 |
| Solvent (Solv-7) | 0.011 |
| Fifth Layer (Red-Sensitive Emulsion Layer) | |
| A silver chlorobromide emulsion: cubes, a mixture of a large-size emulsion having an average grain size of 0.57 μm, and a small-size emulsion having an average grain size of 0.42 μm (1:4 in terms of mol of silver). The deviation coefficients of the grain size distributions were 0.09 and 0.11, respectively, and each emulsion had 0.7 mol % of silver bromide locally contained in part of the grain surface whose substrate was made up of silver chloride. | 0.10 |
| Gelatin | 0.91 |
| Cyan coupler (Exemplified compound 1) | 0.15 |
| Solvent (Solv-8) | 0.38 |
| Sixth Layer (Ultraviolet Absorbing Layer) | |
| Gelatin | 0.75 |
| Ultraviolet absorbing agent (UV-F) | 0.33 |
| Solvent (Solv-10) | 0.18 |
| Seventh Layer (Protective Layer) | |
| Acid-processed gelatin | 1.0 |
| Acryl-modified copolymer of polyvinyl alcohol (modification degree: 17%) | 0.043 |
| Liquid paraffin | 0.018 |
| Surface-active agent (Cpd-11) | 0.026 |

(Cpd-13) Color-image stabilizer (Solv-10) Solvent (UV-E) Ultra-violet absorbent

-continued

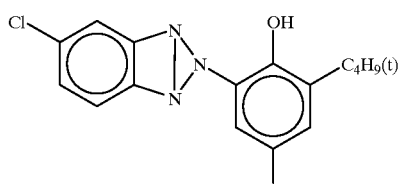

A mixture in 4:3:2:2 (weight ratio) of (1), (2), (3) and (4)

(UV-F) Ultra-violet absorbent

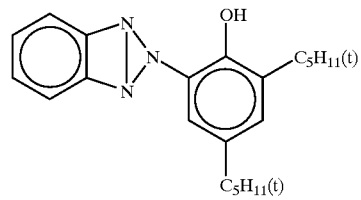

(1)

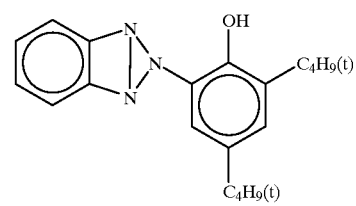

(2)

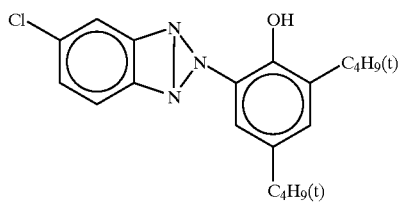

(3)

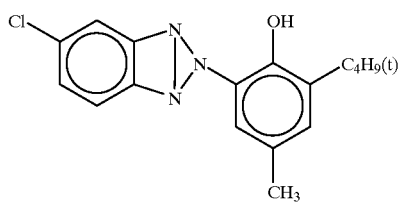

(4)

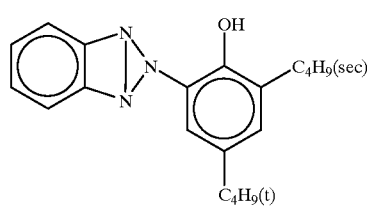

(5)

A mixture in 6:2:2:2:3 (weight ratio) of (1), (2), (3), (4) and (5)

Further, as a water-soluble dye to prevent irradiation, the following compounds were added to the second, forth and sixth layers in the divided amounts.

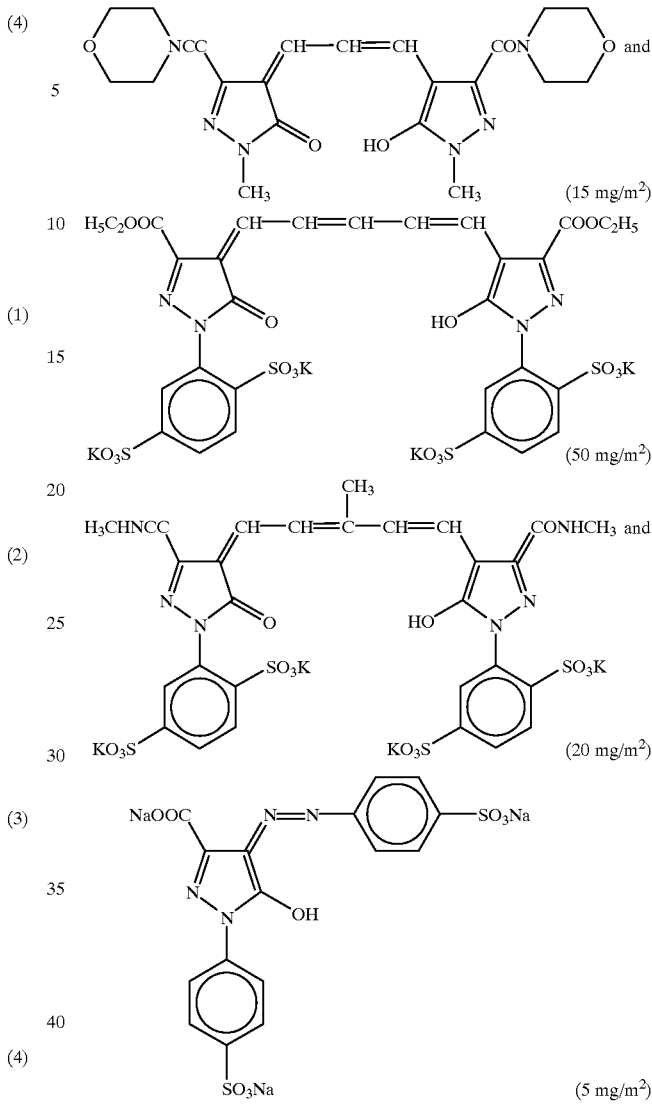

Samples 302 to 321 were prepared in the same manner as Sample 301, except that the composition of the oil-soluble components including couplers in the fifth layer of sample 301 was changed to those the same as Samples 202 to 221 in Examples 2. Then, the same evaluations as in Example 1 were carried out. As a result, it is found that, according to the present invention, a light-sensitive material that is excellent in color-forming property, processing stability, color reproduction, and fastness to light, can be obtained.

Example 4

Samples 402 to 417 were prepared in the same manner as in Samples 102 to 117, except that, in the fifth layer, the compound (a-6) represented by general formula (F) was additionally added in an amount of 150 mol % to the coupler. Then, the same evaluations as in Example 1 were carried out. As a result, it is found that fastness to light is further improved.

Example 5

Sample 501 was prepared in the same manner as in Sample 101 in Example 1, except that following points were changed.

In place of the solvent (Solv-8) 0.45 in the fifth layer:

| | |
|---|---|
| Color-image stabilizer ADF-1 | 0.01 |
| Color-image stabilizer ADF-2 | 0.01 |
| Color-image stabilizer ADF-3 | 0.05 |
| Color-image stabilizer ADF-4 | 0.06 |
| Color-image stabilizer ADF-5 | 0.101 |
| Color-image stabilizer ADF-6 | 0.05 |
| Stain-inhibiting agent Cpd-14 | 0.008 |
| Stain-inhibiting agent Cpd-15 | 0.079 |
| Solvent (Solv-8) | 0.13 |

ADF-1

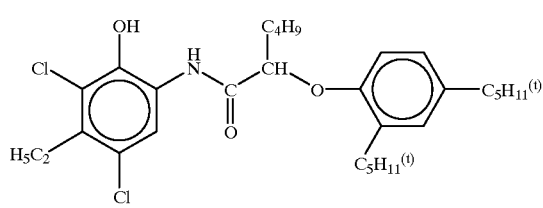

ADF-2

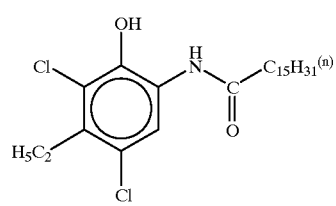

ADF-3

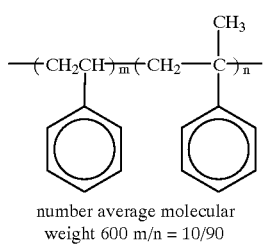

number average molecular weight 600 m/n = 10/90

ADF-4

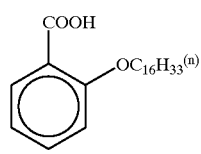

ADF-5

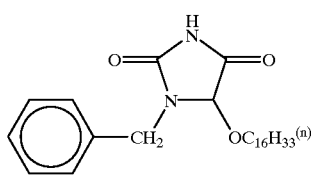

ADF-6

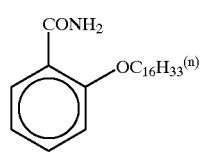

-continued

Cpd-14

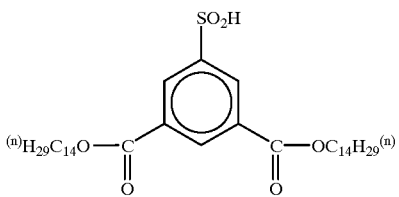

Cpd-15

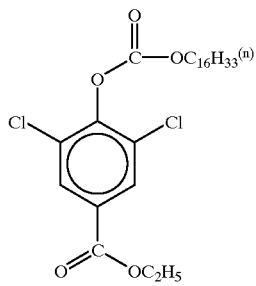

Samples 502 to 539 corresponding to Samples 102 to 139 were prepared with similar changes made, and the same evaluations as in Example 1 were carried out.

As a result, it is found that the fastness to light was further increased, and cyan stain and cyan color contamination at the time of processing were further reduced.

As is explained in detail above, by the present invention that uses a specific cyan coupler and a specific phenidone compound in combination, a silver halide color photographic light-sensitive material can be obtained that is excellent in color-forming property and color reproduction, low in cyan color contamination and cyan stain, and high in fastness.

The method of synthesizing α-alkyl acrylates of the present invention can make the synthesis possible from inexpensive raw materials, in a short step, in short period of time, in a high yield. Since the α-alkyl acrylates synthesized by the synthetic method of the present invention is high in purity, it can react with a hydrazine without isolating and purifying it, to synthesize a phenidone compound in a high yield.

Having described our invention as related to the present embodiments, it is our intention that the invention not be limited by any of the details of the description, unless otherwise specified, but rather be construed broadly within its spirit and scope as set out in the accompanying claims.

Industrial Applicability

The silver halide color photographic light-sensitive material according to the present invention is excellent in quality, such as color reproduction and fastness, and it can be used as color films, color photographic printing papers, and the like. The method of producing a phenidone compound and its intermediate of the present invention is preferably suitable as a method of producing a phenidone compound industrially at a low cost, which compound can be used for producing the above high-quality silver halide color photographic light-sensitive material.

What is claimed is:

1. A silver halide color photographic light-sensitive material, containing at least one compound represented by the following general formula (IX) in any one of photographic constitutional layers on a base:

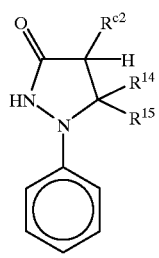

(IX)

wherein, in formula (IX), $R^{c2}$ represents an alkyl group having 12 to 30 carbon atoms, or an alkenyl group having 12 to 30 carbon atoms, and $R^{14}$ and $R^{15}$, which are the same or different, each independently represent a hydrogen atom, an alkyl group having 1 to 20 carbon atoms, or an aryl group having 6 to 20 carbon atoms.

2. The silver halide color photographic light-sensitive material according to claim 1, wherein $R^{c2}$ in formula (IX) represents an alkyl group having 14–28 carbon atoms or an alkenyl group having 12–30 carbon atoms.

3. The silver halide color photographic light-sensitive material according to claim 2, wherein the alkenyl group designated by $R^{c2}$ in formula (IX) has 14–28 carbon atoms.

4. The silver halide color photographic light-sensitive material according to claim 2, wherein the alkyl group designated by $R^{c2}$ in formula (IX) has 16–26 carbon atoms.

5. The silver halide color photographic light-sensitive material according to claim 2, wherein the alkenyl group designated by $R^{c2}$ in formula (IX) has 16–26 carbon atoms.

6. The silver halide color photographic light-sensitive material according to claim 1, wherein the compound represented by formula (IX) has a molecular weight of 350 or more.

7. The silver halide color photographic light-sensitive material according to claim 1, wherein both $R^{14}$ and $R^{15}$ in formula (IX) represent a hydrogen atom.

8. The silver halide color photographic light-sensitive material according to claim 1, wherein the compound represented by formula (IX) is a compound selected from a group consisting of Ph-(1), Ph-(2), Ph-(5), Ph-(6), Ph-(7), Ph-(8), Ph-(9), Ph-(14), Ph-(15), Ph-(45), Ph-(67), Ph-(68), Ph-(69), Ph-(70), Ph-(72), Ph-(74), and Ph-(76), Ph-(77), Ph-(78), Ph-(79) and Ph-(80):

Ph-(1)

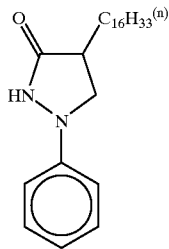

-continued

Ph-(2)

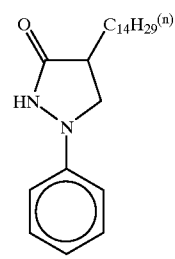

Ph-(5)

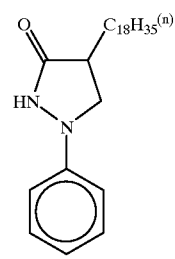

Ph-(6)

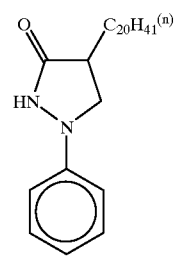

Ph-(7)

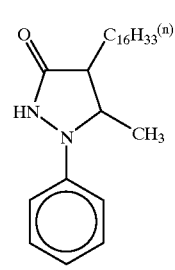

Ph-(8)

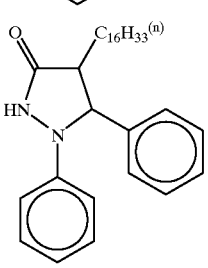

Ph-(9)

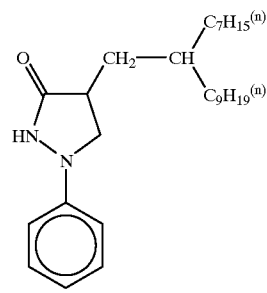

-continued
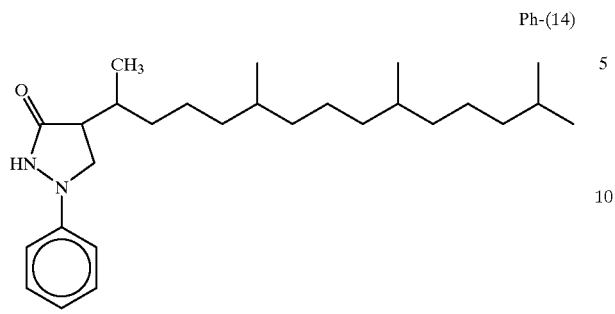 Ph-(14)
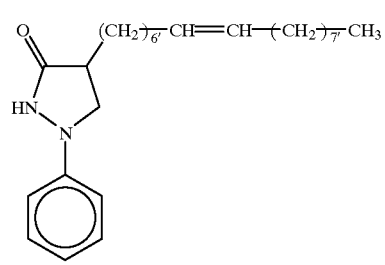 Ph-(15)
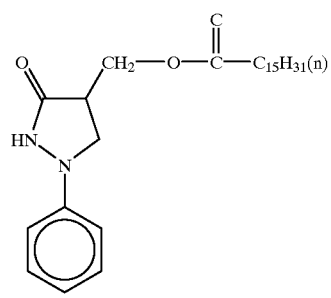 Ph-(45)
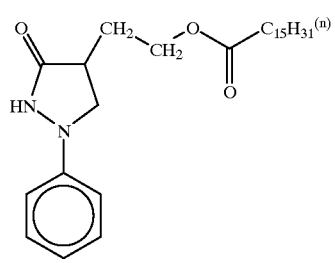 Ph-(67)
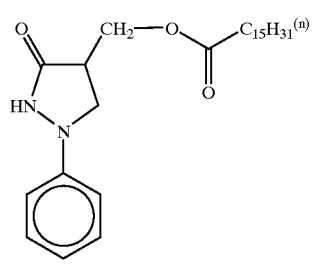 Ph-(68)
-continued
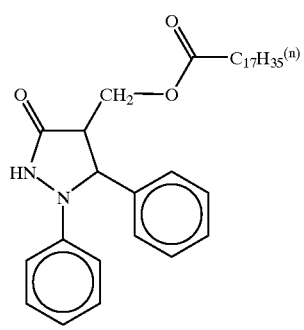 Ph-(69)
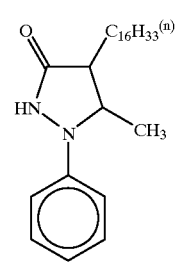 Ph-(70)
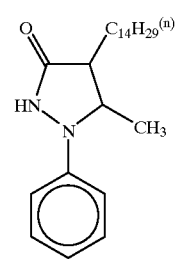 Ph-(72)
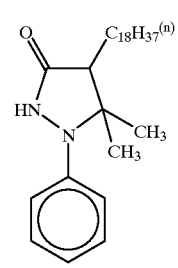 Ph-(74)
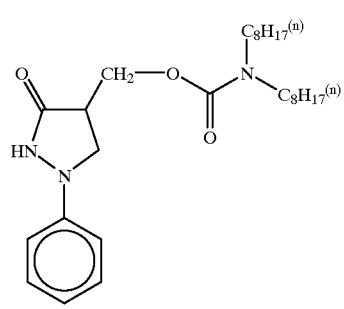 Ph-(76)

Ph-(77)

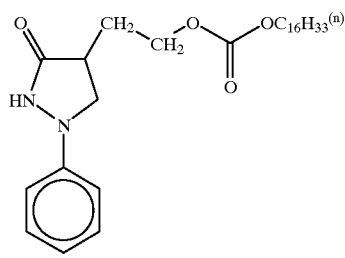

Ph-(78)

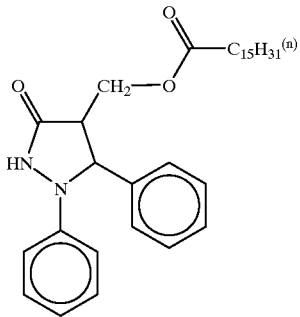

Ph-(79)

Ph-(80)

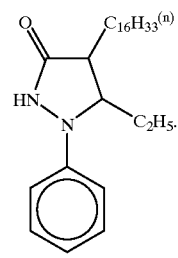

9. The silver halide color photographic light-sensitive material according to claim 1, wherein the compound represented by formula (IX) is contained in the photographic constitutional layer, being dispersed in a high-boiling organic solvent.

10. The silver halide color photographic light-sensitive material according to claim 9, wherein the high-boiling organic solvent is a compound represented by formula (E):

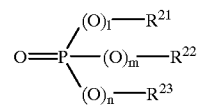

(E)

wherein, $R^{21}$, $R^{22}$, and $R^{23}$ each represent an acyclic alkyl group, a cycloalkyl group, or an aryl group, and 1, m, and n each represent 1 or 0.

* * * * *